(12) United States Patent
Hirschel et al.

(10) Patent No.: US 10,143,806 B2
(45) Date of Patent: Dec. 4, 2018

(54) DRIVE AND DOSING DEVICE WITH A STOP ELEMENT FOR PREVENTING THE SETTING OF A DOSE

(71) Applicant: TecPharma Licensing AG, Burgdorf (CH)

(72) Inventors: Juerg Hirschel, Bern (CH); Ursina Streit, Schöbühl (CH); Patrick Hostettler, Hasle (CH)

(73) Assignee: TECPHARMA LICENSING AG, Burgdorf (CH)

( * ) Notice: Subject to any disclaimer, the term of this patent is extended or adjusted under 35 U.S.C. 154(b) by 379 days.

(21) Appl. No.: 14/997,002

(22) Filed: Jan. 15, 2016

(65) Prior Publication Data

US 2016/0129196 A1    May 12, 2016

Related U.S. Application Data

(63) Continuation of application No. PCT/CH2014/000090, filed on Jul. 1, 2014.

(30) Foreign Application Priority Data

Jul. 22, 2013    (EP) .................................... 13177387

(51) Int. Cl.
*A61M 5/315*    (2006.01)
*A61M 5/24*    (2006.01)

(52) U.S. Cl.
CPC .... *A61M 5/31536* (2013.01); *A61M 5/31528* (2013.01); *A61M 5/31541* (2013.01);
(Continued)

(58) Field of Classification Search
CPC .......... A61M 5/31536; A61M 5/31528; A61M 5/31541; A61M 5/31585; A61M 5/31551;
(Continued)

(56) References Cited

FOREIGN PATENT DOCUMENTS

| WO | WO 2001/019434 | 3/2001 |
|---|---|---|
| WO | WO 2004/020027 | 3/2004 |

(Continued)

OTHER PUBLICATIONS

International Search Report for application No. PCT/CH2014/000090 dated Sep. 19, 2014, 2 pages.
(Continued)

*Primary Examiner* — Amber Stiles
(74) *Attorney, Agent, or Firm* — Dorsey & Whitney LLP

(57) ABSTRACT

Drive and dosing devices for injection devices are disclosed. An embodiment may include a threaded piston rod moveable in a dispensing direction for dispensing a product. A rotation member may be operatively connected to a stop limiter and threadably engaged with the piston rod. Rotation of the rotation member may cause the piston rod to move in the dispensing direction. An embodiment may include a dose knob rotatable for changing a dose. The device may further include a stop element threadably engaged with the piston rod and having a catch. The dose knob may be coupled with the stop element such that during increase of a dose, the stop element is screwed toward the distal end of the piston rod and the catch is moved towards the stop limiter. The stop element prevents increasing a dose when the catch abuts the stop limiter.

16 Claims, 23 Drawing Sheets

(52) U.S. Cl.
CPC .... *A61M 5/31543* (2013.01); *A61M 5/31551* (2013.01); *A61M 5/31585* (2013.01); *A61M 2005/2488* (2013.01); *A61M 2205/581* (2013.01); *A61M 2205/582* (2013.01)

(58) Field of Classification Search
CPC ........ A61M 5/31543; A61M 2205/582; A61M 2205/581; A61M 2005/2488
See application file for complete search history.

(56) References Cited

FOREIGN PATENT DOCUMENTS

| WO | WO 2005/018721 | 3/2005 | |
|---|---|---|---|
| WO | WO 2007/017052 | 2/2007 | |
| WO | WO 2009/105910 | 9/2009 | |
| WO | WO 2010/105376 | 9/2010 | |
| WO | WO 2010105376 A1 * | 9/2010 | ........ A61M 5/31583 |
| WO | WO 2010/139691 | 12/2010 | |

OTHER PUBLICATIONS

International Preliminary Report on Patentability for application No. PCT/CH2014/000090 dated Jan. 26, 2016, 10 pages.

* cited by examiner

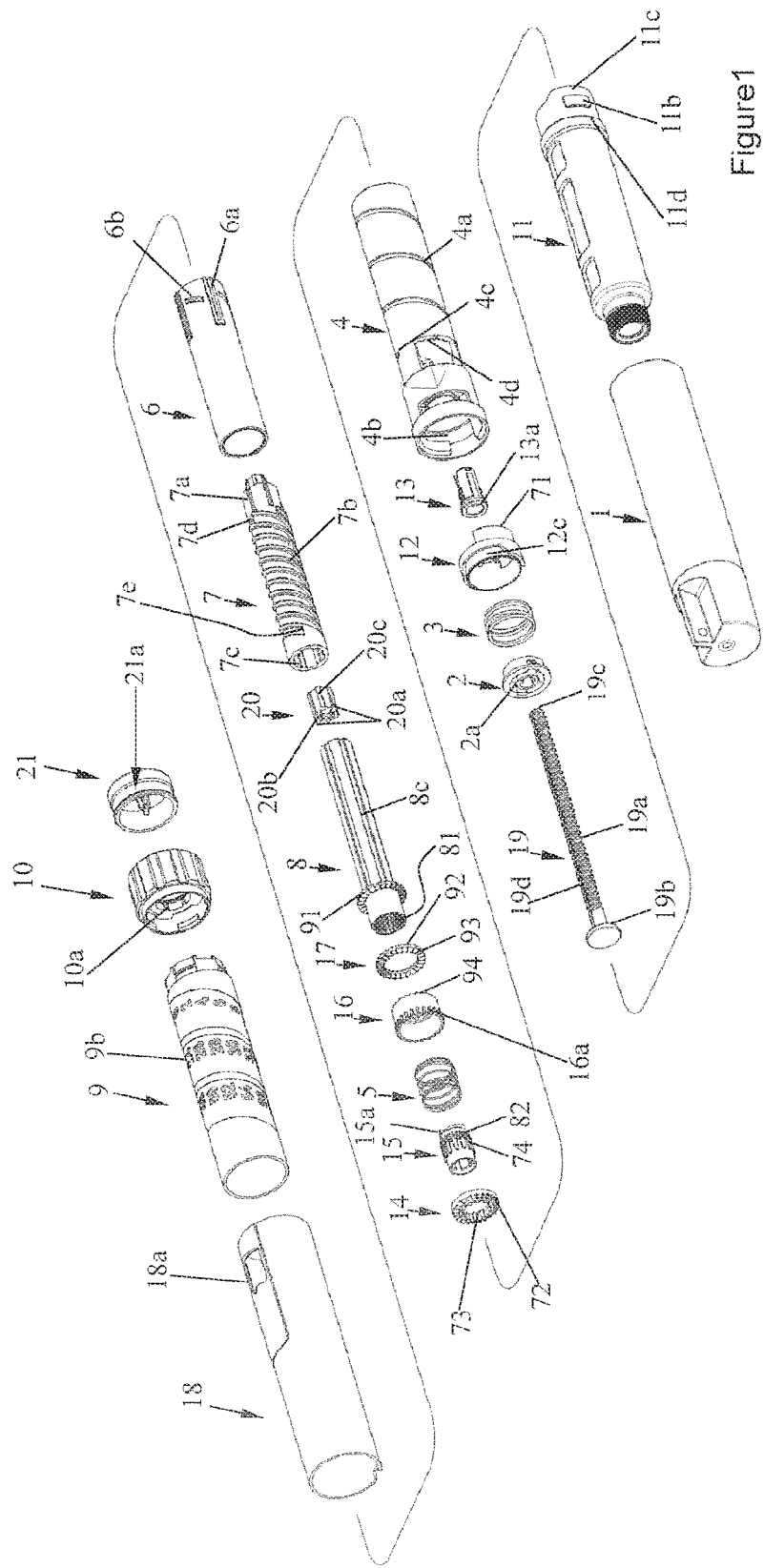

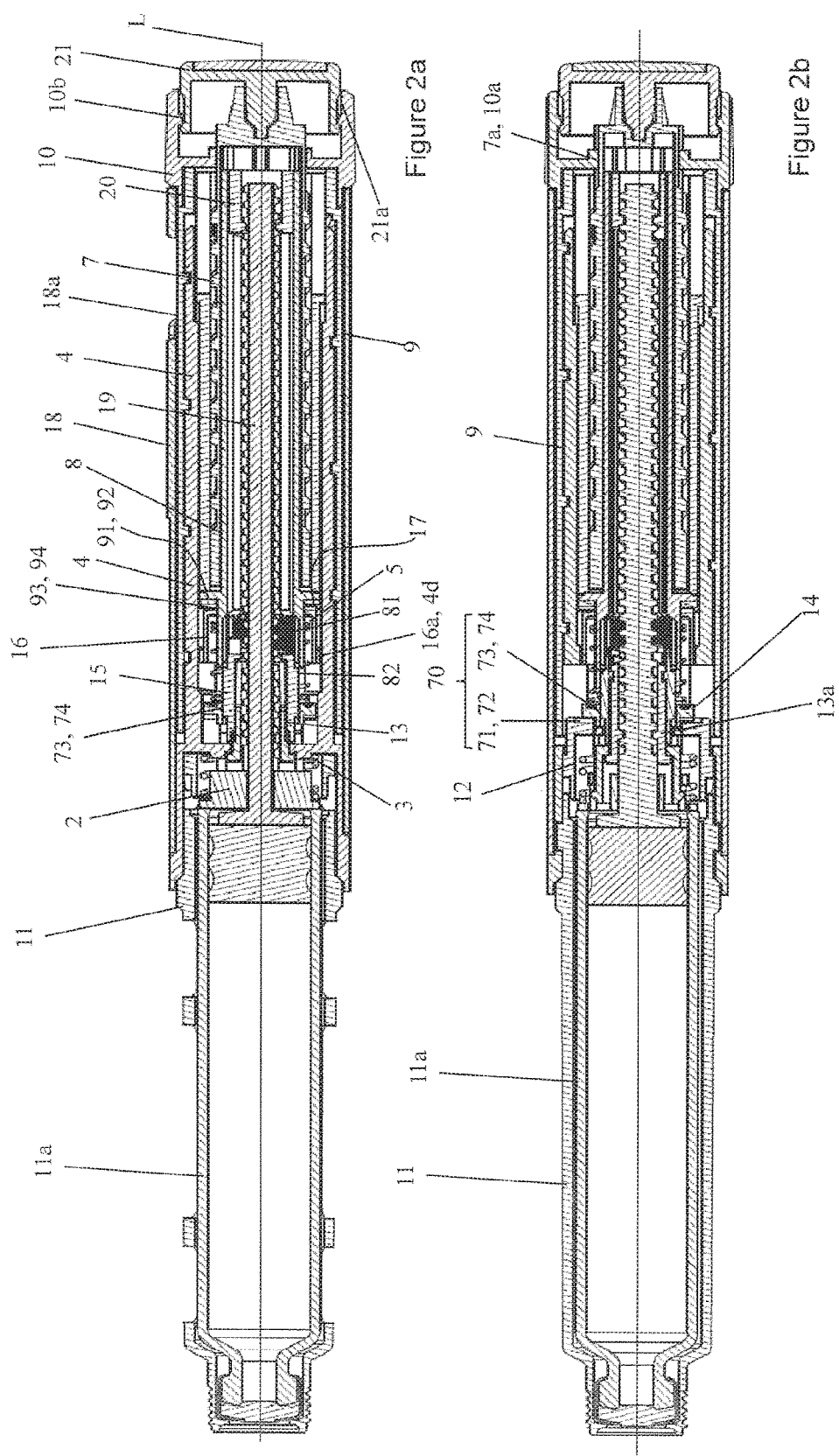

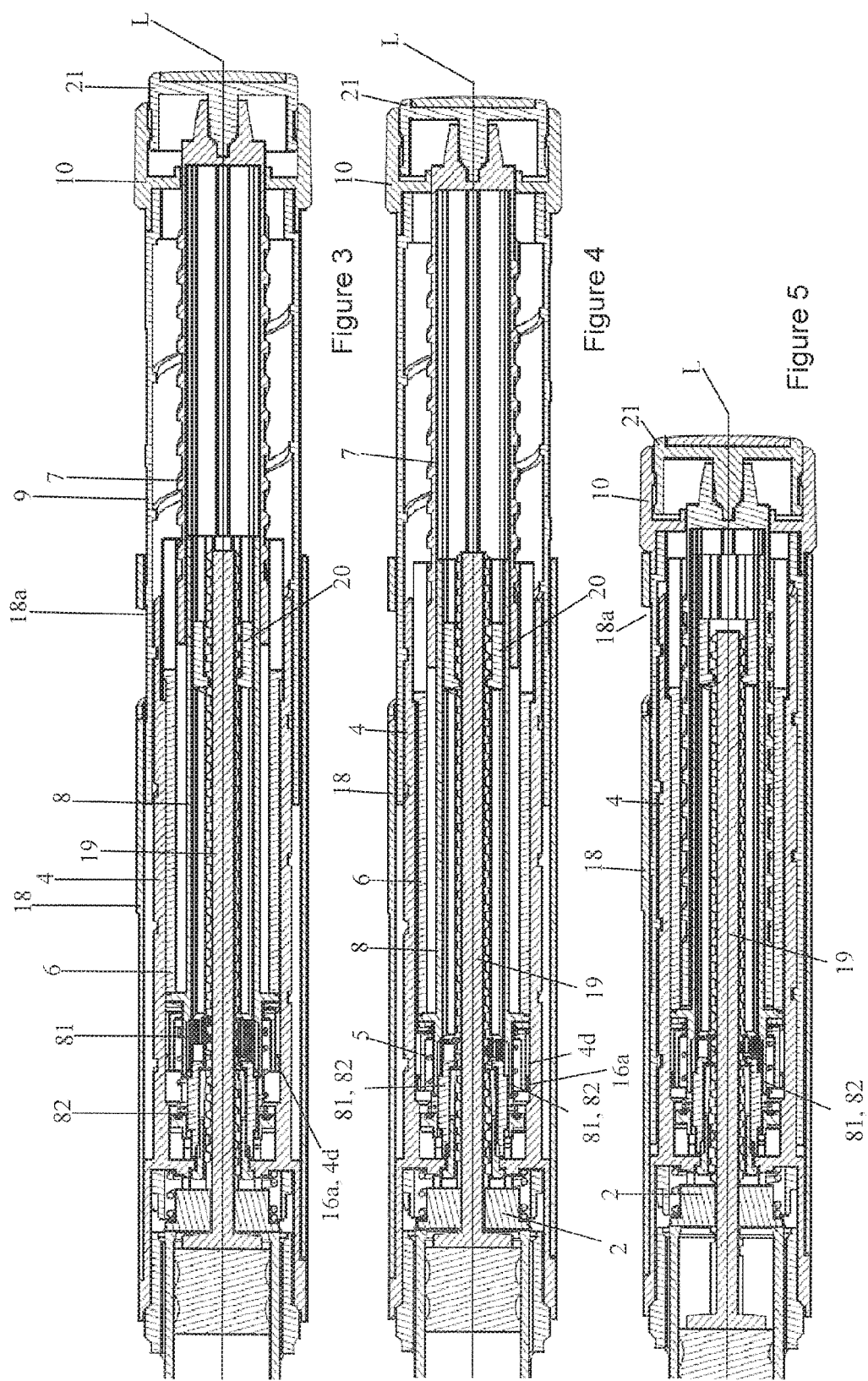

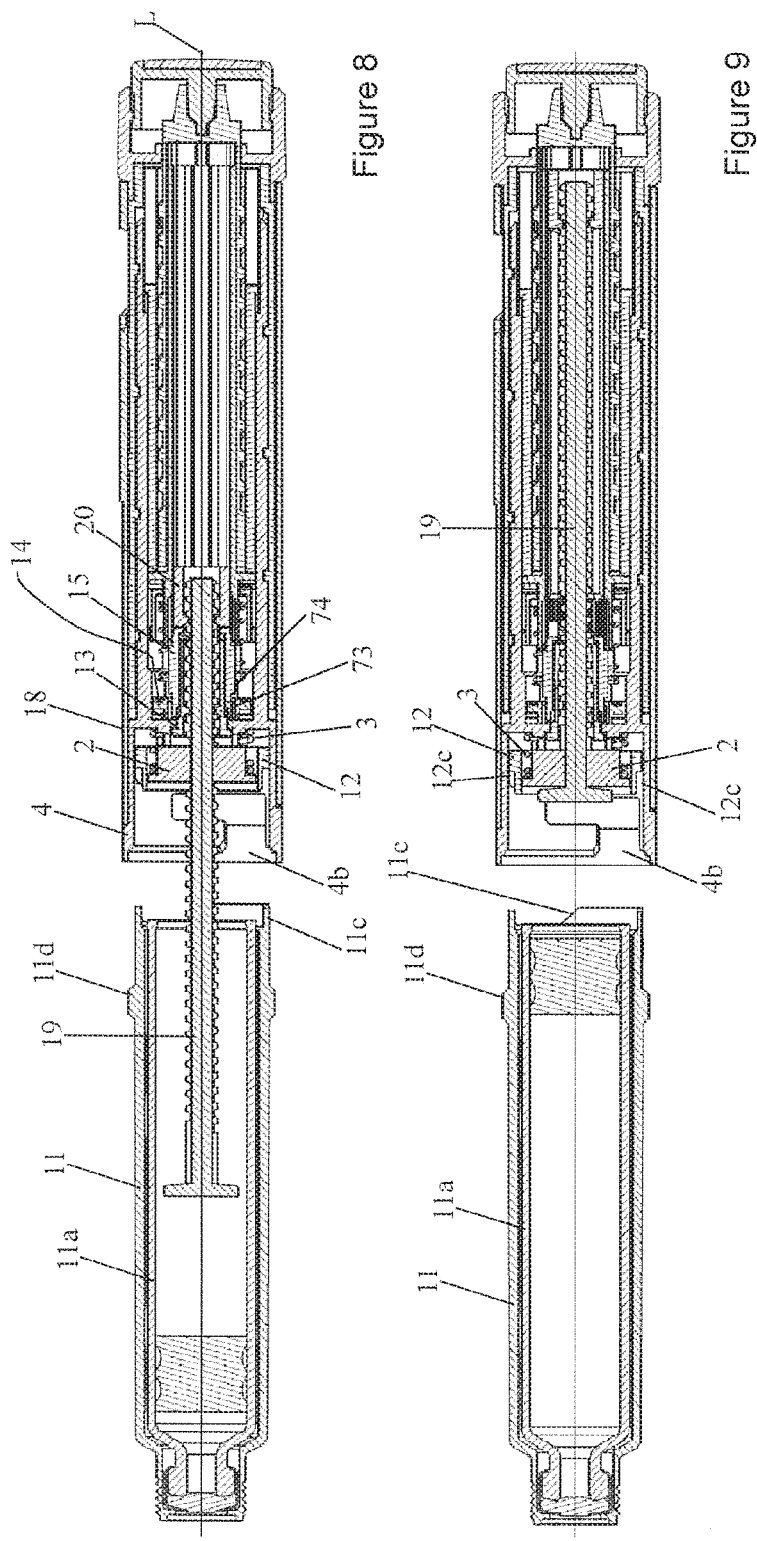

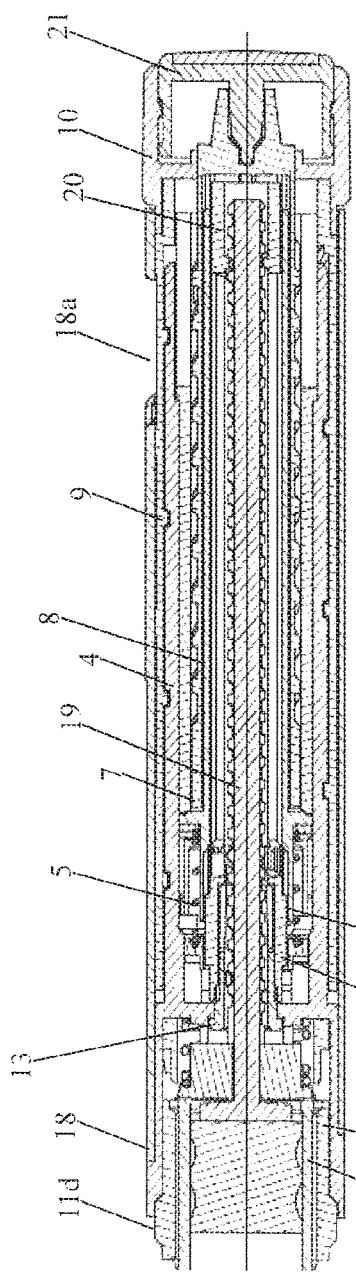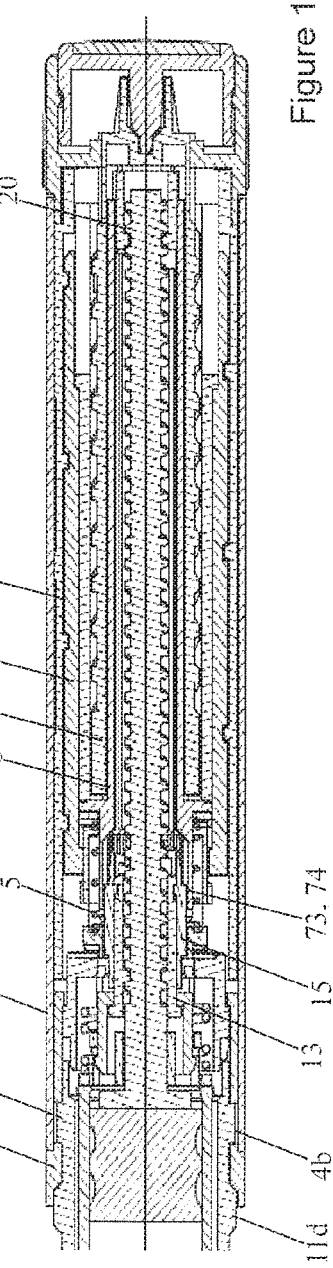

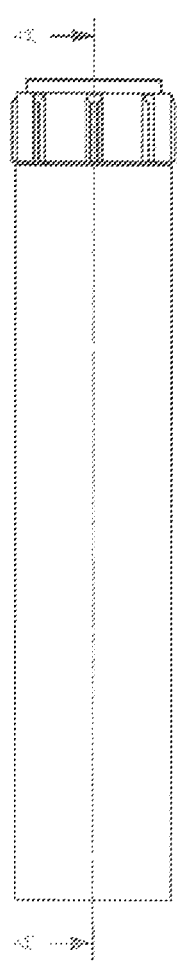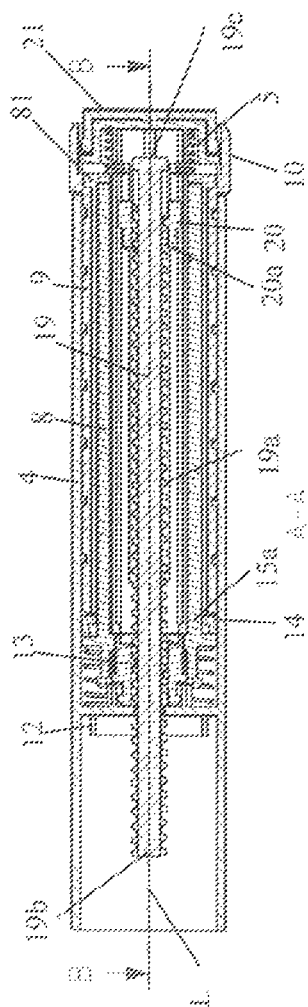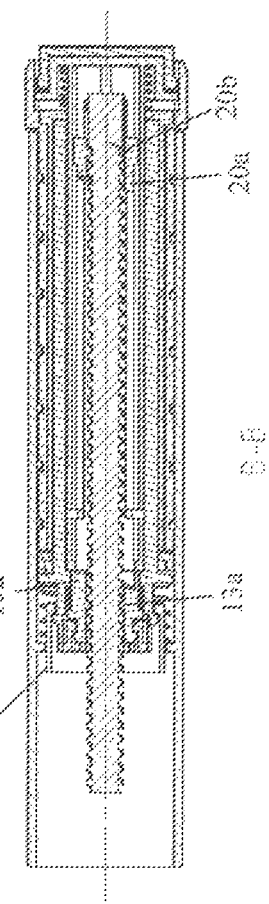

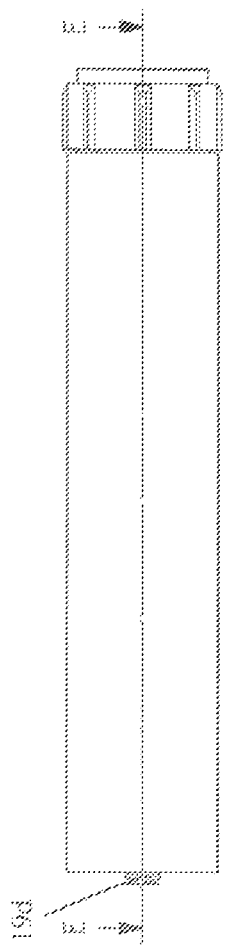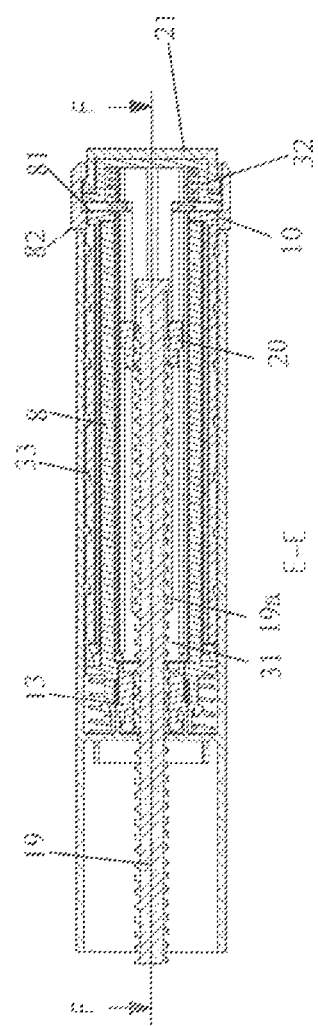
Figure 14a
Figure 14b
Figure 14c

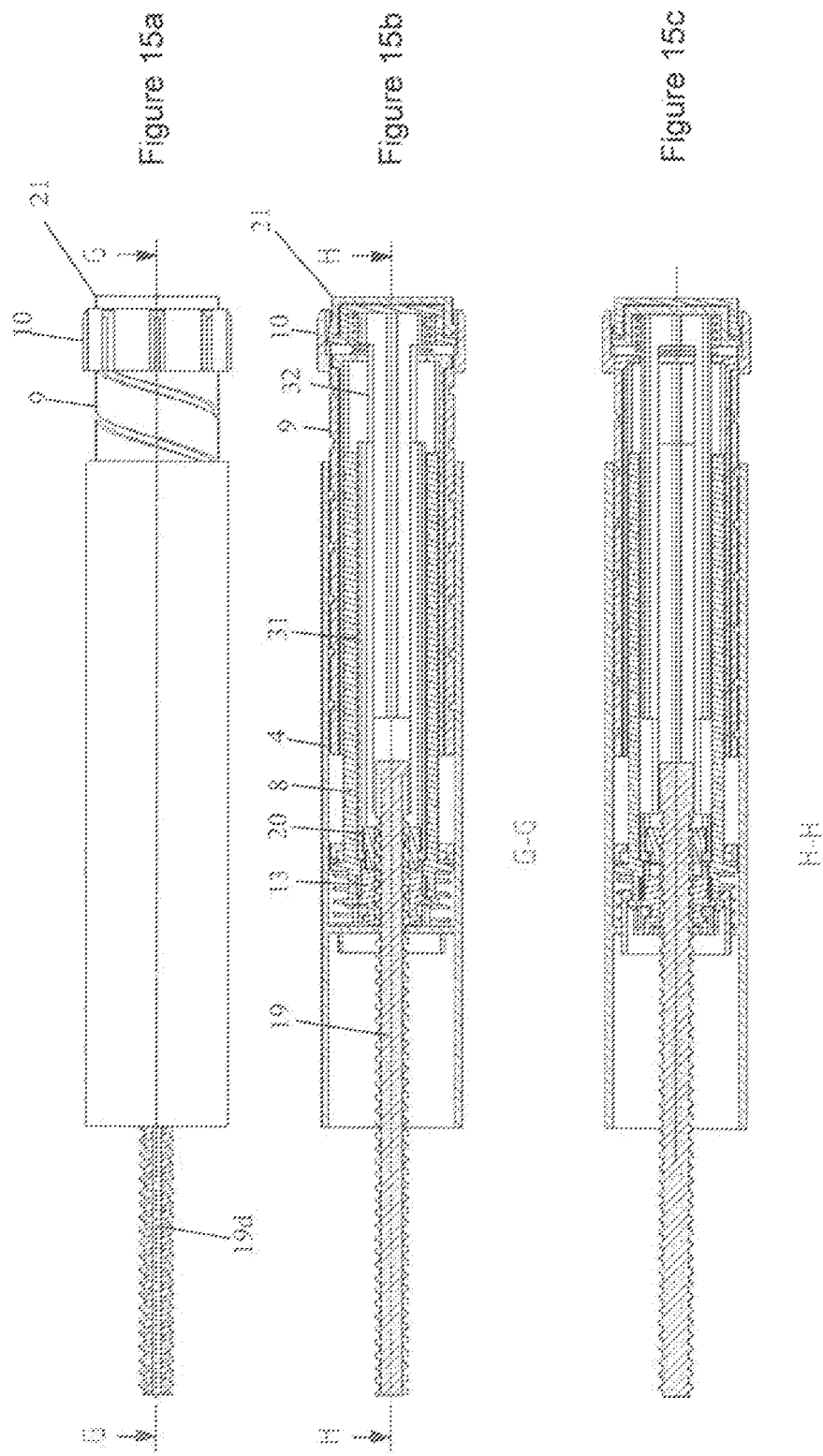

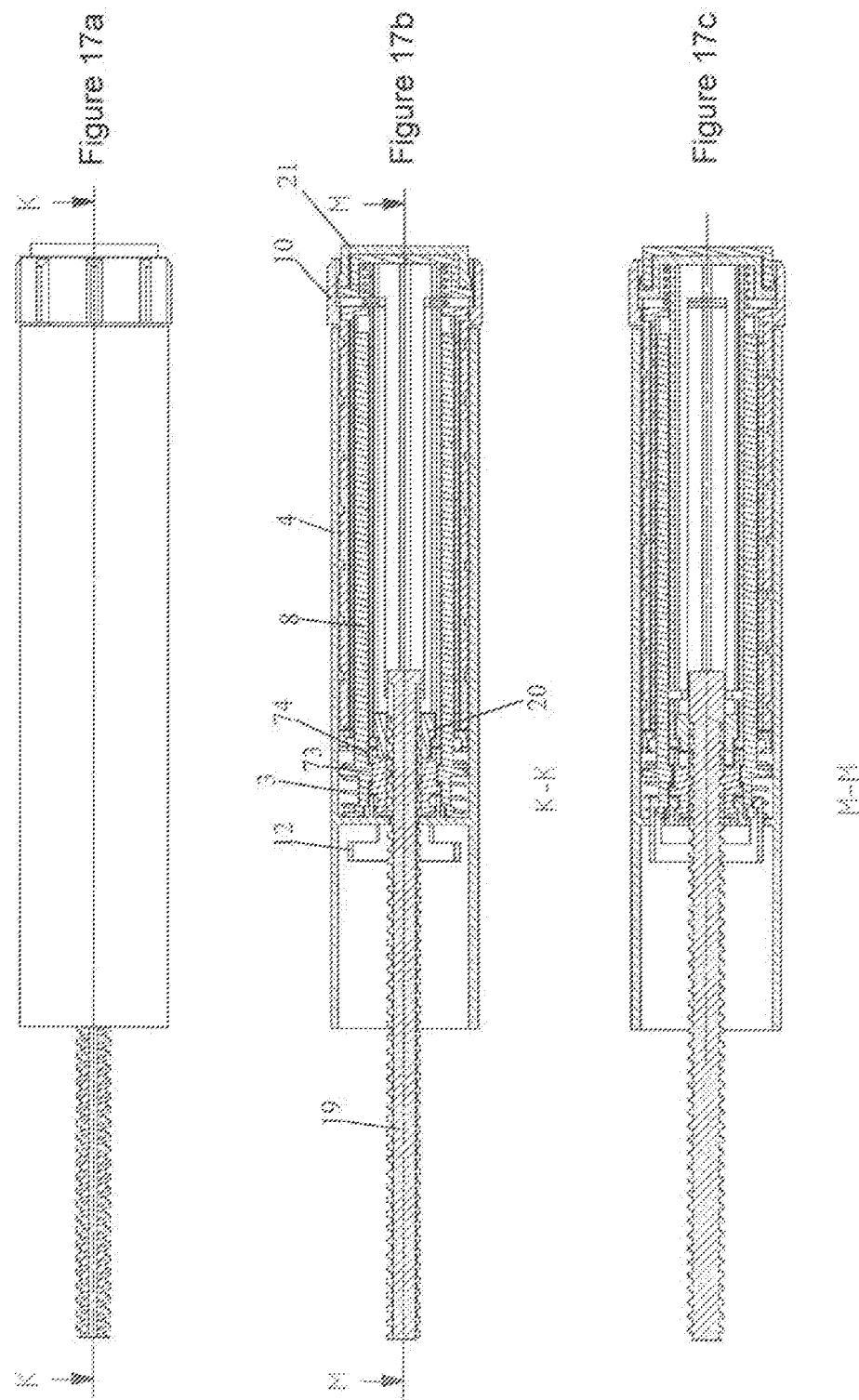

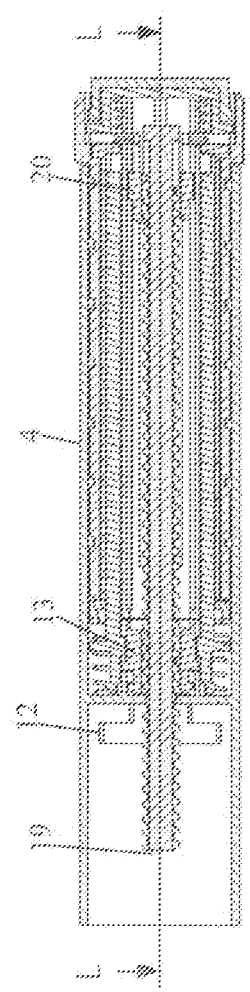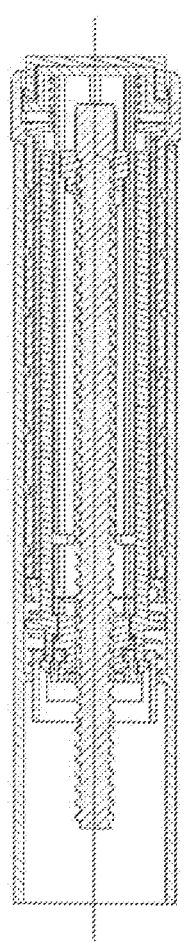
Figure 18a
Figure 18b
Figure 18c

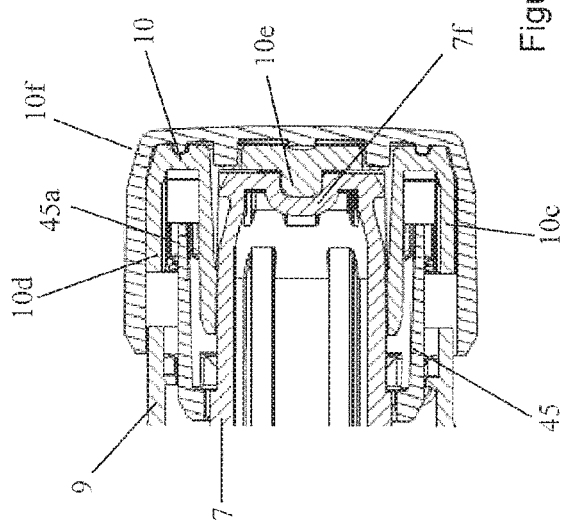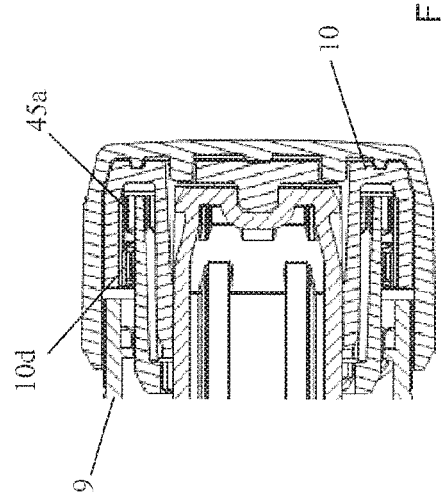

DRIVE AND DOSING DEVICE WITH A STOP ELEMENT FOR PREVENTING THE SETTING OF A DOSE

CROSS-REFERENCE TO RELATED APPLICATION

This application is a continuation of International Patent Application No. PCT/CH2014/000090 filed Jul. 1, 2014, which claims priority to European Patent Application No. 13177387.1 filed Jul. 22, 2013, the entire contents of each are incorporated herein by reference for any and all purposes.

BACKGROUND

Disclosed embodiments relate to drive and dosing devices for an injection device having a mechanism for preventing the setting of a dose which exceeds the amount of product present in a cartridge. The drive and dosing device serves the purpose of dispensing a fluid product, particularly a medicament.

The term "medicament" includes any flowable medical formulation suitable for controlled administration though, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

Injection devices such as injection pens are known from the state of the art. Individual doses of a product can be set and subsequently dispensed with such injection devices. This procedure can be repeated several times. Because the amount of medicament present in the cartridge is limited, namely often 300 International Units (IU), a dose may be set above the amount that can be dispensed from the cartridge, particularly the nominal volume, which is also called the in the cartridge contained volume. This could result in, for example, 35 IU being set while only 20 IU can be dispensed with a subsequent injection. The difference of 15 IU is missing in the medication. A user of the device might not notice this which can lead to hazardous adverse dosing.

From the state of the art other dosing devices are proposed which prevent setting a dose which exceeds the amount of product present in the cartridge. For example, in FIG. 3 of WO 2001/019434, a device is proposed having a drive sleeve surrounding a piston rod having at its outer surface a thread engaging an inner thread of a stop nut. The stop nut has a recess and a sleeve surrounding the stop nut such that the stop nut is in a rotational secure and axially slidable engagement with the sleeve. If the outer sleeve is rotated relative to the drive sleeve, which happens during dose setting, then the stop nut co-rotates and screws itself along the thread of the drive sleeve towards a stop position. During dose delivery, the stop nut stands still with respect to the drive sleeve and the outer sleeve thus building a counting mechanism counting the set and dispensed doses. At the attempt of setting a dose which exceeds the amount of product present in the cartridge, the stop nut abuts a catch on the drive sleeve and blocks a further increase of dose setting such that the setting of a dose exceeding the amount present in the cartridge is prevented.

An alternative example device with an identical effect is shown in WO 2007/017052. Amongst other features, a stop nut is described that is in a threaded engagement with an outer thread present at a piston rod. The piston rod is rotatable with respect to the housing for dispensing a set dose and is also in a threaded engagement with the housing such that a rotation of the piston rod causes the piston rod to move in the dispensing direction. During setting of a dose which would exceed the amount of product present in the cartridge, the stop nut hits a mechanical stop present at the proximal end of the piston rod whereby the mechanism is blocked, and the setting of a dose exceeding the amount present in the cartridge is prevented.

In WO 2005/018721, an injection device is described having a dose knob that can be rotated relative to a housing for setting a dose and that rotation is transmitted to a dose setting member or scale drum. During dispensing, the dose knob is rotationally decoupled from the scale drum. Thus, during dose delivery the knob is pressed with the thumb and this knob does not rotate relative to the housing versus the scale drum that rotates back into the device.

In WO 2004/020027 an injection device is described having a dose knob for setting a dose and an overload protection for the dose setting mechanics. For example, if a user wants to over-torque the dose knob when the rotation is in principle blocked by the dose setting mechanics, thus preventing damage to the mechanical components of the system.

SUMMARY

Disclosed embodiments may provide an alternative drive and dosing device for an injection device compared to the above mentioned mechanisms. Embodiments may also provide a drive and dosing mechanism with improved drive efficiency and improved device handling for the user. Embodiments may reduce the size and complexity of the device.

These objects are solved with, for example, a drive and dosing device according to claim 1. Preferred embodiments are specified in the dependent claims, the description and the figures.

In an example, the drive and dosing device has a housing, such as a single-part or multi-part housing. The housing can, for example, have an elongated shape. The housing can have, for example, a sleeve shape or exhibit one or more sleeves which, for example, can be concentrically arranged. The housing can have an outer sleeve which can be held by the user of the device.

The housing can, for example, have an inner sleeve, often called the mechanics holder, which is rotationally and preferably axially connected to the outer sleeve, such as through a snap-fit mechanism or a glue or welding connection. The housing can, for example, have a display, such as a viewing window for reading the current dose setting. The viewing window can, for example, be made from a transparent material, such as a lens. The viewing window may be defined by only a cut-out in the housing.

A sleeve shaped cartridge holder is or can be removable or permanently attached to the distal end of the housing. A cartridge (e.g., an ampoule) is held or can be held by the cartridge holder.

The device also encompasses a piston rod with a distal end, a proximal end and a thread, preferably an outer thread and which can be moved with respect to the housing towards the dispensing direction. The thread is located between the distal end and the proximal end. At the distal end of the piston rod can be arranged, for example, a saucer-shaped flange that pushes against, and can move a plug present in the cartridge that is attached or can be attached to the drive and dosing device. The piston rod is, with respect to the housing, preferably moveable in the dispensing direction and rotationally fixed. The piston rod can be rotationally secured by the housing or by a guiding member that is rotationally secure connected to the housing. The guiding member can be rotationally secured with respect to the housing, whereby the piston rod is also rotationally-secure with respect to and mounted to the guiding member. Preferably, the piston rod is axially (e.g., along the longitudinal axis of the device) slidable relative to the guiding member. The piston rod can, for example, have a non-circular cross section. In particular, the piston rod can have one or more notches (e.g., two) or flattened surfaces that extend along the longitudinal axis of the piston rod and engage the guiding member such that the piston rod is axially slidable and rotationally locked. The guiding member can be, for example, axially locked and slidable with respect to the housing. The guiding member can be a part of the housing or is a separate part, particularly when the guiding member is axially moveable along the longitudinal axis and relative to the housing. If the guiding member is rotationally and axially secured with respect to the housing, then, in particular, it can be considered to be part of the housing.

Furthermore, the drive and dosing device has a rotation member which engages the thread of the piston rod and which is operatively, particularly torque-proof connected with a stop limiter. A rotation of the rotation member relative to the piston rod ensures that the piston rod moves relative to the housing in the dispensing direction along the longitudinal axis of the device. The rotation member can, with respect to the housing be axially locked or only restricted axially moveable. The piston rod is screwed in the distal direction by rotation of the rotating member with respect to the housing. In particular, there may be a screw type of motion between the rotation member and the piston rod, and the piston rod is guided by the housing or the guiding member such that the piston rod axially slides in the dispensing direction (e.g., along a dispensing distance), and is, for example, rotationally locked with respect to the housing.

Further, a dose setting member is provided that is rotatable in a first rotation direction versus the housing and/or piston rod for increasing a dose that can be dispensed from the cartridge. The dose setting member can, in particular during the dose setting and dispensing, be axially locked with respect to the housing. However, preferably, the dose setting member is screwable with respect to the housing such that the dose setting member can be rotated out of the housing by a rotation in the first direction and can be rotated back into the housing by a rotation in the opposite direction (e.g., the second direction). Preferably, the dose setting member is arranged at the proximal end of the housing and can be rotated out of the proximal end of the housing and can be rotated into the proximal end of the housing. Preferably, the dose setting member can be rotated into the housing or at least in the second rotation direction for decreasing a dose that can be dispensed and/or dispensing a dose. A dose correction or reduction of a dose can be done by rotation of the dose setting member in the second rotation direction. Preferably, the dose setting member can be held by the user of the device and can be rotated relative to the housing. The dose setting member can also be designated as a dose knob.

The drive and dosing device further comprises a stop element which has a thread engaging a further thread of the piston rod or the thread engaging the rotation member. The dose knob is connected with the stop element such that a rotation of the dose knob relative to the piston rod and/or housing in the first direction results in a rotation of the stop element relative to the piston rod, preferably in the same direction as for the dose knob. The stop element can be screwed towards the distal end of the piston rod by rotation of the dose knob and/or the stop element, particularly in the first rotation direction. The stop element has a catch which through rotation of the dose knob in the first direction moves towards the stop limiter or a stop position. The distance between the stop limiter and the catch, measured along a helix-shaped curve corresponding to the thread engaging the stop element, is proportional to the volume, particularly either the nominal volume or the dispensable volume in the cartridge. This distance is reduced by rotation of the dose knob in the first direction. If the catch abuts the stop limiter, then the stop element blocks the setting of a dose, for example, which would exceed the amount of product present in the cartridge or—in other words—blocks the rotation of the of the dose knob in the first direction. Thereby the setting of a dose is prevented which would exceed the amount of product present in the cartridge (e.g. the nominal volume). Further, when a higher dose could be set with the drive and dosing device, a value of the dose scale can be read in the viewing window that is below the maximum value of the dose scale. Alternatively the setting of a dose can be prevented which would result in less than the residual volume of the nominal volume remaining in the cartridge or that dispensing would result in dispensing at least a part of the residual volume, particularly if with the drive and dosing device in principle a higher dose could be set, respectively, when in the viewing window a value of the dose scale can be read which is below the maximum value of the dose scale. In particular, a further aspect described below is referenced. The set dose or the in-the-cartridge-available-dispensable dose can be read from the scale drum via the viewing window. Thereby, the user is reliably notified which dose he can safely administer to himself with the device.

An extremely stable mechanism is achieved by the stop element abutting the stop limiter which is rotationally secured with the rotation member. This is because the parts of rotation member, piston rod and stop element are locked with respect to each other when the catch abuts the stop limiter (e.g., when the stop element is in its stop position).

More preferably, the rotation member features the stop limiter. The rotation member can be single part or multi-part. If the rotation member is multi-part, then it is preferred that the parts forming the rotation member are tightly connected to each other and/or behave as a single part. The advantage of a multi-part rotation member is that one part can be made from a first polymer and the other part can be made from a second polymer which is different from the first polymer (e.g., it possesses other properties). For example, the part which is in a threaded engagement with the piston rod can have optimized frictional properties (e.g., building a low friction bearing couple with the piston rod). The other part which, for example, can feature the stop limiter, can be optimized with respect to mechanical strength (e.g., it is made from a fiber reinforced polymer). The latter part can, for example, exhibit one or more coupling structures like, for example a tooth system or teeth (e.g., toothing). In particular for the coupling structures it is advantageous to keep an eye on an increased mechanical strength.

In preferred embodiments, the dose knob is rotatable in the second direction, which is opposite to the first rotation direction, for decreasing the set dose. The rotation of the dose knob relative to the piston rod in the second rotation direction can result in a rotation of the stop element relative to the piston rod, preferably also in the second rotation direction. As a result of this rotation, the stop element can be screwed towards the proximal end of the piston rod. Thereby, the stop element is preferably also moved along the longitudinal axis of the housing. Particularly, by the rotation of the dose knob and/or stop element relative to the piston rod it is achieved that the catch moves away from the stop limiter (e.g., the distance between the catch and the stop limiter increases).

The drive and dosing device comprises an actuation member, which is actuated (preferably pushed) by a user of the device for the dispensing of a set dose. The actuation member is preferably located at the proximal end of the drive and dosing device. Particularly during actuation, the actuation member can be moved along the longitudinal axis and/or in the distal direction. The actuation member can be held by the dose knob. As an example, the actuation member can be the proximal end of the drive and dosing device. The actuation member can be particularly shaped as the dose button. The actuation member is advantageously located such that the user of the device can actuate (preferably push) the actuation member with the thumb of the hand holding the drive and dosing device. The actuation member can be pushed relative to the housing and/or dose knob into the distal direction from a non-actuated position in an actuated position. Preferably there is a spring which is stressed during actuation of the actuation member. If the actuation member is released, then the actuation member can move from the actuated position into the non-actuated position, preferably through the pre-stressed spring.

In embodiments whereby the dose knob is rotated out of the proximal end of the housing for increasing a dose, it is preferred that pushing the actuation member at first initiates a distal movement of the actuation member relative to the dose knob (actuation distance of the actuation member), whereby a further pushing of the actuation member causes the dose knob to screw back into the housing (e.g., by the dose setting distance of the dose knob).

Pressing the actuation member over the dose setting distance by a user ensures that the rotation member is rotated with respect to the housing and piston rod (preferably in the second direction), whereby the piston rod moves relative to the housing in the dispensing direction. The stop element is screwed at the same time towards the proximal end of the piston rod whereby the distance between the stop limiter and the catch ideally remains constant. The described effects are the result of the dose knob that screws back into the housing whereby the rotation member rotates relative to the housing and the piston rod, particularly, in the second direction. During this movement (e.g., during dispensing) the stop element is axially immovable with respect to the housing and rotates in the second rotation direction. Thereby it is achieved, that the distance between the stop limiter and the catch remains constant, but the stop element screws in the proximal direction with respect to the piston rod because the piston rod does not perform a rotational movement during the dose dispensing and instead performs an axial movement.

In the above described embodiment, the actuation member (or dose button) and dose setting member (or dose knob) are designed as two separate parts and actuation of the dose button by the user of the device and further pushing of the dose button ensures that the dose setting member is rotated back into the proximal end of the housing. The user grips the housing in his hand and pushes with his thumb the dose button together with the dose knob back into the housing. Thereby the dose knob preferably rotates in the second direction whereas the dose button is rotationally secured by the thumb of the user. The rotation of the two parts versus each other during dose dispensing might be impaired by the user's thumb pushing the non-rotating dose button and also touching the rotating dose knob. Therefore the device may be designed such that the functionalities of the dose button for dose dispensing and the dose knob for dose setting are combined as a single part for the user. For example, during dose setting the user rotates the combined button for setting a dose and during dose delivery he or she pushes the combined button for dispensing the set dose and the combined button does not rotate during dispensing. Thus the two functionalities of dose setting and dose delivery can be activated by two separate parts or one single part. Such a combined dose setting and dose delivery button is known from the art (see, e.g., Eli Lilly's Kwikpen; see also WO 2005/018721).

As mentioned above, the driving mechanism has a stop element which prevents setting a dose which would exceed the amount of product present in the cartridge when the stop element is in the stop position (e.g., when the catch of the stop element abuts the stop limiter). In that situation, a user cannot set a higher dose by rotating the dose knob in the first rotation direction and the torque is transmitted from the dose knob via the catch to the stop limiter. To prevent over-torqueing of the drive and dosing mechanism which could damage the assembly of stop limiter, catch, stop element or other drive components of the mechanism, it can be advantageous to provide a unidirectional overload protection mechanism between the dose setting mechanism and the drive mechanism. Such an overload protection can be designed, for example as an overload clutch, as a unidirectional ratchet system, a predetermined breaking point or any other coupling system having an upper torque limit before decoupling the coupling. In case the users attempts to rotate the dose knob in the first rotation direction when the stop element is in the stop position, the overload protection is activated before the parts of the drive mechanism are mechanically damaged. Alternatively or additionally, such an overload protection can protect the drive mechanism or stop limiting the setting of each individual dose (e.g., the stop zero dose and/or the stop maximum dose). In that case a bidirectional overload protection may be used. The overload protection mechanism is located between the dose knob and the rotation member, for example between the dose knob and an intermediate sleeve such as, for example, the drive sleeve, dose sleeve or coupling sleeve (described below), preferably between the dose knob and the scale drum. As mentioned above, the dose knob and dose button can be designed as two separate parts of as one single part. In the case the dose knob and dose button are constructed as two separate parts, then the overload protection mechanism can also be located between the dose knob and the dose button. The overload protection can be a reversible or an irreversible system and the activation of the system can be notified to the user by an audible, tactile or visible indicator. Thereby the user is notified that he or she uses excessive torque on the system, while at the same time protecting the drive mechanism by only allowing a preset threshold torque value to be transmitted to the drive and dosing mechanism. As mentioned before, the Eli Lilly Kwikpen (see, e.g., WO 2005/018721) already has the feature of a combined dose setting/delivery button but does not have the overload protection mechanism for the dose setting member. An overload protection has been disclosed in WO 2004/020027 but this publication does not disclose the overload protection in combination with a combined dose knob. In WO 2004/020027 an overload protection is disclosed to protect the dose setting mechanics from overloading but lacks the feature of the combined dose knob of the present embodiments. Disclosed embodiments minimize the number of parts (and therefore the cost) and/or complexity of the device by combining the overload protection and the combined dose knob in a single part, an overload clutch. Thus the overload protection of an embodiment is active when the dose knob is in the non-actuated position and the overload protection is non-active when the dose knob is in the actuated position.

A drive and dosing mechanism is described for a reusable or disposable injection device comprising a tubular housing, a piston rod having a thread and which is moveable in a dispensing direction with respect to the housing for dispensing a product, a rotation member, a scale drum and a dose knob. The rotation member can be engaged with the thread of the piston rod whereby a rotation of the rotation member in the second direction relative to the piston rod ensures that the piston is moved relative to the housing in the dispensing direction. The scale drum having a helical shaped dose scale on its surface and the housing has a region for viewing the dose scale, particularly a viewing window, for reading the value of the dose scale corresponding to the set dose. The dose knob present at the proximal end of the housing can be rotated during dose setting in a first direction or in a second direction which is opposite to the first direction, whereby during dose setting, when the dose knob is not actuated, the dose knob is rotationally coupled to the scale drum and a rotation of the dose knob is transferred to the scale drum which performs a screw type of movement relative to the housing such that the helical shaped dose scale moves along the viewing window. The dose knob is actuated during dose delivery, and the dose knob is rotationally decoupled from the scale drum, and the dose knob and scale drum move together in the distal direction, and the scale drum rotates in the second direction without a rotation of the dose knob, whereby the rotation of the scale drum in the second direction is transferred to the rotation member and the piston rod is moved in the dispensing direction for dispensing the product from the cartridge.

The dose knob is moved in the distal direction with respect to the scale drum without rotation during actuation of the dose knob. The scale drum does not move in the distal direction or rotate with respect to the housing during actuation of the dose knob. A sleeve shaped overload clutch can be present between the dose knob and the scale drum, the overload clutch being connected to the scale drum and the dose knob being axially slidable with respect to the overload clutch. The overload clutch can have a coupling structure, preferably teeth, circumferentially arranged on the outside surface which can engage a circumferentially arranged coupling structure, preferably teeth present at the inside of the dose knob. The two coupling structures are arranged such that they can slide versus each other along the longitudinal axis of the drive and dosing mechanism. The two coupling structures being coupled when the dose knob is not actuated and the two coupling structures being decoupled when the dose knob is actuated. One or both of the coupling structures can be present on a resilient member and the coupling structures are shaped such that they provide either a unidirectional or a bidirectional ratchet coupling. During dose setting, the dose knob is rotated and the rotational forces of the dose knob are transmitted to the scale drum via the ratchet coupling with the engaging teeth of the two coupling structures. The ratchet coupling is activated (e.g., the two coupling structures start to ratchet in the circumferential direction) when the scale drum is in the maximum dose or minimum dose position and the user attempts to set a higher respectively lower dose. For this purpose a bidirectional coupling is required. When the user attempts to set a dose which exceeds the amount of medication present in the cartridge (e.g., when the stop element is in the stop position) the setting of that dose is prevented. A unidirectional ratchet coupling present between the dose knob and the scale drum can prevent damage to the drive and dosing mechanism. Thus a bidirectional coupling protects the stop zero dose, stop maximum (individual) dose and stop total dose mechanisms (preventing the setting of a dose exceeding the amount present in the cartridge). A unidirectional coupling is used for the stop maximum (individual) dose and stop total dose mechanisms.

Preferably, a unidirectional coupling (preferably a ratchet) is located between the housing and the rotation member, which permits a rotation of the rotation member in a rotation direction (preferably in the second rotation direction) and which does not permit a rotation in the opposite direction (preferably the first rotation direction). For example, the unidirectional coupling may utilize a low torque, thus elastically deforming a resilient or elastic element (spring or retaining ratchet) of the unidirectional coupling resulting in a movement of the piston rod in the dispensing direction. Advantageously it can be achieved through this arrangement that upon trying to rotate the dose knob in the first direction, the rotation in the first direction is prevented when a catch abuts a stop limiter (e.g., when the stop element is in the stop position). Preferably, the torque executed in the first rotation direction on the dose knob is transmitted from the stop element to the rotation member and from the rotation member via the unidirectional coupling to the housing whereby a rotation of the dose knob in the first direction is prevented when the stop element is in its stop position. As an option, the overload protection described above can be added to the system thus protecting the components of the drive mechanism when the torque is transmitted to the housing.

The unidirectional coupling between the housing and the rotation member allows for a rotation of the rotation member in the second direction for dispensing a dose and is preferably designed as a ratchet system. Such a ratchet system can, for example, be composed of meshing teeth present on two separate parts that are biased by an elastic member such as a spring. The meshing teeth have a steep and flat slope and allow for a rotation in one direction only thereby generating clicks when the teeth ratchet versus each other. Thus on one hand the rotation of the rotation member in the first rotation direction is prevented whereas the rotation in the second direction during dose dispensing is allowed and thereby producing audible and/or tactile signals. The ratchet system absorbs a part of the energy provided by the drive mechanism and therefore affects the drive efficiency of the device. The latter is defined as the ratio of the out coming force acting on plug of the carpule by the piston rod and the incoming force from pushing the dose button or dose knob for dose delivery. The incoming axial forces are translated into rotational movements and the losses in the system define to what extend the incoming force will be transmitted to the plug of the carpule. For example the unidirectional ratchet system absorbs rotational moments for producing the clicks and has frictional losses that can be reduced for optimizing the device efficiency. Parameters for optimizing the efficacy are, for example the number of meshing teeth, slopes of the meshing teeth, radius of the ratchet system, height of the meshing teeth, materials used and, preferably, the biasing force for the ratchet system. The biasing force can be provided by flexible arms or a spring member and the biasing force can be optimized for the clicker functionality only. Frictional losses are proportional to the normal force acting on the meshing teeth of the ratchet system and therefore a higher force leads to higher frictional and/or moment losses. On the other hand a normal force which is too low prevents efficient clicking or adversely affects the unidirectional coupling features that the ratchet system may have as well. Therefore there is an optimum region for the normal force that enables all functionalities of the ratchet system. The drive and dosing device of disclosed embodiments can have improved device efficiency and for that not only the unidirectional ratchet system for dose dispensing needs to be optimized. In the exemplary embodiments presented below the unidirectional ratchet system for dispensing and the ratchet system for dose setting can be powered by a single spring element or each system is powered by a separate spring, which is adjusted to its specific needs. Using one spring unit has the advantage that only one part is needed but on the other hand needs to compromise the spring forces for both ratchet systems. Using two or more springs has the advantage that the spring forces are adjusted to the specific needs and can optimize the device efficiency but this calls, on the other hand, for two instead of one spring units.

A drive and dosing mechanism for an injection device is described whereby a cartridge containing a fluid product is attached or can be attached to the drive and dosing device comprising a tubular housing, a piston rod, a dose knob and a drive nut. The tubular housing having a distal end and a proximal end and the piston rod having an outer thread and being moveable in the distal direction with respect to the housing for dispensing the product. The dose knob can be present at the proximal end of the housing and can be rotated during dose setting in a first direction or in a second direction which is opposite to the first direction. The drive nut has an inner thread that engages the outer thread of the piston rod and which is rotatable in a second direction for dispensing the product. Whereby during dose setting the dose knob is rotated in the first direction out of the proximal end of the housing and a first ratchet system is coupled to the dose knob and ensures that the dose knob can be rotated over discrete angular steps thereby producing dose setting clicks, the ratchet system being biased by a first spring element. The dose knob can be moved back and forth from a non-actuated position to an actuated position over an actuation distance against the resilient force of the first spring element. Whereby during dose delivery the dose knob is actuated thereby decoupling the first ratchet system from the dose knob and coupling the drive nut to the dose knob and the dose knob is rotated in the second direction back into the proximal end of the housing whereby the rotation of the drive nut is translated in a distal movement of the piston rod. Whereby a second ratchet system is coupled to the dose knob producing dose delivery clicks, the second ratchet system being biased by a second spring element. For the two ratchet systems, the ratio of the spring forces of the first and second spring element is above unity.

Particularly in embodiments where a used (e.g., empty) cartridge can be replaced by a new (e.g., filled) cartridge it is advantageous that the unidirectional coupling can be switched back and forth between an activated state and a non-activated state. The unidirectional coupling, in its activated state, allows a rotation of the rotation member in that rotation direction which enables the movement of the piston rod in the dispensing direction, particularly the second rotation direction, and prevents a rotation in the opposite direction, preferably the first rotation direction. The unidirectional coupling, in its non-activated state allows a rotation of the rotation member in the opposite direction, particularly the first rotation direction. The unidirectional coupling preferably takes its non-actuated position when the cartridge holder is released from the housing or is attached to the housing but does not contain a cartridge. The unidirectional coupling can be in its actuated state when the cartridge holder is attached to the housing with or without a cartridge. Two different embodiments arise here from, namely one embodiment where the cartridge holder activates a mechanism switching the unidirectional coupling in its activated state or another embodiment where the cartridge activates this mechanism.

Notably, a switching element can be positioned between the cartridge or cartridge holder and the unidirectional coupling which, through attachment of the cartridge holder, with or without a cartridge, is moveable relative to the housing, particularly in the proximal direction and which switches the unidirectional coupling in its activated state.

The switching element can, by releasing the cartridge holder or cartridge, be moved or is moveable in the distal direction and switch the unidirectional coupling in its non-activated state. Preferably, a spring is used which is tensioned by the movement of the switching element in the proximal direction and which moves the switching element in the distal direction when the cartridge holder or cartridge is removed.

The switching element can, for example, be arranged such that it is rotationally locked with respect to the housing but axially slidable along its longitudinal axis. For example, the cartridge holder can be attached to the housing with a rotational movement. The cartridge holder can have a drive surface, which functions as an activation element, which slides along the switching element upon rotation of the cartridge holder relative to the housing or the switching element, and which provokes a movement of the switching element along the longitudinal axis of the housing. The cartridge holder can, for example, be attached to the housing using a screw thread. Alternatively, the cartridge holder can be attached to the housing using a bayonet lock. The advantage of a bayonet lock is that it generally attaches the cartridge holder to the housing with a rotation that is less than a full rotation relative to the housing for example over an angle of 35°, 45° or 90°, preferably below or equal to 90°. The bayonet lock can be such that, relative to the housing, initially a pure axial movement and subsequently a pure rotational movement are needed for the attachment of the cartridge holder to the housing. Alternatively, the bayonet lock can be shaped such that the cartridge holder executes a concurrent combined axial and rotational movement relative to the housing for the attachment of the cartridge holder. More preferably, the bayonet lock is shaped such that the cartridge holder performs at the end of the connection a pure rotational movement, this means without a movement of the cartridge holder along the longitudinal axis of the housing.

For embodiments where the used cartridge can be exchanged by a new one, it is preferred that the piston rod can be reset (e.g., can be pushed back into the housing of the drive and dosing device, preferably into the proximal direction). During reset, the piston rod is moved relative to the housing in the proximal direction. This can be done by pushing against the distal end of the piston rod, for example with a finger of a user or a plug in a new cartridge, provided that the cartridge holder or cartridge is released, particularly when the unidirectional coupling is not activated. For this purpose it is preferred that the pitch of the meshing threads of the rotation member and the piston rod is high enough to prevent self-locking when the piston rod is reset against the dispensing direction when the unidirectional coupling is not activated. During the reset or movement of the piston rod in the proximal direction, the rotation member rotates in that direction that is opposite to the rotation direction for dose dispensing. Particularly, during reset, the rotation member performs a rotation in the first direction with respect to the housing and/or piston rod. The piston rod is, preferably via the linear slide, rotationally locked relative to the housing during reset of the piston rod.

The drive and dosing mechanism can be configured to automatically retract and/or advance the piston rod during reset of the device (e.g., when an empty cartridge is replaced by a full cartridge). The automatic retraction of the piston rod into the housing facilitates the insertion of a full cartridge and the plug of the cartridge is not exposed to axial forces because the proximal end of the plug will not touch the distal end of the piston rod during insertion of the new cartridge. Such a retraction mechanism can comprise a resilient member attached to and present around, on or inside the piston rod such as a spring (e.g., compression or spiral) or a magnetic member or electromagnetic member. Such a resilient member is tensioned during advancement of the piston rod and energy stored in the member is released during reset of the device to retract the piston rod. The automatic advancement of the piston rod after reset (e.g., when a new cartridge has been inserted) prevents an air gap from being present between the distal end of the piston rod and the proximal end of the plug of the cartridge. This will facilitate the priming operation needed before setting and dispensing of a dose since no air gap needs to be closed before dispensing the first dose. The advancement of the piston rod can comprise a resilient member such as a compression or spiral spring, or a magnetic or electromagnetic arrangement.

Notably during reset of the piston rod, the stop element is axially and rotationally locked with respect to the piston rod such that the stop element moves together with the piston rod relative to the housing in the proximal direction.

The dose knob may be configured to not perform a rotational or axial movement relative to the housing during reset of the piston rod.

In preferred embodiments, where the set dose may be easily readable, the drive and dosing device has a scale drum that is directly or indirectly at least rotationally locked, preferably also axially locked to the dose knob. In more preferred embodiments, the scale drum and the dose knob are connected as a single part or they are snapped, glued or welded together. Particularly, the dose knob and the scale drum can behave as a joint part. The scale drum can have a helical shaped dose scale arranged preferably at its outer surface. The dose scale encompasses preferably a plurality of individual dose values or at least symbols that represent a specific dose whereby the values or symbols are arranged along a helical curve such that it results in a helical dose scale. The dose scale can have values of, for example 0 IU to 60 IU or 80 IU or even more than 100 IU, stepped in 1, 2, 5 or other units. As mentioned before, the housing can have a region for viewing the set dose, preferably a viewing window, where the value or symbol of the dose scale can be read which represents the current or actual set dose or the dose to be dispensed. The scale drum performs, via a rotation of the dose knob, a screw type of motion relative to the housing such that the value of the helical shaped scale moves along or through the region for viewing the set dose.

In an example, the scale drum has a thread which preferably has the same pitch as the helical shaped dose scale, whereby the thread can be in a threaded engagement with the housing. The housing can, for example, have an inner thread and the scale drum an outer thread. Alternatively, the scale drum can have an inner thread and the housing can have an outer thread for the threaded engagement. The pitch of the thread or the threaded engagement is preferably such that no self-locking occurs when the actuation member is actuated for the dispensing of a product, respectively is pushed in the distal direction along the propulsion distance into the housing, such that the dose knob is screwed together with the scale drum into the housing. Thus the scale drum performs via the threaded engagement (e.g., with the housing) a translational movement with respect to the housing during dose setting and dose correction when the dose knob is rotated in the first or second rotation direction. The distance travelled in the rearward direction depends on the pitch of the thread between the scale drum and the housing, a high pitch implies a higher distance whereas a lower pitch results in a lower distance. Of course there are limits for the pitch, if the pitch is too high, then the user cannot push the dose button with the same hand that holds the housing of the device since the dose knob/button is out of reach. If the pitch is too low then the threading engagement runs into the self-locking region which would prevent rotation of the dose knob back into the device during dose delivery. An additional aspect of the thread pitch of the dose scale is that it contributes to the gearing ratio of the device. When the dose button is actuated and pushed back into the proximal end of the housing, the dose knob is rotating and this rotation is translated to a rotation of the rotation member and finally into a distal movement of the piston rod. The gearing ratio can be defined by the ratio of the pitches of threads of the scale drum (and/or dose sleeve) and the piston rod (and/or rotation member), respectively. Thus, with a constant pitch of the thread of the piston rod, a high pitch of the scale drum results in a high gearing ratio therewith lowering the force for dispensing a product, but this at the cost of a higher distance that needs to be travelled by the dose knob. On the other hand, a lower pitch of the thread of the scale drum lowers the distance that the dose knob needs to travel for delivering a dose but this at cost of a lower gearing ratio or higher forces need to be applied by the user for dispensing a dose. In that context the device efficiency, or reduction of frictional/moment losses are important since in the triangle of gearing ratio, travel distance and device efficiency, it may be advantageous for an embodiment to present a device having a low distance that the dose knob travels, with an low input force of the user and a high output force on the plug of the cartridge.

In more preferred embodiments, the scale drum can be rotated back and forth between a zero dose position and a maximum dose position, whereby a stop zero dose prevents a rotation of the scale drum in the zero dose position in the direction, preferably the second direction, which reduces the dose and which allows for a rotation in the first direction, and whereby a stop maximum dose prevents a rotation of the scale drum in the stop maximum dose position, preferably the first direction which increases the dose and which allows for a rotation in the second direction for reducing a dose. It is preferred that in the viewing window the maximum value of the dose scale can be read when the dose scale is in the maximum dose position and the dose zero can be read when the scale drum is in the zero dose position. The dose set in the maximum dose position is the dose that maximally can be dispensed with a single injection even when more product is available in the cartridge. The stop maximum dose and/or the stop zero dose preferably act in the circumferential direction and can be shaped as an anti-twist type of arrester. Analogously, the same can apply for a maximum dose counter-arrester and/or a zero dose counter-arrester.

In a first alternative, the stop maximum dose and/or the stop zero dose arresters can be established on the housing or an element fixed to the housing which can be considered to be part of the housing like, for example, an insert for the viewing window made from a transparent or opaque material, particularly a plastic material. Preferably the scale drum can establish the maximum dose counter-arrester which in the maximum dose position abuts the stop maximum dose (arrester). The scale drum or the dose knob can establish the zero dose counter-arrester which abuts the stop zero dose (arrester) in the zero dose position.

In a second alternative, the stop maximum dose and/or the stop zero dose (arresters) can be located at, for example an intermediate sleeve, particularly the dose sleeve, which can be located between the dose knob and the stop element and which is rotationally secured with respect to the dose knob. Preferably, the intermediate sleeve, particularly an end of a thread or of a thread element of the intermediate sleeve can establish the stop maximum dose. Alternatively or additionally, the intermediate sleeve, particularly an end of the thread of the intermediate sleeve, particularly the end of the thread or thread element which is opposite to the stop maximum dose, can establish the stop zero dose. Preferably, the stop maximum dose is located distally versus the stop zero dose, or vice versa. The maximum dose counter-stop or counter arrester and/or the zero dose counter-stop or counter arrester can be established by, for example, a coupling member, particularly a coupling sleeve which is in a threaded engagement with the intermediate sleeve, particularly the dose sleeve and which is rotationally secure and axially slidable connected with the scale drum. The coupling member can have an inner thread, particularly a thread segment which engages an outer thread, particularly the thread of the intermediate sleeve which forms at least one out of stop maximum dose and stop zero dose, whereby it is preferred that one end of the thread segment establishes the zero dose counter-stop (arrester) and the other end of the same, or another thread segment, establishes the maximum dose counter-stop (arrester).

The first and second alternatives can be combined. For example, the stop zero dose (arrester) and/or the zero dose counter-stop (counter-arrester) can be established according to the first alternative and the stop maximum dose (arrester) and/or the maximum dose counter-stop (counter-arrester) can be established according to the second alternative. Alternatively, the stop maximum dose (arrester) and/or the maximum dose counter-stop (counter-arrester) can be established according to the first alternative and the stop zero dose (arrester) and/or the zero dose counter-stop (counter-arrester) can be established according to the second alternative.

The catch of the stop element abuts the stop limiter and the stop element prevents rotation of the scale drum in the rotation direction which results in a dose increase, when the scale drum is not in its maximum dose position and/or the amount of product present in the cartridge is below the dose of the maximum dose position of the scale drum.

In other words, the maximum dose can be set and dispensed on the drive and dosing device as often as this maximum dose is actually present as product in the cartridge. If the amount of product present in the cartridge is below the maximum dose, then the stop limiter (arrester) and catch (counter-arrester) collide with each other and as such prevent an increase of the dose setting.

The stop element is, in preferred embodiments, at least during the dose setting and dispensing of the set dose torque-proof coupled to the scale drum and/or dose knob. The coupling can be permanent, particularly in all operating conditions. For example, the stop element can be indirectly coupled to the scale drum and/or dose knob, for example via an intermediate sleeve. As an alternative, the stop element can be directly coupled or engaged with the dose knob or scale drum. Preferably, the scale drum and/or the dose knob are moveable with respect to the stop element along the longitudinal axis of the drive and dosing device.

In preferred embodiments at least one intermediate sleeve (e.g., the drive sleeve and/or the dosing sleeve or a first and second coupling sleeve) can be kinematically located between the dose knob and the stop element. The at least one intermediate sleeve can engage the stop element such that it is axially slidable and rotationally secured. The at least one intermediate sleeve is preferably rotationally secure and optionally axially slidable coupled with the dose knob. This ensures that the rotation of the dose knob is transmitted to the stop element, which is rotated in the same rotation direction as the dose knob.

The stop element is coupled such with the dose knob such that the stop element is screwed along the piston rod during dose setting (e.g., during rotation in the first direction and/or rotation in the second direction and during dispensing of the set dose). Particularly, the stop element is screwed towards the distal end of the piston rod when the dose is increased and it is screwed towards the proximal end of the piston rod when the dose is decreased or dispensed. The mechanical set-up according to disclosed embodiments ensures that in the zero dose position immediately after dispensing of a set dose, the stop element is in the same position with respect to the piston rod as for the zero dose position immediately before setting the dose to be dispensed. For example, the stop element in the zero dose position of the scale drum always occupies the same position with respect to the piston rod independently from the degree of filling of the cartridge or from the dispensing distance of the piston rod. Such a kinematic arrangement allows for a space-saving integration of the stop element in the drive and dosing device.

More preferably, the drive and dosing device has a dispense coupling which is closed upon actuation, preferably pushing, of the actuation member by the user along the actuation distance and which is, or can be, opened by releasing the actuation member. Particularly the spring that is stressed by the actuation of the actuation member and closure of the dispense coupling can open the dispense coupling and reset the actuation member into its original position.

The rotation member is rotationally secured with the scale drum and/or the dose knob when the dispense coupling is coupled and when the actuation member is actuated. The scale drum and/or the dose knob can be rotated relative to the rotation member, when the dispense coupling is open (e.g., when the actuation member is not actuated) or released (e.g., when the actuation member is in its non-actuated position).

The actuation member is not actuated for setting a dose whereby it is actuated for dispensing a dose. This implies that the dispense coupling is closed during the dose dispensing, whereby it is opened during the dose setting. The dispense coupling can, for example, have a first coupling structure and a second coupling structure that engage in a form fit engagement when the dispense coupling is closed and that disengage when the dispense coupling is open. Preferably, the coupling structures can be brought in and out engagement with each other by movements along the longitudinal axis of the drive and dosing device. Provided that the drive and dosing device has at least one intermediate sleeve, one coupling structure can be permanently rotationally locked with the intermediate sleeve (e.g., with a drive sleeve) whereby the other coupling structure can be, for example, located at the rotation member. The coupling structure that can be brought into engagement with the rotation member is preferably permanently rotationally locked with respect to the stop element. Thereby it is ensured that this coupling structure follows the rotational movements of the stop element during dial-up, dial down or dispensing of a dose.

A further aspect applies to the limitation of the dispensable amount from a cartridge. This aspect need not only be applied to the drive and dosing device described here, but also to, for example, mechanisms known from the state of the art for restricting the dose setting as exemplary described in the patent literature cited above. The applicant reserves the option to claim this general aspect with a separate application or at least to pursue with claims directed hereupon.

The solution described in this context, particularly described in claims 16 and 17 is based upon the problem to increase the therapeutic options for injection devices that limit the dose setting in specific situations and to provide for this purpose a simple and cost-efficient solution.

In the state of the art, preventing the setting of a dose which exceeds the amount of product present in the cartridge is suggested. Disclosed embodiments may be used to prevent errors (e.g., inadequate dosing) from occurring when the user attempts to set a dose that cannot be dispensed with the injection device because the amount of product present in the cartridge is not sufficient.

Usually, ampoules are used as cartridges often having a nominal volume of 300 IU. It should be noted that the nominal volume is generally below the total volume of the cartridge. The nominal volume can be dispensed by moving the plug in the cartridge. The difference between the total volume and the nominal volume can be designated as the dead volume which, for example, due to the geometry of the plug and the cartridge housing cannot be dispensed. The cartridges proposed in the state of the art refer, for the blockage of the last dose, to the nominal volume.

In an aspect of disclosed embodiments, it is supposed that from the cartridge of the injection device (e.g., preferably an ampoule) only a first part (e.g., designated as dispensable volume of the nominal volume) can be dispensed from the amount present in the cartridge (e.g., as delivered). A second part, called the residual volume and which is above 1 IU, remains in the cartridge. The residual volume could be dispensed by moving the piston rod, but such a movement is blocked by the injection device. With the injection device, only the dispensable volume of the nominal volume can be dispensed and the residual volume of the nominal volume cannot be dispensed. The total volume in the cartridge is composed of the dead volume and nominal volume. The nominal volume is composed of the dispensable volume and the residual volume.

The injection device further has an elongated and preferably sleeve-shaped housing and a dose knob which can be rotated relative to the housing in a first rotation direction for increasing a dose to be dispensed, and preferably can be rotated in second rotation direction opposite to the first rotation direction for decreasing a dose to be dispensed. For the design of the housing, the dose knob and the scale drum it is referred to the embodiments described herein, independent of the design and integration of the stop element. The same applies to the actuation element.

A stop element, preferably rotationally coupled with the dose knob, performs during a rotation of the dose knob in the first direction (e.g., with an increase of the dose to be dispensed), a movement towards a stop limiter. As a result, the distance, particularly measured along a helix-shaped curve and which is particularly directly proportional to the volume that can be dispensed, is reduced between the stop limiter and the stop element.

The stop element, coupled with the dose knob performs a movement away from a stop limiter during a rotation of the dose knob in the second direction (e.g., with a decrease of the dose to be dispensed). As a result, the distance, particularly measured along a helix-shaped curve and which is particularly directly proportional to the volume that can be dispensed, is increased between the stop limiter and the stop element.

Preferably, the stop element engages a thread, along which it can be screwed during a rotation of the dose knob. The thread preferably provides the helix-shaped curve.

The stop element does not move with respect to the stop limiter during the dispensing of a set dose (e.g., the stop element stands still with respect to the stop limiter), but it can, for example, move with respect to the housing.

The injection device preferably has a dispensing coupling which can be coupled through actuation, preferentially pushing of an actuation element, particularly a dose button (or a combined dose-knob-dose-button as described previously) at the proximal end of the injection device. The dispensing coupling couples the stop limiter and the stop element such that the stop element and the stop limiter are moveable relative to each other when the actuation element is not actuated (e.g., is in its non-actuated position), and the stop element and the stop limiter are non-moveable with respect to each other (particularly rotationally secured) when the actuation element is actuated (e.g., is in its actuated position).

If the stop element abuts the stop limiter, then the setting of a dose that would result in dispensing part of the residual volume is prevented. In other words, the setting of a dose can be prevented which would result in less than the residual volume of the nominal volume remaining in the cartridge. With the device only the dispensable volume and not the residual volume or a part of the residual volume can be dispensed.

Injection devices can be produced cost effectively by changes in the assembly of injection devices described herein and devices known from the state of the art. First, the nominal volume of the cartridge for the injection device is defined. Then the dispensable volume is defined. The injection device is assembled such that only the dispensable volume which is below the nominal volume can be dispensed, and the residual volume of the nominal volume cannot be dispensed. This is done by positioning the stop element at a distance with respect to the stop limiter, the distance being measured along a helical curve whereby the distance is directly proportional to the dispensable volume. For the devices known from the state of the art, this distance is directly proportional to the nominal volume.

BRIEF DESCRIPTION OF THE DRAWINGS

FIG. 1 is an exploded view of the individual parts of a drive and dosing device according to a first embodiment.

FIG. 2a shows a drive and dosing device of the first embodiment in an initial state with a filled cartridge.

FIG. 2b shows a sectional view of the device of FIG. 2a rotated along the longitudinal axis by 90°.

FIG. 3 shows the device of FIGS. 2a and 2b in a maximum dose position and with the dose button in a non-actuated position.

FIG. 4 shows the device of FIG. 3 with an actuated dose button.

FIG. 5 shows the device according to the first embodiment in a zero dose position after the dose set in FIGS. 3 and 4 has been dispensed.

FIG. 8 shows the device according to the first embodiment with the cartridge and the cartridge holder removed from the drive and dosing device.

FIG. 9 shows the drive and dosing device according to the first embodiment after a piston rod has been reset and a new cartridge and a cartridge holder can be connected.

FIG. 10a shows the device according to the first embodiment after a new cartridge is inserted and the dose button is actuated in the zero dose position.

FIG. 10b shows a sectional view of the device of FIG. 10a rotated along the longitudinal axis by 90°.

FIG. 12a shows a drive and dosing device according to the second embodiment in the zero dose position.

FIG. 12b shows a cross sectional view of the drive and dosing device shown in FIG. 12a taken along the line A-A in FIG. 12a.

FIG. 12c shows a cross sectional view of the drive and dosing device shown in FIG. 12a taken along the line B-B in FIG. 12b.

FIG. 13b shows a cross sectional view of the drive and dosing device shown in FIG. 13a taken along the line C-C in FIG. 13a.

FIG. 14a shows the drive and dosing device of FIG. 13a after the dose set in FIG. 13a has been completely dispensed.

FIG. 14b shows a cross sectional view of the drive and dosing device shown in FIG. 14a taken along the line E-E in FIG. 14a.

FIG. 14c shows a cross sectional view of the drive and dosing device shown in FIG. 14a taken along the line F-F in FIG. 14b.

FIG. 15a shows the drive and dosing device of FIG. 12a with the stop element in the stop position.

FIG. 15b shows a cross sectional view of the drive and dosing device shown in FIG. 15a taken along the line G-G in FIG. 15a.

FIG. 15c shows a cross sectional view of the drive and dosing device shown in FIG. 15a taken along the line H-H in FIG. 15b.

FIG. 16b shows a cross sectional view of the drive and dosing device shown in FIG. 16a taken along the line R-R in FIG. 16a.

FIG. 17a shows the drive and dosing device of the second embodiment after unidirectional coupling has been de-activated.

FIG. 17b shows a cross sectional view of the drive and dosing device shown in FIG. 17a taken along the line K-K in FIG. 17a.

FIG. 17c shows a cross sectional view of the drive and dosing device shown in FIG. 17a taken along the line M-M in FIG. 17b.

FIG. 18a shows the drive and dosing device of FIG. 17a after the piston rod has been reset.

FIG. 18b shows a cross sectional view of the drive and dosing device shown in FIG. 18a taken along the line J-J in FIG. 18a.

FIG. 18c shows a cross sectional view of the drive and dosing device shown in FIG. 18a taken along the line L-L in FIG. 18b.

FIG. 25a is a detail cross sectional view of a drive and dosing device according to the third embodiment after setting of a dose and having a non-actuated dose knob.

FIG. 25b is a detail cross sectional view of a drive and dosing device according to the third embodiment, after setting of a dose and having an actuated dose knob.

DETAILED DESCRIPTION

Figure 6:
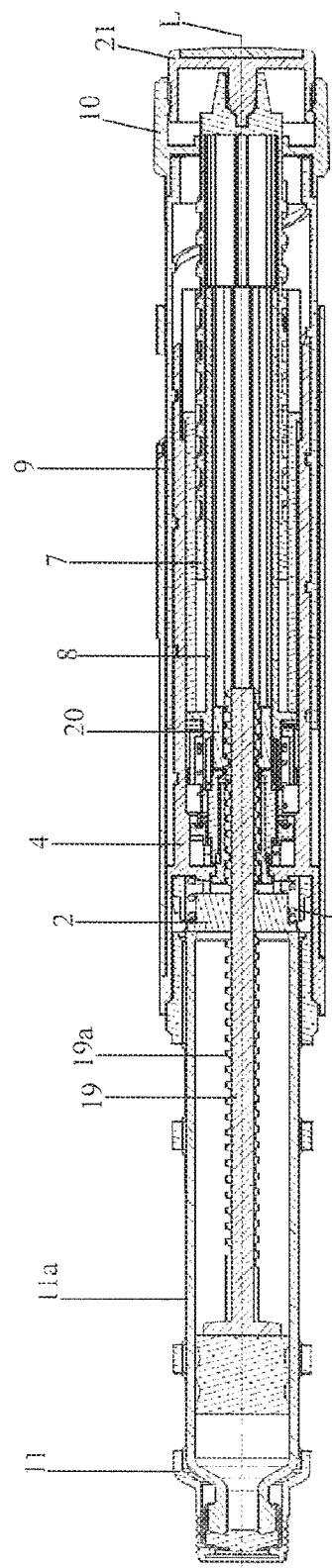
FIG. 6 shows the device according to the first embodiment whereby a dose increase is blocked by the stop element.
Figure 7:
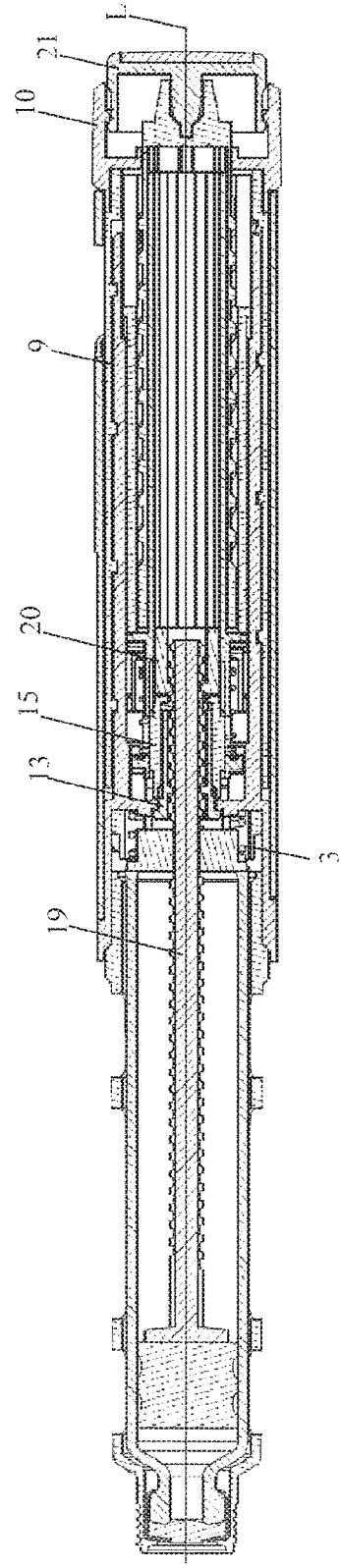
FIG. 7 shows the device according to the first embodiment in a zero dose position after dispensing of the dose set in FIG. 6.
Figure 11:
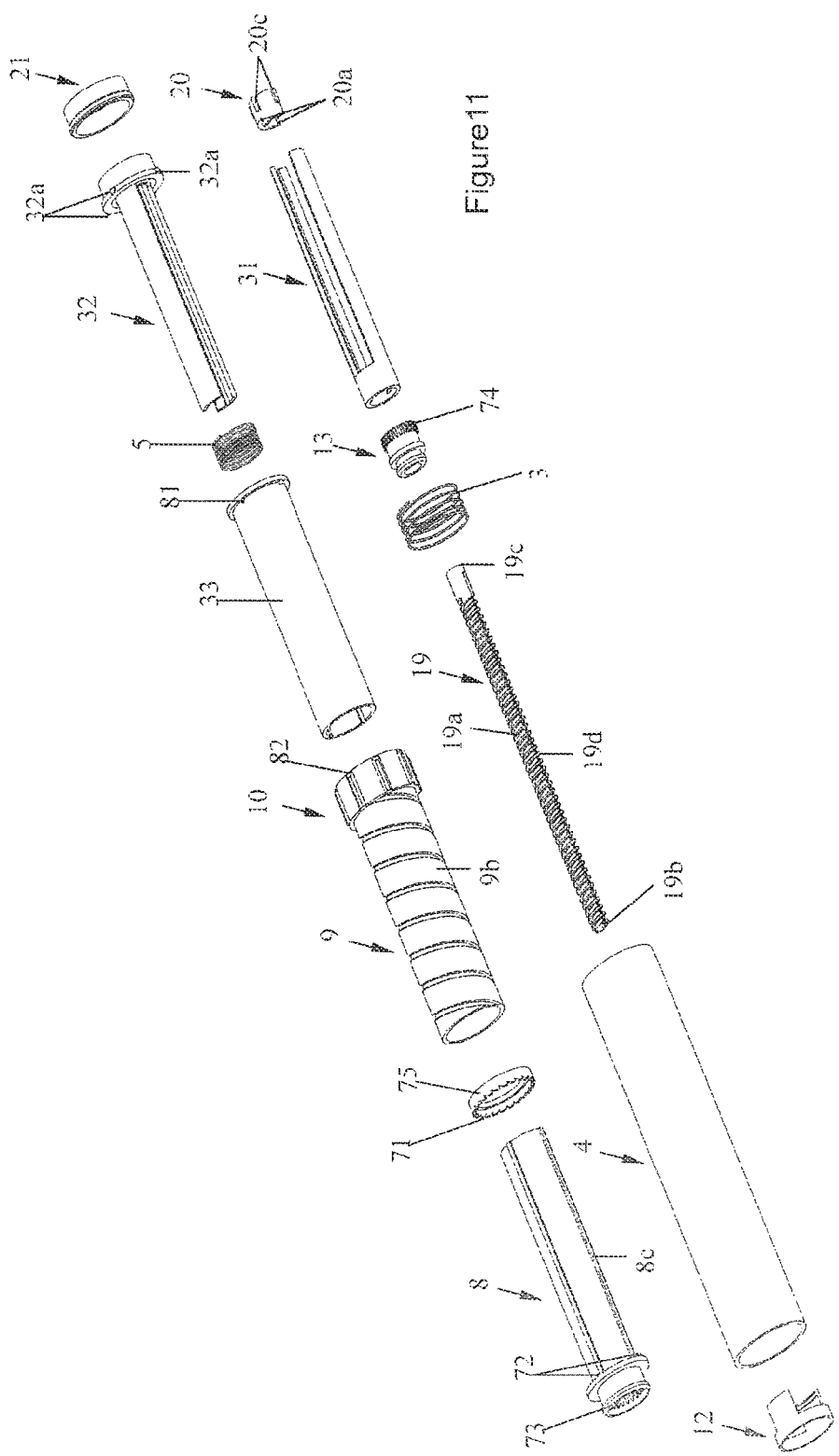
FIG. 11 is an exploded view of the individual parts of a drive and dosing device according to a second embodiment.
Figure 13A:
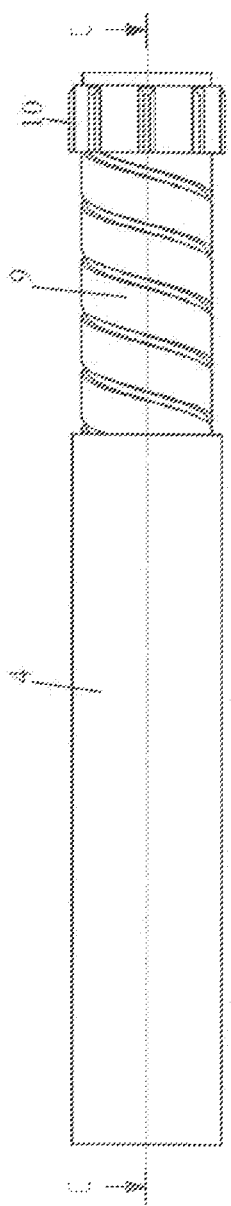
FIG. 13a shows the drive and dosing device of FIG. 12a in a maximum dose position.
Figure 13B:
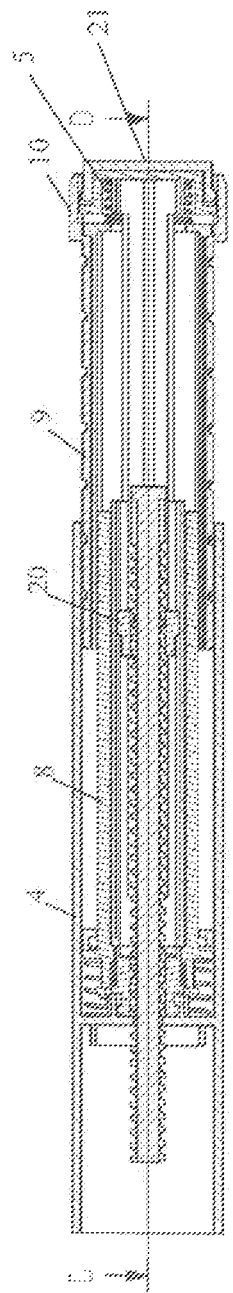
Figure 13C:
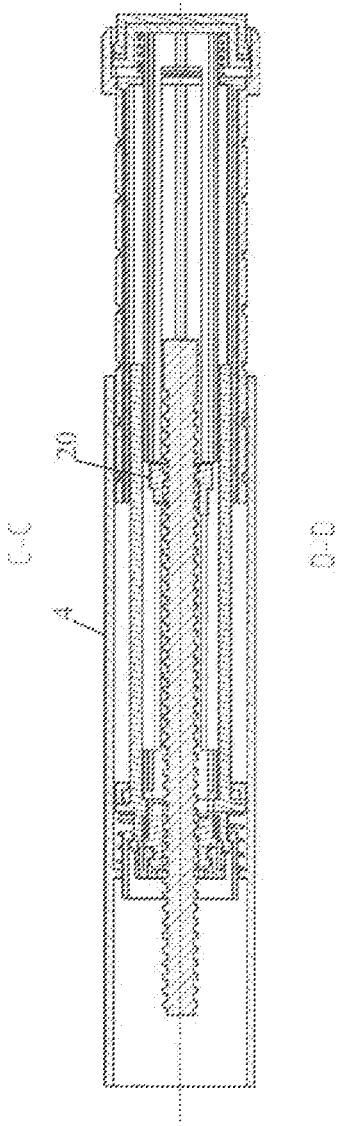
FIG. 13c shows a cross sectional view of the drive and dosing device shown in FIG. 13a taken along the line D-D in FIG. 13b.

In FIGS. 1-10, the first embodiment of a drive and dose setting mechanism is presented with a housing 4, 18 having an external housing 18 and a housing insert or mechanic holder 4 that is concentrically arranged within the external housing. The mechanic holder 4 is rotationally and axially fixed to the external housing 18. The housing 4, 18, more specifically the mechanic holder 4 has a threading 4a engaging with an internal thread of the scale drum 9 such that the scale drum can be screwed along the longitudinal axis L of the housing 4, 18. The scale drum 9 is axially and rotationally fixed to the dose knob 10. In an example, they are snapped together. The user of the drive and dose setting mechanism can hold the dose knob 10 which is rotatable versus the housing 4, 18. The set dose will be increased upon rotation of the dose knob 10 in a first direction whereas the dose will be decreased upon rotation into a second direction which is opposite to the first direction. Rotation of the dose knob 10 in the first direction ensures that the scale drum 9 will be screwed away from the proximal end of the housing 4, 18 and the scale drum 9 will be screwed into the housing 4, 18 upon rotation in the second direction.

The housing 4, 18 (e.g., the external housing 18) has an area for viewing the set dose 18a, such as a viewing window in the external housing 18. The area for viewing the set dose 18a enables the user to read the set dose from the scale drum 9. The scale drum 9 shows on its outer surface a helical shaped scale with a plurality of consecutive numbers. In the shown example the scale runs from 0 to 60 in steps of 2. The numbers represent a dose in International Units (IU). For the setting of a dose of 30 IU, the dose knob 10 is rotated versus the housing 4, 18 until the value of 30 can be read through the viewing window 18a. At the proximal end of the drive and dosing mechanism, there is an actuation element 21 in the form of a dose button and this is the proximal end of the drive and dose setting mechanism. The dose button 21 is arranged in the dose knob 10 such that is can be displaced along an actuation distance relative to the dose knob 10.

The dose button 21 possesses for example a circumferential protrusion 21a on its outer surface that engages with an internal rim 10b of the dose knob 10. In FIGS. 2a, 2b and 3, the dose button 21 is, for example, shown in its non-actuated state. FIGS. 4 and 10a, 10b show the dose button 21 in its actuated state and the dose button is displaced over the actuation distance compared to FIG. 3. The dose button 21 is located at the proximal end of the mechanism and can be easily depressed. For example, the dose button 21 may be actuated by the thumb of a user grabbing the housing 4, 18 with his hand.

For dispensing the set dose, the dose button 21 is depressed further in the distal direction such that the dose knob 10 together with the scale drum 9 can be screwed into the housing 4, 18 (compare FIGS. 4 and 5). The dose button 21 and the dose knob 10 are axially displaced versus the housing 4, 18.

At the distal end of the housing insert 4, respectively the housing 4, 18 is a cartridge holder 11 containing a cartridge or ampoule 11a. The ampoule 11a has at its distal end a septum which can be pierced by a needle. The ampoule also has a plug which can be moved in a dispensing direction (e.g., towards the septum) whereby the liquid product located between the septum and the plug (for example insulin) can be dispensed. The plug is operatively connected to a piston rod 19 having a multiple threading 19a on the outside engaging an internal threading 13a of a rotating member 13, 15. The rotating member 13, 15 includes, in the shown example, of two parts with a threaded nut 13 and a drive nut socket 15 which are axially and rotationally locked to each other. Between the threaded nut 13 and the drive nut socket 15 exists a circumferential notch which is engaged with a part of the housing 4, 18, namely the housing insert 4 such that the rotating member 13, 15 is rotatable versus the housing insert 4 but is not axially displaceable.

A linear slide 2, which is rotationally locked with respect to the housing 4, 18 and which is axially not displaceable or at least limited displaceable (for example in the range of a few millimeters, e.g., less than 5 mm) along the longitudinal axis L, guides the piston rod 19 such that the piston rod cannot rotate versus the housing 4, 18. However, the piston rod 19 is axially displaceable along the longitudinal axis L relative to the linear slide 2. The piston rod 19 has a guiding notch and/or longitudinal notch 19d that is superimposed on the external thread 19a and which is oriented parallel to the longitudinal axis L. The linear slide 2 engages with the guiding notch 19d such that the piston rod 19 is rotationally secured but can be axially displaced along the longitudinal axis L relative to the linear slide 2.

The drive and dosing mechanism has a rotating member 13, 15 which during dose setting (e.g., increasing or decreasing a dose) is rotationally secured with respect to the piston rod 19 and/or the housing 4, 18 and which during dose delivery is rotated relative to the piston rod 19 and/or the housing 4, 18, more particular in the second rotation direction of the dose knob 10. The rotating member 13, 15 follows the rotation of the dose knob 10 during dose delivery. The rotating member 13, 15 engages the external thread 19a of the piston rod by an internal thread 13a of the threaded nut 13. The rotating member is connected to the housing 4, 18, more specifically to the housing insert 4, such that it is axially not displaceable but rotatable versus the housing. The rotating member 13, 15 may have two parts, namely a threaded nut 13 and a drive nut socket 15, which are rotationally and axially locked to each other and behave like a single part. The threaded nut 13 (e.g., drive nut) is made from a polymeric material, for example Teflon, which forms a low friction bearing couple with the piston rod 19. The drive nut socket 15 is made from a polymeric material having strength higher than the strength of the threaded nut 13 (e.g., a fiber reinforced polymer). Between the threaded nut 13 and the drive nut socket 15 exists a circumferential groove that engages a part of the housing 4, 18 or a part that is fixed to the housing, in this example housing insert 4. For instance the threaded nut 13 and the drive nut socket 15 establish the borders of the circumferential groove. This simplifies the mounting of the rotating member 13, 15. Preferentially, the rotation member 13, 15 is axially non-displaceable with respect to the housing 4, 18 during all operation conditions.

A dispense coupling 81, 82 is closed if a user depresses the dose button 21 in the distal direction and is opened upon release of the dose button 21. The dispense coupling 81, 82 couples the rotating member 13, 15 torque-proof with the dose knob 10 when the dispense coupling 81, 82 is closed. The dose knob 10 is rotationally decoupled from the rotation member 13, 15 if the dispense coupling 81, 82 is decoupled (e.g., the dose knob can be rotated versus the rotating member 13, 15).

The dispense coupling 81, 82 may have a first coupling structure 81 (also called a first dispensing coupling structure) and a second coupling structure 82 (also called a second dispensing coupling structure), which are brought into a torque-proof engagement when the coupling 81, 82 is closed. The coupling 81, 82 furthermore comprises a dose spring 5, which spring force tends to disengage the first coupling structure 81 and the second coupling structure 82. The dispense coupling 81, 82 is closed upon actuation of the dose button 21 and the first and second coupling structures are brought into a rotationally secure engagement, thereby compressing the dose spring 5. The dose spring 5 also serves the purpose of resetting the dose button 21 into the non-actuated position.

In the shown example, the first coupling structure 81 is circumferentially arranged internal teeth (e.g., toothing) whereas the second coupling structure 82 is circumferential arranged external teeth, whereby the first and second coupling structures 81, 82 can be brought into engagement by an axial displacement along the longitudinal axis L. In particular, the second coupling structure 82 is rotationally locked with respect to the rotating member 13, 15. Preferably, the second coupling structure 82 is part of the rotating member 13, 15, more preferably part of the drive nut socket 15.

The first coupling structure 81 can be, for example, a drive sleeve 8 which can be geometrically and/or kinematically arranged between the rotating member 13, 15 and the dose button 21. The drive sleeve 8 is displaced relative to the housing 4, 18 and/or piston rod 19 in the distal direction along the longitudinal axis L upon depressing the dose button 21. Upon release of the dose button 21, the drive sleeve will be displaced in the proximal direction due to the energy stored within the dose spring 5.

The drive sleeve 8 is preferably permanently (more preferably during dose setting and dose dispensing) torque-proof engaged with the dose knob 10. Preferably, the first coupling structure 81 is permanent rotationally locked with the dose knob 10.

Located between the drive sleeve 8 and the dose button 21 is a dose sleeve 7, which is rotationally locked and axially displaceable with respect to the drive sleeve 8. The dose sleeve 7 possesses on its inner surface one or more guiding keys 7c which are arranged along the longitudinal axis L and which engage one or more guiding grooves, which are arranged on the outside surface of the drive sleeve 8 such that an axially displaceable but rotationally locked connection exists between the dose sleeve 7 and the drive sleeve 8.

The dose sleeve 7 has a thread 7b on the outside surface, which is limited on its distal end by a stop maximum dose 7e, and by a stop zero dose 7d on its proximal end. A coupling sleeve 6 has an internal thread 6b engaging with the thread 7b. In FIG. 1, the internal thread segment 6b is visible on the outside as a depression although it is an internal thread segment. This is done for manufacturing purposes, the depressions on the outside prevent material accumulation during the injection molding process. The at least one internal thread segment 6b has an end along the circumferential direction that forms a maximum dose limiter, and it touches the stop maximum dose 7e when the dose knob 10 is in the maximum dose position and is rotated in the first direction. The at least one internal thread segment 6b has an end along the opposite circumferential direction which forms a zero dose limiter, and it touches the stop zero dose 7d when the dose knob is in the zero dose position and is rotated in the second direction. The thread 7b is a multiple thread, in the shown example a quadruple thread. In particular, the thread 7b can have the same pitch as the thread 4a.

As an alternative, the housing insert 4, respectively the housing 4, 18 can have the stop zero dose 4c, for example at the distal end of thread 4a. The counter member for the stop zero dose can be formed, for example at the inner surface of the scale drum 9. For example, the counter member for the stop zero dose can be an end of the internal thread or internal thread segment of the scale drum 9 that engages the thread 4a.

The dose sleeve 7 is preferably permanently rotationally fixed but axially slidably connected to the dose knob 10. Therefore, the dose sleeve 7 has keys 7a, which extend along the longitudinal axis L and engage with one or more recesses 10a of the dose knob 10.

Positioned between the housing insert 4 and the dose sleeve 7 is the clutch 6, which is shaped as a coupling sleeve and also called coupling sleeve 6. The coupling sleeve 6 is engaged with the internal housing 4 such that it is rotationally secured but axially slidable. The coupling sleeve 6 has on its outer surface one or more splines 6a which engage with a notch of the housing insert 4 that is arranged parallel to the longitudinal axis L. The coupling sleeve 6 has an internal thread which engages the thread 7b of the dose sleeve 7.

The dose button 21 is connected to the proximal end of the dose sleeve 7 such that it can rotate freely.

A unidirectional coupling 71, 72, 73, 74 (which is generally referenced below as 70) is located in the housing 4, 18. During the dose setting and/or delivery the unidirectional coupling 70 does not permit a rotation in the first direction of the rotation member 13, 15 relative to the housing 13, 15 and/or piston rod 19 whereas it permits a rotation in the second direction. The unidirectional coupling 70 can be shaped as a ratchet. The unidirectional coupling 70 prevents rotation of the rotation member 13, 15 in the first direction during increasing a dose setting due to frictional forces potentially occurring between the dose knob 10 and the rotation member 13, 15 or due to elastic forces originating from the plug in cartridge 11a which tend to push the piston rod 19 into the proximal direction.

The unidirectional coupling 70 can act as a permanent, non-releasable coupling as far as the drive and dose setting mechanism is used as a disposable component (e.g., a component which will be disposed after completely emptying the cartridge 11a). If the drive and dose setting mechanism is intended for repeated use (e.g., the cartridge 11a can be replaced by another cartridge 11a) it is preferred that the unidirectional coupling 70 can be released during exchange of a cartridge whereby the rotation member 13, 15 can be rotated in the first direction relative to the housing 4, 18 such that the piston rod 19 can be reset in its original position.

The unidirectional coupling 70 has a first coupling structure 71 and a second coupling structure 72, whereby the first and second coupling structures 71, 72 engage such that they are only rotatable in one direction versus each other. The first coupling structure 71 can be, for example, locked to the housing 4, 18 or at least rotationally locked to the housing 4, 18, for example to a switching element 12. The second coupling structure 72 can, for example, be formed by the rotation member 13, 15, more preferably the drive nut socket 15 or at least from a part that is at least temporarily rotationally connected to the rotation member 13, 15, such as coupling ring 14 or shaped onto coupling ring 14. The coupling ring 14 is preferably rotationally locked and axially moveable with respect to the rotation member, at least during dose setting and dose dispensing. Particularly, the first and second coupling structures 71, 72 are engaged by a spring, preferably dose spring 5. Preferably, the first coupling structure 71 and the second coupling structure 72 encompass circumferentially arranged saw tooth structures. The first coupling structure 71 preferably points into the proximal direction and the second coupling structure 72 points in the distal direction. The teeth of the first coupling structure 71 and the second coupling structure 72 preferably point to each other. The saw teeth of the coupling structures 71, 72 have a steep and a flat face, whereby the flat face of one coupling structure can slip over the flat face of the other coupling structure, whereby the second coupling structure 72 can rotate relative to the first coupling structure 71 in the second direction. The steep faces of the coupling structures 71, 72 are pressed together at the attempt of rotating the second coupling structure 72 in the first direction relative to the first coupling structure 71, thereby preventing rotation of the second coupling structure in the first direction.

For setting a dose, the dose knob 10 is rotated in the first direction relative to the housing 4, 18 and the dose knob 10 is rotated out of the proximal end of the housing 4, 18 together with the scale drum 9 (see, e.g., FIG. 3). The set dose can be read from the dose scale 9b in the viewing window 18a. The dispense coupling 81, 82 is decoupled during the dose setting. In FIG. 3, the device is presented after a dose has been set and that can be dispensed.

For dispensing a set dose as shown in FIG. 3, the dose button 21 is pressed in the distal direction versus the dose knob 10 along an actuation distance (compare FIGS. 3 and 4) whereby the dose sleeve 7 is also displaced versus the housing 4, 18 along the actuation distance of the dose button 21. The coupling sleeve 6 is displaced in the distal direction over the actuation distance of the dose button 21 due to the thread engagement that exists between the dose sleeve 7 and the coupling sleeve 6. The coupling sleeve 6 pushes the drive sleeve 8 also in the distal direction, particularly over the actuation distance of the dose button 21. As a result, the first coupling structure 81 present at the drive sleeve 8 is brought into a rotationally stable engagement with the second coupling structure 82 present at the rotation member 13, 15 thereby closing the coupling structure 81, 82. The device is shown in FIG. 4 with an actuated dose button 21.

Upon pressing the dose button 21 in the distal direction, the dose knob 10 is screwed back into the housing 4, 8 along a distance corresponding to the set dose (compare FIGS. 4 and 5). Hereby the dose knob rotates and the set dose value counts back as can be seen through the viewing window 18a. The rotational movement of the dose knob 10 is transferred to the dose sleeve 7 and the drive sleeve 8 and from the drive sleeve 8 to the rotation element 13, 15 via the coupled dispense coupling 81, 82. As a result, the rotation element 13, 15 rotates relative to the housing 4, 18 and/or piston rod 19 in the second direction, identical to the rotation direction of the dose knob 10. Due to this rotational movement, the piston rod moves in the distal direction, whereby the piston rod 19 is rotationally locked with respect to the housing 4, 18 by the linear slide 2. The flange at the distal end of the piston rod 19 pushes against the plug of the cartridge 11a and moves the plug in the dispensing direction for dispensing the set dose. The piston rod 19 moves along a dispensing distance whereas the dose knob moves along a dose setting distance whereby the dose setting distance is proportional to and above the dispensing distance resulting in a gearing from the force applied to the dose button 21 to the plug of the cartridge.

This procedure can be repeated several times whereby each time an individual dose can be set.

The device is shown in FIG. 6 with a volume present in the cartridge 11a which is below the maximum dose that can be set on the device. The device has a stop element 20 in order to prevent setting a dose exceeding the dispensable volume present in the cartridge 11a. The stop element 20 is a sleeve shaped nut having an internal thread 20b engaging with the thread 19a of the piston rod 19. Furthermore, the stop element 20 is rotationally secured and axially slidably engaged with the drive sleeve 8. The drive sleeve 8 has, for example, at least one circumferentially arranged longitudinal notch engaging at least one rim 20c arranged on the outer surface of the stop element 20.

Additionally, the stop element 20 has, particularly at its distal end, a catch 20a shaped as a surface with a normal oriented towards the circumferential direction. The rotation member 13, 15, particularly the drive nut socket 15 has a stop limiter 15a shaped as a surface with a normal pointing in the circumferential direction. The distance along the helical shaped curve, notably along the thread 19a between the stop limiter 15a and the catch 20a, corresponds to the dose which can be set and/or the dose or volume which still can be dispensed from the cartridge.

The stop element 20 is preferably permanently torque-proof connected to the dose knob 10 so that rotations of the dose knob 10 during the dose setting and dispensing are transferred to the stop element. The stop element 20 and the piston rod 19 are shown in FIGS. 2a and 2b in an initial position or zero dose position when a dose of zero has been set. If the dose knob 10 is rotated in a first direction with respect to the piston rod 19 for increasing a dose, then the stop element 20, which is rotationally secured with the dose knob 10, also rotates with respect to the piston rod 19 whereby the stop element 20 is screwed in the distal direction with respect to the piston rod 19 and the housing 4, 18 (see, e.g., FIG. 3). If the dose knob 10 is rotated in the second direction with respect to the housing 4, 18 for correcting a dose, then the stop element 20 is screwed relative to the piston rod 19 and the housing 4, 18 in a proximal direction.

If the dose knob 10 is rotated in the second direction for delivering a dose (e.g., when the dose button pressed) then the stop element 20 is screwed relative to the piston rod to its proximal end whereby the stop element maintains its position with respect to the housing 4, 18 and/or rotation member 13, 15 along the longitudinal axis L. During dose delivery, the stop element is only subjected to a rotational movement without an axial movement relative to the housing 4, 18. Preferably, the stop element is rotationally locked with respect to the rotation member 13, 15. This implies that the distance between the stop limiter 15a and the catch 20a does not change during dose delivery. At the end of the dose delivery (e.g., when the zero value can be read from the viewing window) the stop element will be at substantially the same location as before the setting of the dose which was delivered (compare FIGS. 2a, 2b with FIG. 5).

If the volume present in the cartridge 11a is below the maximum dose which can be set, then the catch 20a of the stop element 20 abuts the stop limiter 15a when the dose knob 10 is rotated in a first direction for increasing a dose. At the attempt of rotating the dose knob 10 in the first direction, the dose knob 10 will be blocked from further rotating due to abutting of the stop element 20 with the rotation member 13, 15. Setting a dose which exceeds the dispensable amount of product present in the cartridge 11a will be prevented.

In an alternative which is not shown here, the distance between the catch 20a and the stop limiter 15a is less compared to the shown embodiment (e.g., the stop element is more to the left in the drawings), which results in an earlier blocking of the rotation of the dose knob 10 in the first direction. A residual volume will remain in the cartridge 11a which is the difference between the nominal volume in the cartridge 11a and the dispensable volume. In the alternative, setting a dose is prevented that would result in that in the cartridge 11a less than the residual volume of the nominal volume would remain.

The dose button 21 is actuated for dispensing the dose as set in FIG. 6 and the dose knob 10 is rotated back into the housing over the dispensing distance. After dispensing (see, e.g., FIG. 7), the stop element 20 is located at the same location with respect to the piston rod 19 as the zero dose position of the previous dispensings (see, e.g., FIGS. 2a, 2b, 5).

The cartridge holder 11, which can hold the cartridge 11a, can be released and removed from the drive and dosing device for embodiments where an empty cartridge holder 11a (see, e.g., FIG. 8) can be replaced by a new cartridge holder 11a (see, e.g., FIG. 9). The empty cartridge 11a is removed from the cartridge holder 11 and a new cartridge 11a is inserted in the proximal end of the cartridge holder 11. The cartridge holder 11 is connected to the drive and dosing device using a bayonet connector or a plug-and-rotate connector.

The cartridge holder 11 has at its outer surface a protrusion 11b and a circumferential collar 11d extending along the outer surface. The housing 4, 18, particularly the housing insert 4 has a bayonet slot 4b with an axial section parallel to the longitudinal axis L and a circumferential section which is connected to the axial section. When the cartridge holder 11 is connected, the protrusion is located in the circumferential section of the bayonet slot 4b (see, e.g., FIG. 7). The collar 11d abuts the distal end of the housing 4, 18, more particularly the housing insert 4. For removing the cartridge holder 11, the cartridge holder 11 is rotated with respect to the housing 4, 18 such that the protrusion 11b moves into the direction of the axial section of the bayonet slot 4b. Once arrived, the cartridge holder 11 can be pulled along the longitudinal axis L and can be removed from the drive and dosing device. This procedure is reversed for attaching the cartridge holder 11 to the drive and dosing device. The cartridge holder 11 is moved towards the distal end of the drive and dosing device, whereby the protrusion 11b is pushed in the axial section of the bayonet slot 4b. Rotation of the cartridge holder 11 relative to the housing 4, 18 moves the protrusion 11b in the circumferential section of the bayonet slot 4b, fixating the cartridge holder 11 to the housing. In particular, the collar lid is pushed against the distal end of the housing insert 4.

The cartridge 11a, which can be held by the cartridge holder 11, is generally made from plastic or glass. The length of the cartridge 11 is subjected to relatively high dimensional tolerances, for example in the range of a couple of tenths of millimeters. The device shown in FIGS. 1-10b has a mechanism that ensures that the cartridge 11a, despite the high manufacturing tolerances, is tightly locked by the cartridge holder 11. Part of this mechanism is the linear slide 2 which, via the proximal end of the cartridge 11a, can be moved along the longitudinal axis L relative to the housing. A cartridge spring 3, which can also be called a tolerance compensation spring, acts upon the linear slide 2. The cartridge spring is retained at its distal end by the linear slide 2 and at its proximal end by the housing 4, 18, more particularly the housing insert 4. The proximal end of the cartridge 11a touches the linear slide 2 upon attaching the cartridge holder 11 to the drive and dosing device whereby the linear slide 2 is moved into the proximal direction thereby tensioning the cartridge spring 3. The cartridge spring 3 ensures that the cartridge is axially secured in the cartridge holder 11. Dimensional tolerances for the length of the cartridge 11a can be compensated for by the resilient nature of the linear slide 2. The linear slide 2 is located between the proximal end of the cartridge 11a and the cartridge spring 3.

Upon releasing the cartridge holder 11 from the drive and dosing device, the linear slide 2 is moved in the distal direction along the longitudinal axis L and relative to the housing 4, 18 due to the preloaded cartridge spring 3.

As can be observed in FIGS. 8 and 9, the piston rod 19 may be reset to its original position for insertion of a new cartridge 11a.

The unidirectional coupling 70 can be switched from its active state, blocking the rotation in the first direction of the rotation member 13, 15, into an inactive state thereby allowing rotation of the rotation member 13, 15 in the first direction.

The coupling 70 has a third coupling structure 73 at the coupling ring 14 and a fourth coupling structure 74 present at the rotation member 13, 15, preferably at drive nut socket 15. If the cartridge holder 11 is attached to the drive and dosing device, then the third coupling structure 73 and the fourth coupling structure 74 are in a rotationally secured engagement such that the rotation member 13, 15 is rotationally locked with the coupling ring 14 (e.g., in both rotation directions torque-proof engaged). The cartridge holder 11 is coupled to the third coupling structure 73 such that the third coupling structure 73 disengages from the fourth coupling structure 74 when the cartridge holder 11 is released from the drive and dosing device, particularly when the cartridge holder 11 is moved in the distal direction relative to the housing 4, 18. The coupling 70 is then in its inactive state. The cartridge holder 11 is coupled with the third coupling structure 73 such that upon attachment of the cartridge holder 11 to the drive and dosing device the third coupling structure 73 is moved into the coupled state with the fourth coupling structure 74. The third coupling structure 73 is thereby moved in the proximal direction along the longitudinal axis L with respect to the housing 4, 18. Notably, the third coupling structure 73, more specifically the coupling ring 14 having the third coupling structure, can be moved against the force of dose spring 5 in the proximal direction, thereby straining the dose spring 5. Particularly, the dose spring 5 can move the third coupling structure 73, more particularly the coupling ring 14, in the distal direction when the cartridge holder 11 is released from the housing 4, 18. Hereto, the dose spring 5 supports the coupling ring 14, more particularly with its distal end.

The third coupling structure 73 preferably has internal teeth, whereby the fourth coupling structure 74 has external teeth.

The third coupling structure 73, particularly the coupling ring 14 is coupled with the cartridge holder 11 via the switching element 12 which itself is rotationally secured and axially slidable along the longitudinal axis L with respect to the housing 4, 18. In the example shown, the switching element 12 is coupled to the cartridge holder 11 such that a rotation of the cartridge holder 11 relative to the housing 4, 18 results in an axial movement of the switching element 12 along the longitudinal axis L. The switching element 12 is moved in the distal direction when the cartridge holder 11 is rotated in a direction for releasing the cartridge holder from the housing 4, 18. The switching element 12 is moved in the proximal direction when the cartridge holder 11 is rotated in a direction for attaching the cartridge holder 11 to the housing 4, 18. Particularly, the cartridge holder 11 can slip on the switching element 12 if the cartridge holder 11 is rotated relative to the housing 4, 18 and the switching element 12. The cartridge holder 11 has on its proximal end, for example, an activation element 11c having a sloped surface that can slip on the switching element 12 when the cartridge holder 11 is rotated relative to the switching element 12 thereby initiating the axial movement of the switching element 12. Preferably the switching element 12 has a recess 12c, which is adapted to the shape of the activation element 11c, whereby the activation element slips into recess 12c upon insertion of the protrusion 11b into the axial section of the bayonet slot 4b. A subsequent rotation of the cartridge holder 11 relative to the switching element 12 releases the activation element from the recess 12c whereby the switching element 12 moves along the longitudinal axis L. Rotation of the cartridge holder 11 in the opposite direction for removing the cartridge holder 11 from the drive and dosing device establishes a form fit between the activation element 11c and the recess 12c whereby the switching element is moved in the distal direction due to the resilient forces acting from the dose spring 5.

As mentioned previously, the coupling 70 is in its inactive state when the cartridge holder 11 is released from the drive and dosing device (see, e.g., FIG. 8). The piston rod 19 can be reset or pushed back into the drive and dosing device, particularly through the muscle power of the user of the device. Hereby the piston rod 19 is rotationally secured with respect to the housing 4, 18 and the piston rod 19 is moved axially along the longitudinal axis L into the housing 4, 18. As a result, the stop element 20 is moved accordingly whereby the stop element 20 is rationally and axially secured with respect to the piston rod 19. Furthermore, the rotation member 13, 15 is rotated during reset in the first rotation direction because, as mentioned before, the coupling 70 is in its inactive status.

The cartridge holder 11 can be attached to the drive and dosing device after resetting the piston rod 19, as described above (see, e.g., FIG. 9).

The drive and dosing device of FIGS. 1-10b has a mechanism which, during dose dialing, particularly during dial up or dial down, produces an acoustic and/or tactile signal which also can be designated as a "click" and which dictates discrete angular steps for the dose knob 10 when rotated with respect to the housing 4, 18. The mechanism encompasses particularly a dose adjustment ratchet 16, a ratchet ring 17 and the drive sleeve 8. A first clicker surface 91 is located on an outwardly projected ring-shaped collar of the drive sleeve 8 and this surface, in this example a saw tooth structure, points in the distal direction. The ratchet ring 17 has a second clicker surface 92 that is engaged with the first clicker surface 91 and which points in the proximal direction. Furthermore, the ratchet ring 17 has a third clicker surface 93 oriented towards the distal direction and which is engaged with a fourth clicker surface 94 oriented towards the proximal direction and which is located at the dose adjustment ratchet 16. The clicker surfaces 91, 92, 93, 94 are saw tooth structures arranged on an outer surface of each component part. The individual saw tooth of the clicker surfaces are distanced over an angle corresponding to the discrete steps dictated to the dose knob 10. For example, if for the drive and dosing device the dose shall be set in steps of 1 IU then the angular distance for the saw tooth is adjusted such that rotation of the dose knob 10 along one discrete step corresponds to 1 IU Accordingly, an acoustic respectively tactile signal is produced during each discrete step of the rotation of the dose knob. For the sake of completeness, the angular distance of the saw tooth can be such that it corresponds to angular steps of the dose knob above or below 1 IU for example 0.5 IU or 2 IU or 5 IU The dose adjustment ratchet 16 is rotationally secured and axially moveable along the longitudinal axis L in the housing 4, 18, particularly in the housing insert 4 if the dose button 21 is not actuated. When the dose button 21 is actuated, the dose adjustment ratchet 16 is moved along the longitudinal axis L out of this engagement so that the dose adjustment ratchet 16 is rotatable with respect to the housing 4, 18. The dose adjustment ratchet 16 has external teeth 16a that engage with internal teeth 4d present at the inner surface of the housing insert 4 that form a rotationally secure engagement. When the dose button 21 is pressed, the external teeth 16a along the longitudinal axis L are moved out of engagement from the internal teeth 4d, and the dose adjustment ratchet 16 is rotatable with respect to the housing 4, 18. In other words the dose adjustment ratchet 16 is rotationally secured versus the housing 4, 18 during dose setting and is rotatable versus the housing 4, 18 during dose delivery.

The aforementioned mechanism in the shown embodiments also serves the purpose of providing for the drive sleeve 8 a certain resistance against rotation in the second direction during actuation of the dose button 21 (e.g., when the dose button 21 is not in the actuated position yet) and thus preventing a premature rotation of the drive sleeve 8. This resistance against rotation is preferably (minimally) above the torque generated by the axial displacement of the actuation element 21, more specifically the torque due to the threaded engagement between the dose sleeve 7 and the coupling sleeve 6 acting on the drive sleeve 8. This resistance against rotation disappears when the dose button 21 is beyond the intermediate actuation position (described in more detail below).

Optionally, the unidirectional coupling 70 can provide a certain resistance against rotation in the second direction during actuation of the dose button 21 (e.g., the dose button 21 is not yet in the actuated position) thus preventing a premature rotation of the drive sleeve 8 in the second direction, since the dispense coupling 81, 82 is already closed. If the dose button 21 is in its actuated position and pushed by the user further in the distal direction, then the resistance provided by the unidirectional coupling is resolved, whereby the drive sleeve 8 and the rotation member 13, 15 are rotated in the second direction.

The drive sleeve 8 is rotated relative to the dose adjustment ratchet 16 upon dialing up a dose (e.g., rotation of the dose knob 10 is the first direction) and upon dialing down a dose (e.g., rotation of the dose knob 10 in the second direction). The ratchet ring 17 is located between the first clicker surface 91 and the fourth clicker surface 94. Upon dialing up a dose, the ratchet ring 17 co-rotates relative to either the dose adjustment ratchet 16 or the drive sleeve 8, and does not co-rotate relative to the other. During dialing down a dose, the ratchet ring 17 does not co-rotate relative to either the dose adjustment ratchet 16 or the drive sleeve 8 and co-rotates relative to the other. In the shown example, the ratchet ring 17 follows the rotation of the drive sleeve 8 during dial up and rotates relative to the dose adjustment ratchet 16. During down dialing of a dose, the dose sleeve 8 rotates relative to the ratchet ring 17, whereby the ratchet ring 17 does not rotate relative to the dose adjustment ratchet 16. During dialing up and dialing down the clicker surfaces 91 to 94 slide along each other and thus produce the so-called "clicks". The dose spring 5 abuts with its proximal end the dose adjustment ratchet 16 and keeps the dose adjustment ratchet 16, ratchet ring 17 and the drive sleeve 8 in a ratchet engagement. Moreover, the dose spring 5 returns, as described, the dose button 21 to its original position. Upon actuation of the dose button 21, the dose adjustment ratchet 16, respectively the external teeth 16a are moved out of the torque-proof engagement with the housing 4, 18, respectively the internal teeth 4d, due to the distal movement of the drive sleeve 8 and the ratchet ring 17, thus deactivating the clicker mechanism during dose dispensing. It is preferred that the dispense coupling 81, 82 and the coupling 16a, 4d are coupled during the movement of the dose button 21 (e.g., when the dose button is between the actuated and the non-actuated position, such as in an intermediate position). This ensures that—during the actuation of the dose button 21—the coupling 16a, 4d is not decoupled until the dispense coupling 81, 82 is already coupled. Thus it is ensured that no accidental shift of the set dose can occur during the actuation of the dose button.

A second embodiment is shown in FIGS. 11-18 for a drive and dosing device with a sleeve shaped housing 4 which also acts as the mechanic holder. The housing 4 has a distal end to which a cartridge holder with a cartridge can be attached (not shown), and a proximal end having a rotatable dose knob 10. The housing 4 has an internal thread which engages an external thread of the scale drum 9, and the scale drum 9 is rotationally and axially stably connected to the dose knob 10. Although not shown, the housing 4 has a region for viewing the dose scale, and the scale drum 9 has a dose scale, such as one described in the first embodiment. For setting a dose, the dose knob 10 is rotated in a first direction relative to the housing 4 out of the proximal end of the housing 4. For correction of a dose and for dispensing a dose, the dose knob 10 is rotated in a second direction relative to the housing 4 into the proximal end of the housing 4.

The drive and dosing device has a piston rod 19 with an external threading 19a and at least a guide arranged parallel to the longitudinal axis. The guide may be a guiding notch. A part of the housing or a part rotationally locked to the housing engages with the guiding notch. The piston rod 19 may be rotationally fixed relative to the housing 4 and moveable along the longitudinal axis L of the piston rod 19, which is identical to the longitudinal axis L of the drive and dosing device. An internal thread of the nut 13 engages with the external thread of 19a of the piston rod 19 whereby the nut 13 is axially locked but rotatable connected to the housing 4. The piston rod 19 has a distal end 19b and a proximal end 19c.

The rotation member 13 is rotationally-fixed connected to a drive sleeve 8 via a reset coupling 73, 74, when the cartridge holder is connected to the drive and dosing device. The reset coupling 73, 74 has a coupling structure 74 shaped as teeth present at the external surface of the rotating member 13. The drive sleeve 8 has the coupling structure 73 which is shaped as teeth present at its internal surface. The rotating member 13 and the drive sleeve 8 are torque-proof connected if the coupling structure 73 is coupled with the coupling structure 74. The drive sleeve 8 is rotationally locked and axially slidably connected to the coupling sleeve 33 which surrounds the drive sleeve 8, for example through protrusions present at the outer surface of the drive sleeve 8 engaging with notches present at the inner surface of the coupling sleeve 33. The coupling sleeve 33 has, at its proximal end, an outwardly protruding collar having a first coupling structure 81, in the example shown as a plurality of teeth pointing into the distal direction. The first coupling structure 81 is part of the dispense coupling 81, 82 having also the second coupling structure 82 which is part of the dose knob 10 and/or the scale drum 9. The second coupling structure 82 has a plurality of teeth arranged on a circumferential surface. At the proximal end of the drive and dosing device is an actuation element 21 shaped as a dose button that can be pressed in the distal direction relative to the dose knob 10 to move along an actuation distance into an actuated position. A dose spring 5 is arranged between the coupling sleeve 33 and the dose button 21 which upon release of the dose button 21 returns the dose button into the non-actuated position and which is stressed upon actuation of the dose button 21.

The drive sleeve 8 and the coupling sleeve 33 are rotationally locked with respect to the housing 4 during dose setting (e.g., dial up or dial down of a dose). If the dose knob 10, as shown in FIGS. 12a-c, is rotated in a first direction for increasing a dose, then it is rotated out of the proximal end of the housing 4 whereby the coupling structure 82 of the dispense coupling 81, 82 slides along the coupling structure 81 and whereby the coupling structure 81 and the coupling sleeve 33 oscillate along the longitudinal axis L. The spring force of dose spring 5 is selected such that it slightly presses the coupling structure 81 into engagement with the second coupling structure 82 so that a rotation of the dose knob 10 presses the teeth of coupling structure 81 out of engagement with the second coupling structure 82 without the coupling sleeve 33 following the rotation of the dose knob 10.

If the desired dose has been set (see, e.g., FIGS. 13a-13c) then the dose button 21 is pressed (see, e.g., FIGS. 14a-14c) and the coupling structures 81, 82 are held in a rotationally-secure engagement through the actuation of the dose button 21 whereby the coupling sleeve 33 follows the rotational movement of the dose knob 10 when the dose knob 10 is rotated back into the housing (compare, e.g., FIGS. 13a-13c and FIGS. 14a-14c). Generally speaking, the dose knob 10 is rotationally coupled with nut 13 when the dose button 21 is actuated. This coupling may be achieved through dispense coupling 81, 82, the rotationally-secured connection between the coupling sleeve 33 and the drive sleeve 8, and (at least temporarily, particularly when the cartridge holder has been attached to the device) the rotationally-secured connection between the drive sleeve 8 and the nut 13.

The piston rod 19 is displaced along a dispensing distance and is moved in the distal direction due to the rotation of the nut 13 in the second direction relative to the piston rod 19. The drive and dosing device of the second embodiment also has a mechanism to prevent setting a dose which is above the amount present in the cartridge. This mechanism comprises a stop element 20 which surrounds the piston rod 19 in a ring shaped manner and which has an internal thread engaging with an external thread of the piston rod 19. Particularly, the stop element 20 is permanently rotationally-secured connected with the dose knob 10, preferably through coupling 31, 32. The coupling 31, 32 comprises a first coupler sleeve 31 and a second coupler sleeve 32. The first coupling sleeve 31 and the second coupling sleeve 32 are interlocked such that they are rotationally secured and axially slidable with respect to each other. The second coupling sleeve 32 follows the screw movements of the dose knob 10 during dose setting and dose delivery. The stop element 20 engages the first and/or second coupling sleeve 31, 32 in a rotationally secure and axially slidable connection. The first coupling sleeve 31 and/or the second coupling sleeve 32 can have a guiding notch that engages a protrusion shaped at the outer surface of the stop element 20. The second coupling sleeve 32 is, with respect to the dose knob 10, rotationally secured but axially moveable along the actuation distance of the dose button 21. For this, the second coupling sleeve 32 has at least one protrusion 32a which engages a guide oriented parallel to the longitudinal axis L of the device. The dose spring 5 abuts the second coupler sleeve 32. Particularly, a flange attached to the second coupling sleeve 32 is pressed against the coupling sleeve 33, more preferably against its proximal end when the dose button 21 is activated whereby the coupling structures 81, 82 are in a rotational locked engagement.

The dose button 21 is preferably freely rotatable with respect to the dose knob 10 and/or second coupling sleeve 32. For this, the dose button 21 can have a contact surface with a diameter as low as possible and which is disposed in the central area and which contacts a surface at the proximal end of the coupler sleeve 32. This results in a reduction of the friction when there is a rotation between the coupling sleeve 32 and the dose button 21.

If the dose knob 10 is rotated in the first rotation direction for increasing a dose, then the stop element 20 is also rotated in the first direction relative to the piston rod 19, whereby the stop element 20 is screwed along the piston rod 19 and relative to the housing 4 in the distal direction towards the distal end 19b. If the dose knob 10 is rotated in the second direction for reducing a dose, then the stop element 20 is also rotated in the second direction relative to the piston rod 19 whereby the stop element 20 is screwed along the piston rod 19 and relative to the housing 4 in the proximal direction towards the proximal end 19c.

If the dose button 21 is actuated for dispensing a dose, and the dose knob 10 is pushed back (and thereby screwed back) into the housing 4, then the stop element 20 will be screwed along the piston rod 19 towards the proximal end of the piston rod 19 whereby it, with respect to the housing 4, rotates but remains axially at the same location. The reason for this is that the piston rod 19 moves into the dispensing direction.

At the end of the dose dispensing (see, e.g., FIGS. 14a-14c), the stop element 20 is located at the same position with respect to the piston rod 19 as for the zero dose position before setting and dispensing a dose. The kinematics of the stop element 20 may be the same as the first embodiment.

Comparable to the first embodiment, the stop element 20 has at least one catch 20a, which is interacts with a stop limiter 15a that is shaped on the nut 13.

In FIGS. 15a-15c, the situation is presented where the stop element 20 prevents the setting of a dose that is above the amount present in the cartridge. The distance between the catch 20a and the stop limiter 15a is reduced when rotating the dose knob in the first rotation direction. The distance is proportional to the amount of product present in the cartridge. If the stop element 20 abuts the nut 13, then the rotation of the stop element 20 in the first rotation direction is prevented or blocked.

Also this embodiment can—comparable to the first embodiment—be modified such that the setting of a dose is prevented which would result in a remaining volume in the cartridge less than the residual volume of the nominal volume by reducing the distance between the stop limiter 15a and the catch 20a, for example during device assembly.

Figure 16A:
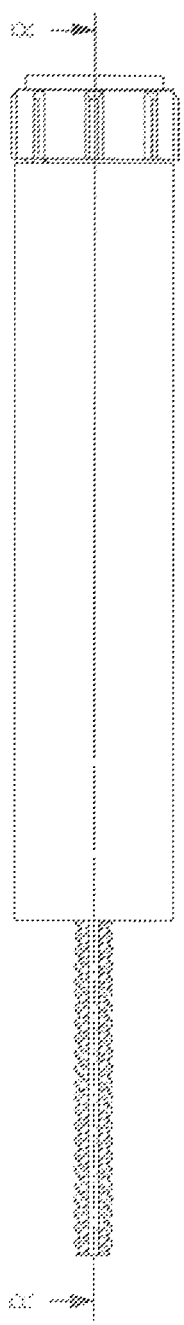
FIG. 16a shows the drive and dosing device of FIG. 15a after the dose set in FIGS. 15a-15c has been dispensed.
Figure 16B:
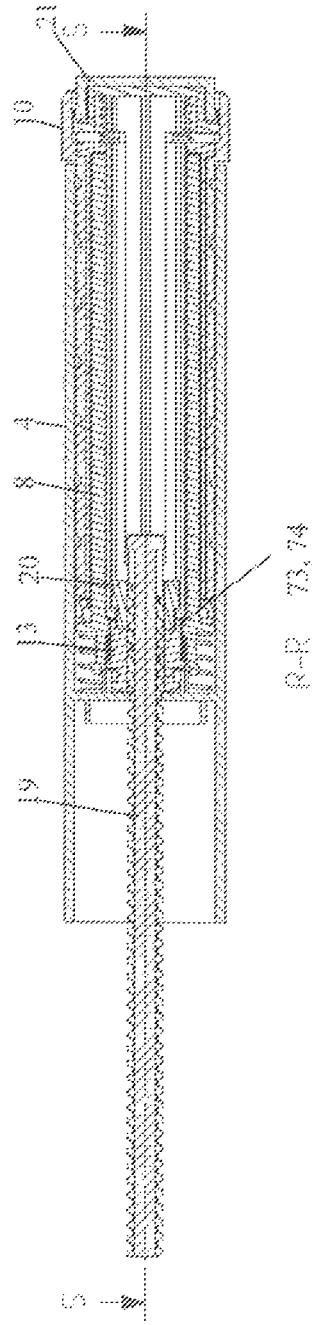
Figure 16C:
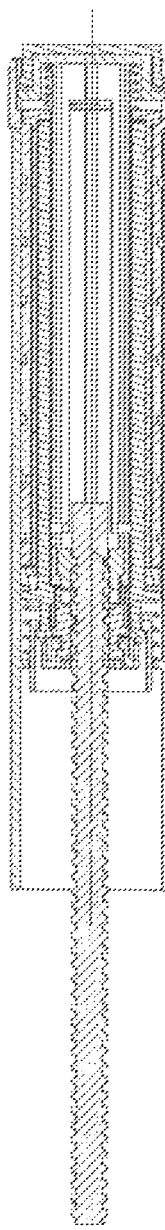
FIG. 16c shows a cross sectional view of the drive and dosing device shown in FIG. 16a taken along the line S-S in FIG. 16b.

FIGS. 16a-16c shows the drive and dosing device after dispensing the dose which has been set in FIGS. 15a-15c. A rotation of the dose knob 10 in the first rotation direction is not possible anymore.

Positioned between the nut 13 and the housing 4 is a unidirectional coupling 71, 72 (e.g., a ratchet) which in its active status tolerates a rotation of the nut 13 relative to the piston rod 19 in the second direction only and which blocks a rotation in the first direction. Removing the cartridge or the cartridge holder from the drive and dosing device deactivates the unidirectional coupling 71, 72, particularly by decoupling the coupling structures 73, 74 and/or coupling structures 71, 72.

The unidirectional coupling 71, 72 has a first coupling structure 71 which is established at a part of the housing 4, or at a part of an element attached to the housing, here a ring-shaped element 75. The second coupling structure 72 is disposed at the drive sleeve 8 and includes at least one saw tooth, particularly pointing in the proximal direction that, when it engages the first coupling structure 71, allows only a rotation of the drive sleeve 8 in the second direction but not in the first rotation direction.

The cartridge or the cartridge holder (not shown) are connected with the drive sleeve 8 such that the drive sleeve 8 is moved relative to the housing 4 in the distal direction upon removing the cartridge from the drive and dosing device and it is moved in the proximal direction relative to the housing 4 upon fixation of the cartridge to the drive and dosing device. A switching element 12 is located between the cartridge holder and the drive sleeve 8 or between the cartridge and the drive sleeve 8, which is actuated by the cartridge holder or the cartridge such that the switching element is moved along the longitudinal axis L. Switching element 12 and drive sleeve 8 are connected such that the drive sleeve 8 follows the movements of the switching member 12 along the longitudinal axis L.

If the cartridge holder is removed from the drive and dosing device then the couplings 71, 72 and/or 73,74 are decoupled such that the nut 13 is rotatable in the first direction relative to the housing 4 (see, e.g., FIGS. 17a-17c). The piston rod 19 can be moved back into the drive and dosing device by applying a force in the proximal direction on the piston rod 19 whereby the nut 13 rotates in the first direction relative to the housing 4. The stop element 20 is taken along by the piston rod 19 during the device resetting and the stop element 20 does not conduct any movements relative to the piston rod 19.

A cartridge and/or a cartridge holder can be attached again to the drive and dosing device after the piston rod 19 has been completely reset (see, e.g., FIGS. 18a-18c) whereby the switching element 12, and there with the drive sleeve 8, is moved in the proximal direction relative to the housing 4. As a consequence, the couplings 71, 72 respectively 73, 74 are coupled so that a rotation of the nut 14 is only possible in the second direction but not in the first direction.

A third embodiment is shown in FIGS. 19-30 for a drive and dose setting mechanism with a housing 4, 18 including an external housing 18 and a housing insert or mechanic holder 4. An exploded view is presented in FIG. 19, a cross section in FIG. 20 and a detail in FIG. 21, all for the device in its initial state. The mechanic holder 4 or housing insert is fixed (e.g., rotationally and axially fixed) with respect to the external housing 18. The housing insert 4 has an external thread 4a that engages an internal thread 9c of the scale drum 9 such that the scale drum 9 can be screwed along the longitudinal axis L of the housing 4, 18. At the proximal end of the scale drum is located the dose knob 10 and between the dose knob 10 and the scale drum 9 is an overload clutch 45. The overload clutch 45 is designed as a hollow cylinder with external teeth 45a located at the proximal end and a connector cut-out 45b at its distal end. The overload clutch is axially and rotationally secured with respect to the scale drum 9 for example by a snap fit connection, glued or welded together thereby using the cut out 45b for securing the anchorage. The dose knob 10 has a rim 10c that is concentrically arranged around the proximal end of the overload clutch 45 and internal teeth 10d located on the inside of the rim 10c such that the teeth 10d engage the teeth 45a located at the proximal end of the overload clutch 45. The teeth 10d, 45a are arranged parallel to the longitudinal axis L of the drive and dosing mechanism and allow for relative axial movement and are rotationally secured up to a threshold torque value when the meshing teeth start to ratchet. A dose knob cover 10f surrounds the dose knob 10 and the two parts are rotationally and axially locked together and can be considered to mechanically behave as a single part. On the outside of the dose knob cover 10f is a grip surface 10g, which is used to rotate the dose knob 10 with respect to the housing 4, 18. The rotation of the dose knob 10 is transmitted to the scale drum 9 via the overload clutch 45. The set dose will be increased upon rotation of the dose knob 10 in the first direction and the set dose will be decreased upon rotation in the second direction which is opposite to the first direction. Rotation of the dose knob 10 in the first direction ensures that the scale drum is screwed out of the proximal end of the housing (see, e.g., FIG. 22) and rotation in the second direction moves the scale drum back into the housing 4, 18. The overload clutch mechanism 45a, 10d can be activated when the user wants to set a dose which exceeds the amount of product present in the cartridge. The stop element 20 is in the stop position and the engagement of the catch 20a and stop limiter 15a prevents rotation of the scale drum 9 in the first direction for increasing the dose (see, e.g., FIG. 26). If the user nevertheless tries to increase the dose, the ratchet coupling 45a, 10d is activated and the meshing teeth can ratchet therewith preventing that an excessive torque is transmitted from the dose knob 10 to the scale drum and finally to the stop limiter. The members 45a and/or 10d of the ratchet coupling are present on resilient arms or members that enable movement in the radial direction to ensure the ratchet functionality. The resilient arms are not shown in FIG. 19, 20 or 25. The overload protection can be a unidirectional coupling or a bidirectional coupling. The overload protection can also be activated for setting an individual dose when the amount of product present in the cartridge is sufficient and the scale drum is in the maximum dose position and the user tries to rotate the dose knob in the first direction or when the scale drum is in the zero dose position and the user attempts to rotate the dose knob in the second rotation direction.

The pen according to the third embodiment features a pen cap 1 with a clip 1a. The external housing 18 has a display or viewing window 18a for viewing the set dose on the scale drum 9 (see, e.g., FIG. 19). The scale drum has the dose values printed on the outer surface. The dose values are consecutively arranged along a helix-shaped curve. The arrangement on the outside of the scale drum and the interaction with the viewing window while rotating the dose knob may be the same as the first embodiment described above. In the third embodiment, the dose knob and actuation functionalities are combined. Thus for setting a dose, the dose knob 10 is rotated and therewith also the scale drum 9 is rotated with respect to the housing due to the threaded engagement 4a, 9c between the housing insert 4 and the scale drum 9, and/or the matching thread connection 7b/6b between the dose sleeve 7 and the clutch 6, respectively. The dose knob also functions as an actuation element which can be displaced in the distal direction along the actuation distance relative to the scale drum 9 (compare, e.g., FIGS. 22 and 23). The ratchet coupling 45a, 10d transmits rotational forces up to a threshold value and allows for axial movement between the dose knob 10 and the overload clutch 45. When the user pushes the dose knob 10 in the distal direction, the dose knob moves over the actuation distance towards the scale drum against the resilient force of the reset spring 40 and thereby decoupling the ratchet coupling 45a, 10d, which allows for relative rotational movement between the scale drum and the dose knob (see, e.g., detailed cross sections in FIGS. 25a and 25b). Upon releasing the dose knob 10, the dose knob moves in the proximal direction due to the reset spring 40 from the actuated into the non-actuated position. The dose knob 10 can be depressed with the thumb from the non-actuated into the actuated position and upon further pressing, when the scale drum starts to rotate due to the threaded engagement with the housing insert 4, the dose knob moves towards the rearward end of the device. The dose knob 10, which is in contact with the users thumb, is not rotating whereas the scale drum rotates. In the first embodiment having a separate dose button and a dose knob, the user that grabs the housing and pushes the dose button and the scale drum back into the housing (whereby the dose knob rotates versus a non-rotating dose button) has the potential for a brake drum effect where the thumb pushing the dose button potentially frictionally affects the rotation of the dose knob. By combining the two functionalities in the dose knob of the third embodiment, the brake drum effect can be avoided.

Figure 22:
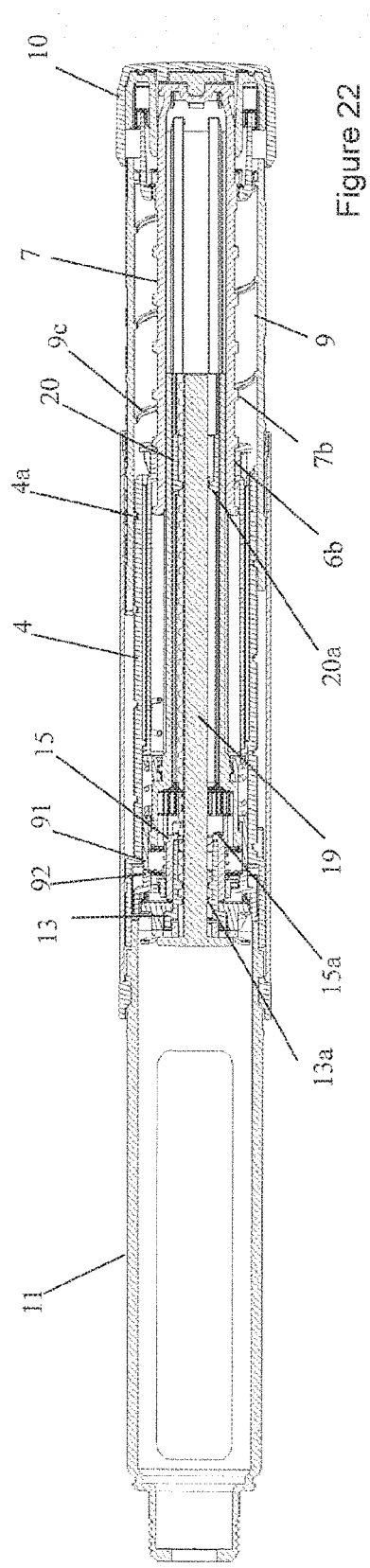
FIG. 22 is a cross sectional view of a drive and dosing device according to the third embodiment, after setting of a dose.
Figure 24:
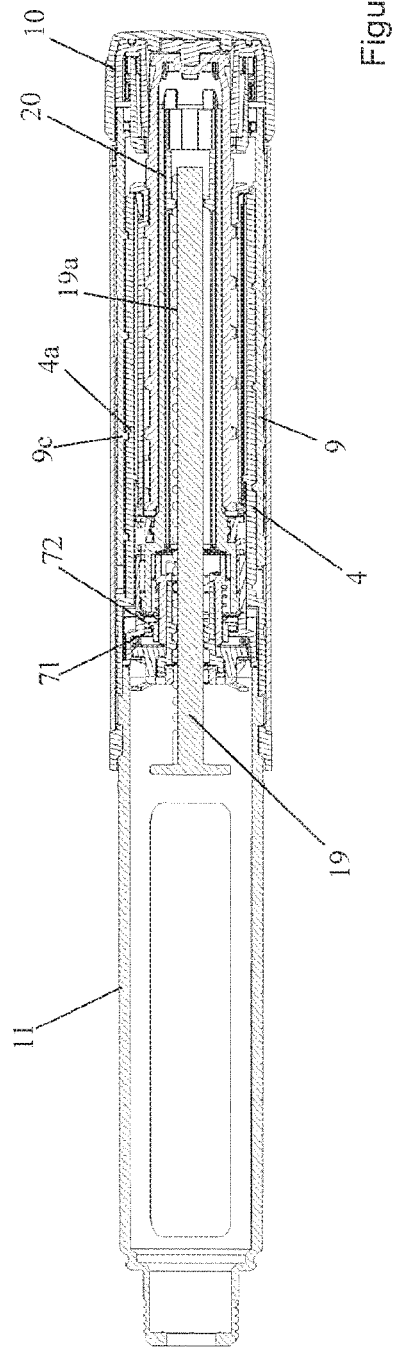
FIG. 24 is a cross sectional view of a drive and dosing device according to the third embodiment after dispensing of the set dose and having an actuated dose knob.
Figure 26:
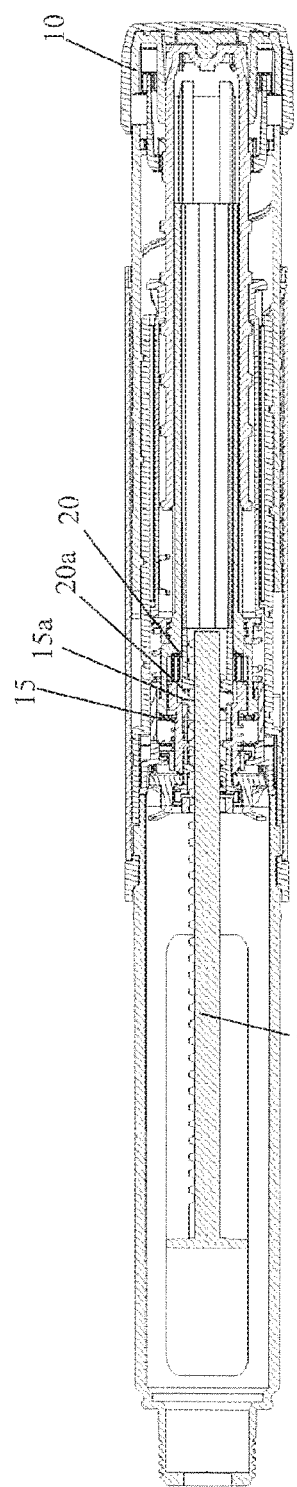
FIG. 26 is a cross sectional view of a drive and dosing device according to the third embodiment in which the setting of a higher dose is prevented by the stop element being in the stopping position.
Figure 27:
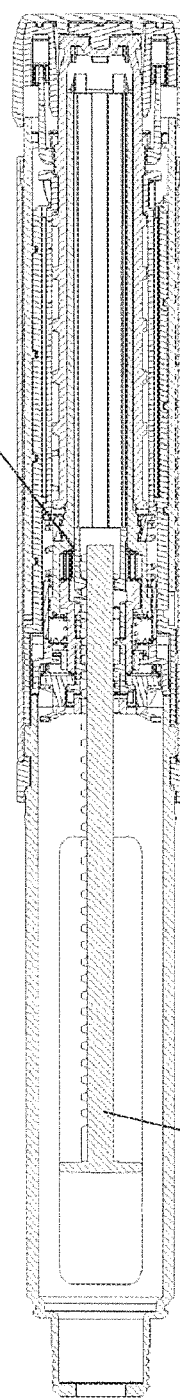
FIG. 27 is a cross sectional view of a drive and dosing device according to the third embodiment after the dose set in FIG. 26 has been dispensed.
Figure 28:
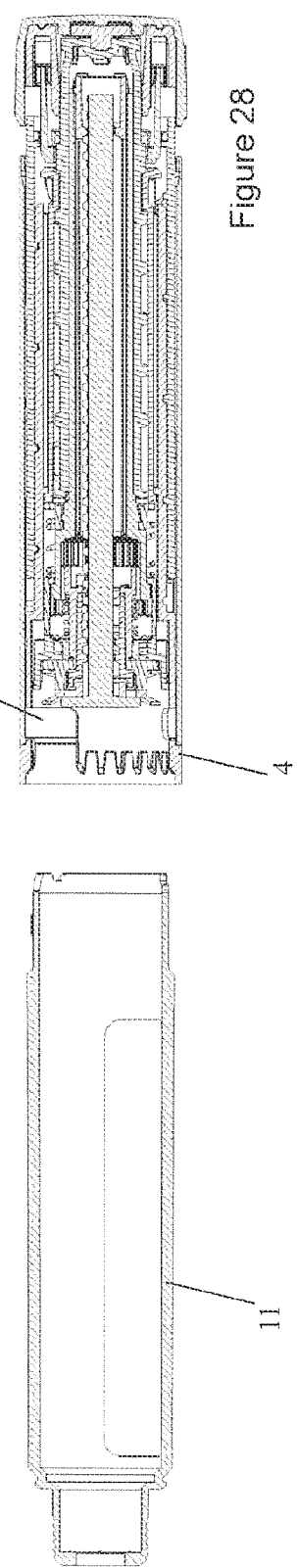
FIG. 28 is a cross sectional view of a drive and dosing device according to the third embodiment after the cartridge holder has been removed.
Figure 29A:
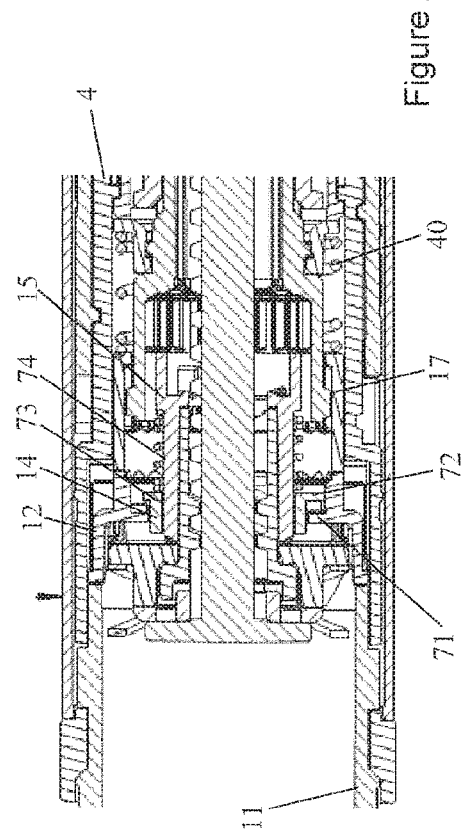
FIG. 29a is a detail cross sectional view of a drive and dosing device according to the third embodiment with the device in an initial state with cartridge holder attached to the drive and dosing mechanism.
Figure 29B:
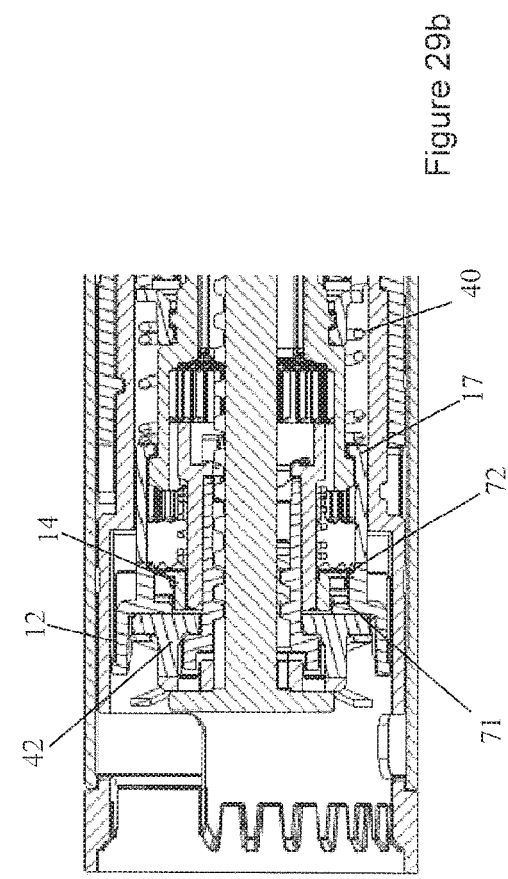
FIG. 29b is a detail cross sectional view of a drive and dosing device according to the third embodiment with the device in an initial state with cartridge holder removed from the drive and dosing mechanism.

For dispensing the set dose, the dose knob 10 is pressed further in the distal direction such that the dose knob 10 moves in the distal direction and the dose scale 9 rotates and is screwed back into the housing 4, 18. FIG. 24 shows the embodiment after the dose set in FIG. 22 is dispensed.

The location of the cartridge and cartridge holder 11 may be the same as in the first embodiment. The cartridge 11a has a septum at its distal end which can be pierced by a needle for dispensing a product. The cartridge also has a plug which can be moved in the distal direction for dispensing the liquid product present between the plug and the septum. The plug of the cartridge is operatively coupled to the piston rod 19 and the piston rod 19 has a multiple threading 19a on the outside which engages an internal threading 13a of the rotating member 13, 15. The rotating member of the third embodiment includes two parts, a threaded nut or drive nut 13 and a drive nut socket 15 which are axially and rotationally connected to each other. Between the nut 13 and the drive nut socket 15 is a circumferential notch which engages the bearing disc 42 (see, e.g., FIG. 21). The bearing disc 42 is axially and rotationally secured to the housing 18 by the arms 42b that engage with matching units on the inside of the housing insert 4 in a snap-fit connection. Therewith the rotation member 13, 15 is axially locked, but rotationally free with respect to the housing 4, 18 and axial forces acting on the rotation member 13, 15 are guided to the housing 4, 18 via the bearing disc 42.

The functioning of the linear slide 2, which ensures that the piston rod 19 can slide but not rotate with respect to the housing, is described in detail above. The guiding bushing 2*a* of the linear slide 2 matches the longitudinal notch 19*d* of the piston rod 19 and, because the linear slide is rotationally secured with respect to the housing, ensures that the piston rod 19 can slide but not rotate with respect to the housing 4, 18.

During dose setting, the rotating member 13, 15 is rotationally secured with respect to the piston rod 19 (e.g., does not rotate with respect to the piston rod 19). During dose delivery, the rotation member is rotated relative to the piston rod 19 and/or the housing 4, 18, preferably in the second rotation direction. The rotation member 13, 15 follows, upon actuation of the dose knob 10, the rotation of the scale drum 9 and/or dose sleeve 7 during dose delivery. The rotation member 13, 15 engages with the internal thread 13*a* the external thread 19*a* of the piston rod. Since the piston rod 19 is axially guided by the bushing 2*a*, the piston rod will translate in the distal direction for dispensing the set dose. As mentioned above, the rotation member 13, 15 includes two parts that are connected to each other and behave as a single part, however each part is optimized from a materials perspective to the specific tribological and/or mechanical needs. The threaded nut 13, may be made from, for example, Teflon, PTFE, a fluorocopolymer, with or without additives to reduce the frictional losses. The drive nut socket 15 may be made from a high strength polymer with or without fiber reinforcement.

Comparable to the first embodiment, a notch exists between the two components of the rotation member 13, 15 and the notch engages a part that is fixed to the housing (e.g., bearing disc 42). The notch of the rotation member 13, 15 engages the bearing disc 42 and ensures that the rotation member 13, 15 is rotatable but axially non-displaceable with respect to the housing 4, 18.

Figure 23:
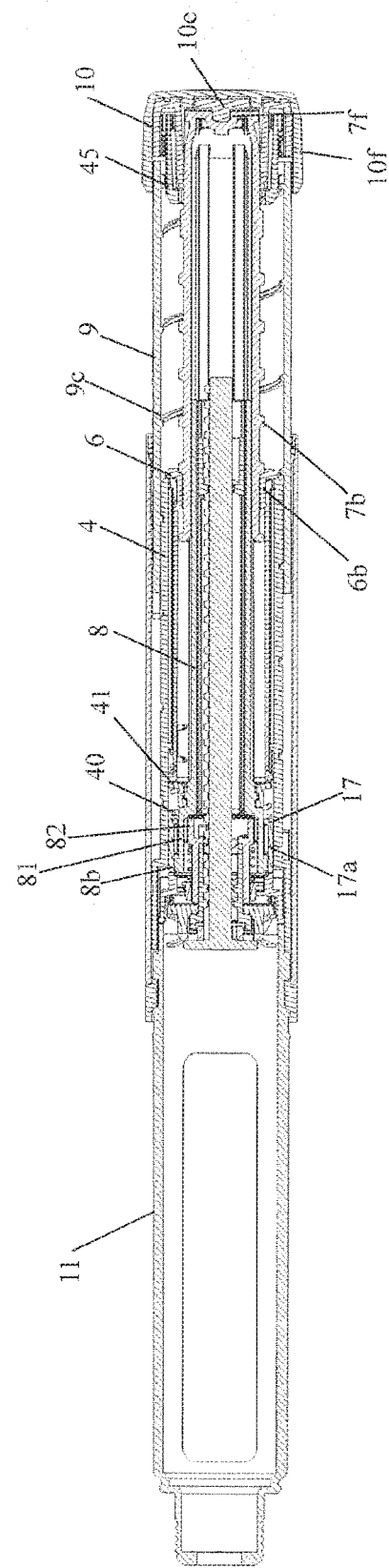
FIG. 23 is a cross sectional view of a drive and dosing device according to the third embodiment, after setting of a dose and actuation of the dose knob.

The dispense coupling 81, 82 is closed upon depressing the combined dose knob 10 and is opened upon release of the dose knob 10. The dispense coupling 81, 82 couples the rotation member 13, 15 torque-proof with the scale drum 9 and/or dose sleeve 7 and/or drive sleeve 8 when the dispense coupling 81, 82 is closed (as shown in FIGS. 22 and 23). When the dose knob 10 is released, the coupling 81, 82 is opened and the rotation member is rotationally decoupled from the dose sleeve 7 and/or drive sleeve 8 and/or scale drum 9. Upon releasing the dose knob 10, the dose knob 10 moves in the proximal direction thereby the dose knob 10 is coupled to the scale drum via the overload clutch coupling 45*a*, 10*d*.

The dispense coupling 81, 82 includes two coupling structures 81 and 82 respectively that are described in more detail above for the first embodiment. The two coupling structures are brought in a rotationally secured engagement when the coupling is closed. The coupling structure 81, 82 comprises a reset spring 40 which spring force tends to disengage the first coupling structure 81 from the second coupling structure 82. The dispense coupling 81, 82 is closed upon actuation of the combined dose knob 10 thereby compressing the reset spring 40.

The reset spring 40 also serves the purpose of resetting the dose knob 10 from the actuated into the non-actuated position, thereby closing the coupling 45*a*, 10*d*

In the third embodiment, the first and second coupling structures 81 and 82 include circumferentially arranged teeth oriented along the longitudinal axis L of the device, comparable to the first example. The teeth of the structures are configured such that they can axially slide over each other and interlock to form a torque-proof connection. The second coupling structure 82 is rotationally connected to, preferably part of the rotation member 13, 15, more preferably part of the drive nut socket 15.

Comparable to the first example, the first coupling structure 81 is present at the distal end of the drive sleeve 8 and the drive sleeve 8 is kinematically or geometrically arranged between the dose knob 10 and the rotation member 13, 15. The drive sleeve 8 is moved in the distal direction with respect to the housing 4, 18 when the dose knob 10 is moved in the distal direction during actuation from the non-actuated to the actuated position. Upon release of the dose knob 10, the drive sleeve 8 will be displaced in the proximal direction via the reset spring 40 thus decoupling the coupling 81, 82. A disc 41 is located between the coupling structure 81 and the proximal end of the drive sleeve 8 and the disc 41 is axially locked but rotatable with respect to the drive sleeve 8. The distal surface of the disc 41 abuts the proximal end of the reset spring 40 and energy stored in the reset spring 40 is released when the dose knob 10 moves from the actuated to the non-actuated position thus moving the drive sleeve 8 in the proximal direction via the disc 41.

Between the drive sleeve 8 and the dose knob 10 is a dose sleeve 7. The dose sleeve may be rotationally secured but axially slidable with respect to the drive sleeve 8 due to a key-cam interaction including longitudinal grooves and/or protrusions present between the dose sleeve 7 and the drive sleeve 8; details are described above in the first embodiment.

The dose sleeve 7 has a threading 7*b* on the outside surface and the ends of the thread provide for the stop zero dose and stop maximum dose, respectively. The coupling sleeve 6 is located between the housing 4, 18 and the dose sleeve 7 having an internal thread 6*b* that engages the outer thread 7*b* of the dose sleeve 7. The thread ends interact with the internal thread 6*b*, or internal thread segment 6*b*, to form the stop maximum dose or stop zero dose arresters, comparable to the first embodiment.

The dose sleeve 7 in the third embodiment is axially fixed with respect to the dose knob 10 both during dose setting and dose dispensing. The bottom surface 10*e* of dose knob cover 10*f* touches the proximal end surface 7*f* of the dose sleeve 7 to transmit the axial forces (see, e.g., FIG. 20). During dose setting, the dose knob 10 is axially and rotationally locked with respect to the dose sleeve 7. During dose delivery, the dose sleeve 7 is axially coupled but rotationally decoupled from the dose knob 10. During dose delivery, the dose sleeve 7 rotates in the second direction whereas the dose knob 10 does not rotate. The contact surface between end surface 7*f* and bottom surface 10*e* is shaped such to minimize the frictional losses during dose delivery. In the third embodiment, the bottom surface 10*e* has a protrusion that engages a recess at the distal end surface 7*f* (see, e.g., FIGS. 25*a* and 25*b*).

Between the housing 4, 18 and the dose sleeve 7 is the coupling sleeve 6 which is engaged with the housing 4, 18 such that the coupling sleeve 6 is rotationally secured but axially slidable with respect to the housing 4, 18. The engagement is described above in the first example and is a key-groove interaction between the outside surface of the coupling sleeve 6 and the inside of the housing 4, 18. On the inside of the coupling sleeve 6 is the internal thread 6*b* that engages the outside thread 7*b* of the dose sleeve 7. Upon actuation of the dose knob 10, the coupling sleeve 6 is moved in the distal direction due to the threaded engagement between the coupling sleeve 6 and the dose sleeve 7 (compare, e.g., FIGS. 22 and 23). The axial movement of the coupling sleeve 6 is transmitted to the drive sleeve 8 via the disc 41.

A unidirectional coupling 71, 72, 73, 74 is located in the housing 4, 18 and is generally referenced to as coupling 70. During dose setting and/or delivery the unidirectional coupling 70 prevents a rotation of the rotation member 13, 15 in the first rotation direction relative to the housing 13, 15 and/or piston rod 19 whereas it permits a rotation in the second direction. The unidirectional coupling 70 can be shaped as a ratchet. The unidirectional coupling essentially functions identical to the first embodiment and prevents frictional forces during dose setting from being transmitted to the rotation member 13, 15 and/or prevent the piston rod from moving in the proximal direction due to elastic forces acting from the plug of the cartridge upon the piston rod 19.

The unidirectional coupling 70 can be designed as a permanent coupling for a disposable pen or as a releasable coupling for a reusable pen (e.g., when an empty cartridge 11*a* is replaced by a new and full cartridge). During exchange of the cartridge 11*a* it is preferred that the rotation member 13, 15 is allowed to rotate in the first rotation direction relative to the housing 4, 18 such that the piston rod can move in the proximal direction and can be reset in its original position.

The unidirectional coupling 70 has a first coupling structure 71 and a second coupling structure 72, whereby the first and second coupling structures form a ratchet allowing for relative rotation in one direction only. The first coupling structure 71 is, comparable to the first embodiment, directly or indirectly secured with respect to the housing 4, 18, or at least rotationally locked to the housing, for example through bearing disc 42. The second coupling structure 72 can be formed by the rotation member 13, 15, preferably by drive nut socket 15, more preferably by a part that is rotationally, preferably permanently rotationally connected to the rotation member 13, 15. In the third embodiment, the coupling structure 72 is preferably shaped onto coupling ring 14 (see, e.g., FIG. 29*a*). The coupling ring is preferably rotationally locked and axially moveable with respect to the rotation member 13, 15, during dose setting, dose dispensing and resetting of the device. The first and second coupling structures 71, 72 are engaged by a spring, preferably dose spring 5. The dose spring 5 serves the purpose only for engaging the first and second coupling structures 71, 72 and is not also used for resetting the dose knob 10 or for generating the clicks during dose setting or for moving into—or out of— the reset mode for exchanging a cartridge. The dose spring 5 is optimized, preferably for the sole purpose of the engagement of the first and second coupling structures 71, 72. Preferably, the first and the second coupling structures 71, 72 encompass circumferentially arranged saw tooth structures. The teeth of the two coupling structures preferably point to each other. The teeth of the first structure 71 preferably point in the proximal direction and the teeth of the second structure 72 preferably point in the distal direction. The saw tooth structures 71, 72 have a steep and flat face which are pressed together by the dose spring 5. The saw tooth structures are arranged such that rotation of the second saw tooth structure 72 in the first direction relative to the first coupling structure 71 is prevented. Thereby rotation of the coupling ring 14 in the first direction is prevented and therewith also the rotation in the first direction of the rotation member 13, 15 due to the engagement of the third coupling structure 73 and the fourth coupling structure 74. The third coupling structure 73 includes internal teeth on the coupling ring 14 that engage with external teeth of the fourth coupling structure 74 present on the outside of the rotating member 13, 15. The coupling structures 73 and 74 are arranged such that axial displacement between the two members is allowed whereas rotational movements are prevented.

For setting a dose, the user rotates the dose knob cover 10*f* and therewith the dose knob 10 which is rotationally locked to the dose knob cover 10*f*. The user rotates the dose knob 10 in the first direction and the dose knob 10 is rotated out of the proximal end of the housing 4, 18 together with the scale drum 9 (FIG. 22). The set dose can be read from the dose scale 9*b* through the viewing window 18*a* of the housing 18. The dispense coupling 81, 82 is decoupled.

For dispensing a set dose, the dose knob 10 is pressed in the distal direction versus the scale drum 9 and/or housing 4, 18 along an actuation distance (see, e.g., FIG. 23). Thereby the overload coupling 45*a*, 10*d* is decoupled, which rotationally decouples the dose knob 10 from the scale drum 9 (see, e.g., FIGS. 25*a* and 25*b*). The dose sleeve 7 is also displaced versus the housing 4, 18 along the actuation distance of the dose knob 10. The coupling sleeve 6 is also displaced in the distal direction over the same actuation distance, this due to the threaded engagement 7*b*, 6*b* that exists between the dose sleeve 7 and the coupling sleeve (or clutch) 6. The coupling sleeve 6 pushes the drive sleeve 8 in the distal direction over the actuation distance of the dose knob 10 via the disc 41 which is axially locked to the drive sleeve 8. The dose spring 5 is compressed over the actuation distance and the first coupling structure 81 present at the drive sleeve 8 is coupled to the second coupling structure 82 present at the rotation member 13, 15 thereby forming a torque-proof engagement.

Upon further pressing the dose knob 10 in the distal direction, the dose knob is screwed back into the housing 4, 18 along a distance corresponding to the set dose (FIG. 24). Hereby the scale drum 9 rotates in the second direction due to the non-self-locking thread connection 4*a*/9*c* and/or 7*b*/6*b*, whereas the dose knob does not rotate since the dose knob 10 is rotationally decoupled from the scale drum 9. The set dose value at the dose scale 9*b* counts back as the scale drum 9 rotates back into the housing and the rotational movement (e.g., torque in the second direction is transferred to the dose sleeve 7, the drive sleeve 8 and finally to the rotation member 13, 15 via the coupling 81, 82). The rotation of the rotation member 13, 15 in the second direction is translated into an axial movement of the piston rod 19 in the distal direction whereby the piston rod 19 slides though the linear slide 2. The flange 19*b* at the distal end of the piston rod 19 pushes against the plug of the cartridge for dispensing the set dose. The piston rod 19 moves along the longitudinal axis L over a dispensing distance and the dose knob 10 moves along a dose setting distance whereby the dose setting distance is above the dispensing distance. The differences in dose setting distances and dispensing distances are governed by different pitches of the threads of the scale drum (or dose sleeve) and piston rod, respectively. The different pitches result in a gearing from the force applied to the dose button to the plug of the cartridge.

The device of the third embodiment has a stop element 20 comparable to the first embodiment which prevents setting a dose that exceeds the dispensable volume present in the cartridge 11*a*. The stop element 20 is a nut with internal thread 20 which rotates along the piston rod 19 during dose setting and correction and which returns to its original position with respect to the piston rod during dose dispensing (see, e.g., FIGS. 26 and 27). Thereby the distance between the catch 20a of the stop nut and the stop limiter 15a of the rotation member 13, 15 decreases upon repeated dose setting and dispensing. When the stop nut 20 is in the stopping position (e.g., when the catch 20a abuts the stop limiter 15a) the setting of a dose is prevented which exceeds the amount present in the cartridge 11a. The functioning of the stop element 20 of the third embodiment may be identical to the first embodiment and is described in more detail above (see, e.g., FIGS. 6 and 7 of the first embodiment).

The cartridge holder 11 holding the cartridge can be the same as the cartridge holder 11 of the first embodiment. The cartridge holder 11 may be releasable from a drive and dosing mechanism that is intended for a reusable injection device and the connector between the drive and dosing mechanism and the cartridge holder can be a bayonet type of connector (see, e.g., FIG. 28). The protrusion 11b of the cartridge holder 11 is first axially inserted into the axial section of the bayonet slot 4b and subsequently locked into the circumferential section of the bayonet slot 4b by rotation of the cartridge holder 11 and/or the housing 4, 18. The functioning for closing and opening of the bayonet connector is identical to the first embodiment described previously.

The cartridge that is inserted into the cartridge holder 11 is subjected to dimensional tolerances, particularly with respect to the length of the cartridge (cartridge not shown in FIGS. 19-29 of the third embodiment). The device has a cartridge spring 3 which is present between the cartridge and the bearing disc 42. The bearing disc 42 is axially locked to the housing 4, 18 and, upon insertion of a new cartridge in the cartridge holder 11 and attachment to the housing, the cartridge is sandwiched between the distal end of the cartridge holder and the cartridge spring 3. The latter is compressed thus fixing the cartridge and compensating for tolerances in the length of the cartridge.

For the insertion of a new cartridge in a reusable device, the piston rod 19 may be reset to its original position. For that, the piston rod may be enabled to slide back into the drive and dosing mechanism and, as a result, the rotation member may rotate in the first rotation direction. This rotation is prevented during dose setting and dose delivery by the unidirectional coupling 70 and therefore this coupling may be switched into an inactive state during reset of the piston rod 19. For this, the first coupling structure 71 is decoupled from the second coupling structure 72 when the cartridge holder is removed from the housing 4, 18. During normal operation and during reset, the third and fourth coupling structures 73, 74 remain engaged in the third embodiment (see, e.g., FIG. 29a). The cartridge holder 11 is coupled such to the first coupling structure 71 that the first coupling structure 71 disengages from the second coupling structure 72 when the cartridge holder 11 is released from the drive and dosing device, particularly when the cartridge holder 11 is moved in the distal direction relative to the housing 4, 18. The coupling 70 is than in its inactive state (see, e.g., FIG. 29b). On the reverse, when the cartridge holder 11 is attached to the drive, then the first coupling structure 71 engages the second coupling structure 72, particularly, the first coupling structure 71 moves in the proximal direction thereby engaging the second coupling structure 72. The first coupling structure 71, preferably present at the switching element 12 described below, can be moved against the force of the reset spring 40 in the proximal direction when attaching the cartridge holder. The coupling 70 is in the active state. Upon releasing the cartridge holder from the drive and dosing mechanism, the first coupling structure 71 moves in the distal direction due to the resilient forces of the reset spring 40.

The first coupling structure 71 is preferably present at the switching element 12 and the switching element 12 is axially slidable but rotationally secured with respect to the housing 4, 18 and thus can move along the longitudinal axis L of the drive and dosing mechanism. In the third embodiment, the switching element 12 is coupled such with the cartridge holder 11 that the switching element 12 moves in the proximal direction when a new cartridge has been inserted and the bayonet connection between the cartridge holder 11 and the housing 4, 18 is closed (compare FIGS. 29a and 29b). The switching element 12 moves in the distal direction when the cartridge holder 11 is rotated with respect to the housing 4, 18 for releasing the bayonet connection. The switching element 12 has protrusions 12d that engage a sloped activation surface 11c at the proximal end of the cartridge holder 11. Inserting the cartridge holder 11 into the housing 4, 18 followed by a rotation with respect to the housing for closing the bayonet connector ensures that the sloped surface of the cartridge pushes the switching element 12 in the proximal direction via the protrusions 12d. When the bayonet connector is closed (e.g., when the protrusion 11b of the cartridge holder 11 rests in the circumferential end of the bayonet slot 4b) the protrusion 12d of the switching element will rest in a recess present at the end of the activation surface 11c. The engagement of the elements lie and 12d can be accompanied by a tactile and/or audible signal. The switching element 12 is biased by the reset spring 40 either directly or more preferably via an intermediate sleeve, preferably the ratchet ring 17. Upon releasing the cartridge holder 11 from the drive and dosing mechanism, the switching element 12 is moved in the distal direction by the spring forces acting from the reset spring 40.

The coupling 70 is in its inactive state when the cartridge holder 11 is released from the drive and dosing device. The piston rod 19 can be reset and pushed back into the drive and dosing mechanism since the rotation of the rotation member 13, 15 in the first direction with respect to the housing is allowed provided that the coupling 70 is non active. The piston rod is rotationally secured with respect to the housing 4, 18 via linear slide 2 and the piston rod 19 slides back into the housing without rotating. The stop element 20 is also moved in the proximal direction, as mentioned above for the first embodiment.

The automatic reset-retraction of the piston rod and/or automatic advancement of the piston rod during exchange of a cartridge is not shown in the drawings and is described hereafter. For the automatic advancement of the piston rod after exchange of a cartridge, the piston rod 19 advances in the distal direction when the cartridge holder and cartridge have been removed from the housing. For example a compression spring can be present between the distal end of the piston rod, for example the flange 19b, and the linear slide 2 or housing insert 4. After insertion of a new cartridge in the cartridge holder 11 and attachment of the cartridge holder to the drive and dosing mechanism, the plug of the cartridge pushes the piston rod in the proximal direction against the resilient forces of the spring and after attachment closure of the bayonet connection between the cartridge holder 11 and the housing 4, 18, the flange 19b of the piston rod abuts the proximal end of the plug of the cartridge therewith avoiding the need for a priming operation to close the gap between the piston rod and the cartridge plug. Other variations of the concepts can be introduced such as for example, a spiral spring present between the rotation member 13, 15 and the housing 4, 18. The spring energy stored facilitates a rotation of the rotation member 13, 15 in the second direction when the coupling 70 is decoupled (e.g., when the cartridge holder has been removed from the drive and dosing mechanism). Even if the piston rod is not in the most distal position, either the compressive spring forces mentioned before or the spiral spring forces acting on the rotation member 13, 15 will advance the piston rod to the most distal position. During insertion of a new cartridge, the rotation of the rotation member 13, 15 in the first direction required to reset the piston rod 19 will tension the spiral spring and a contact between the flange 19b of the piston rod 19 and the plug of the cartridge is guaranteed after the reset operation before setting and dispensing a dose from the new cartridge. For the automatic retraction of the piston rod during the reset operation a spiral spring can be, for example, present between the rotation member 13, 15 and the housing 4, 18 and the spiral spring is tensioned during repeated setting and dispensing of doses (e.g. during advancement of the piston rod). The energy stored in the spiral spring promotes a rotation of the rotation member 13, 15 in the first direction, thus when the coupling 70 is decoupled during reset of the device, the rotation member 13, 15 is rotated in the first direction and results in a retraction of the piston rod prior to insertion of a new cartridge. As an alternative, a spring can be present and attached to the piston rod 19 and the housing 4, 18. Such a spring is tensioned during advancement of the piston rod (e.g., repeated dispensing of doses and energy stored in the tension spring is released during reset of the device resulting in an automatic retraction of the piston rod 19).

Figure 19:
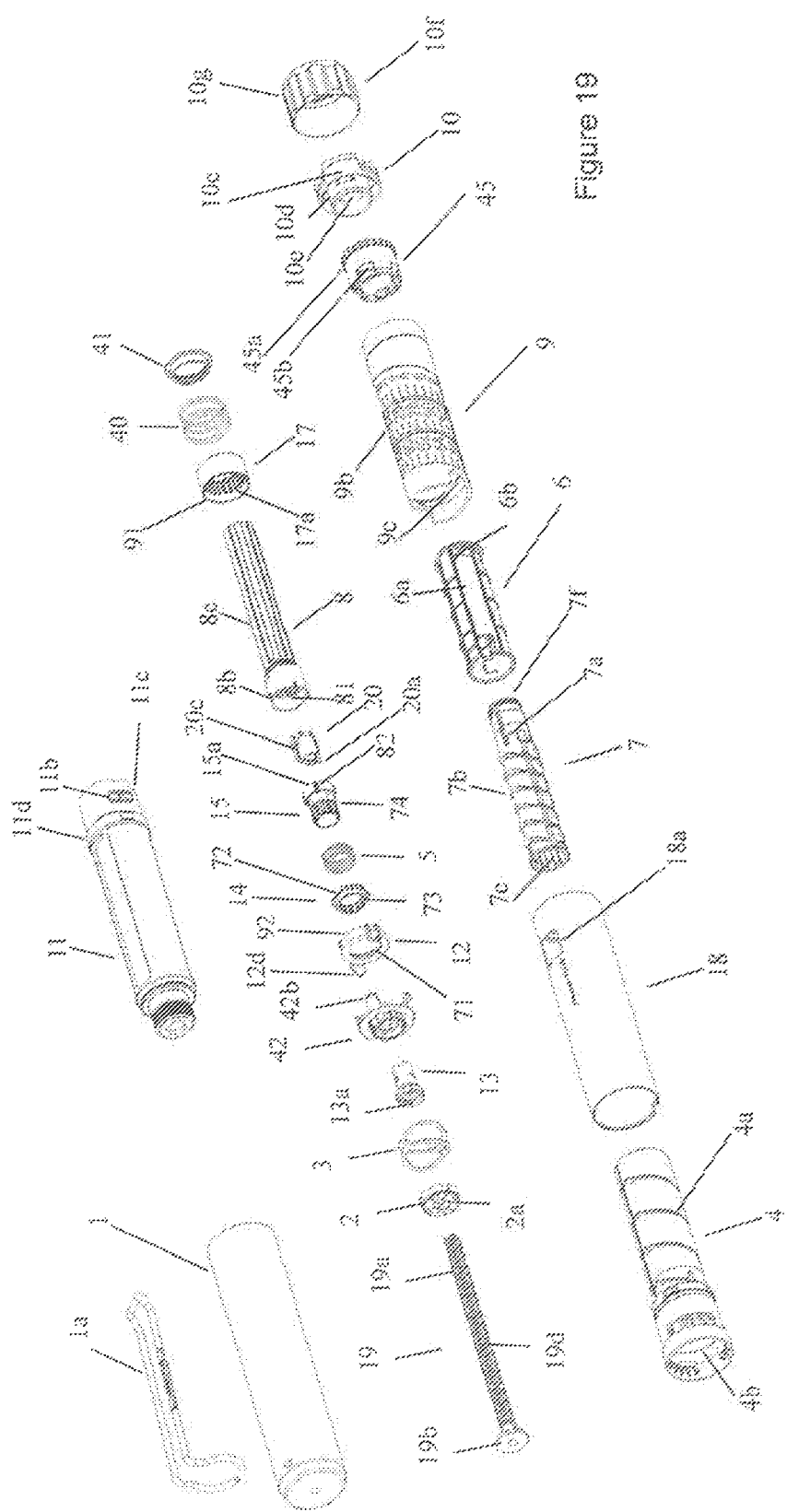
FIG. 19 is an exploded view of the individual parts of a drive and dosing device according to a third embodiment.
Figure 20:
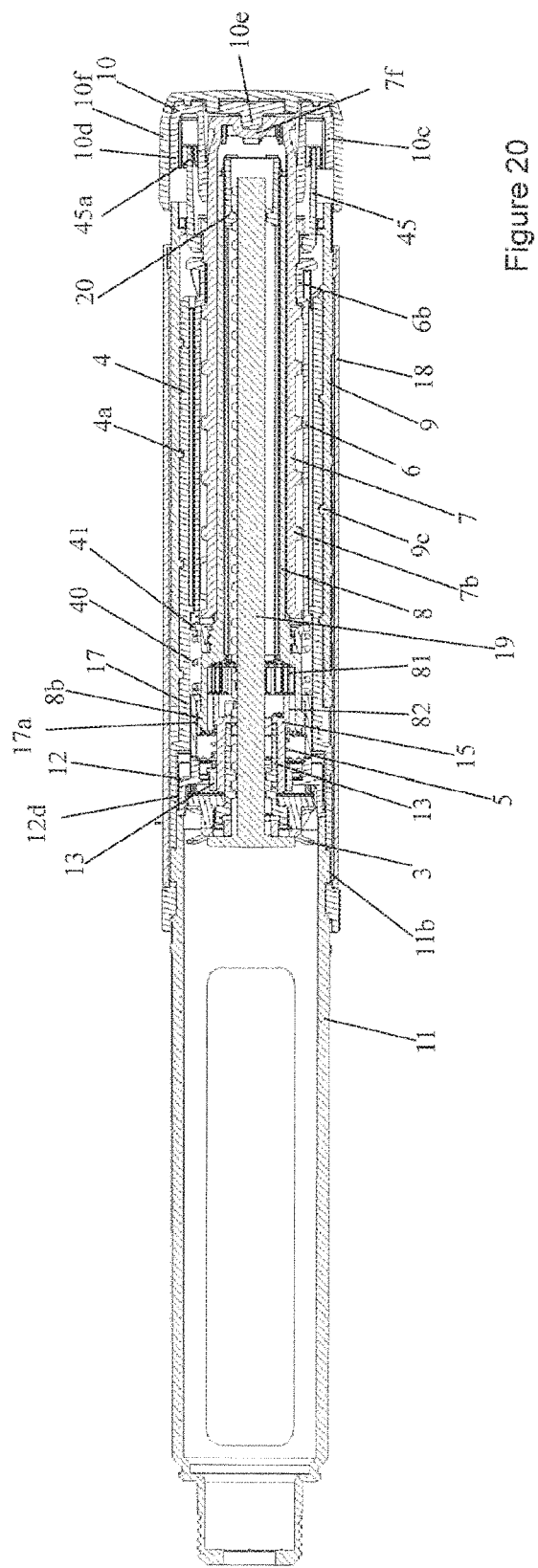
FIG. 20 is a cross sectional view of a drive and dosing device according to the third embodiment in an initial state before setting of a dose.
Figure 21:
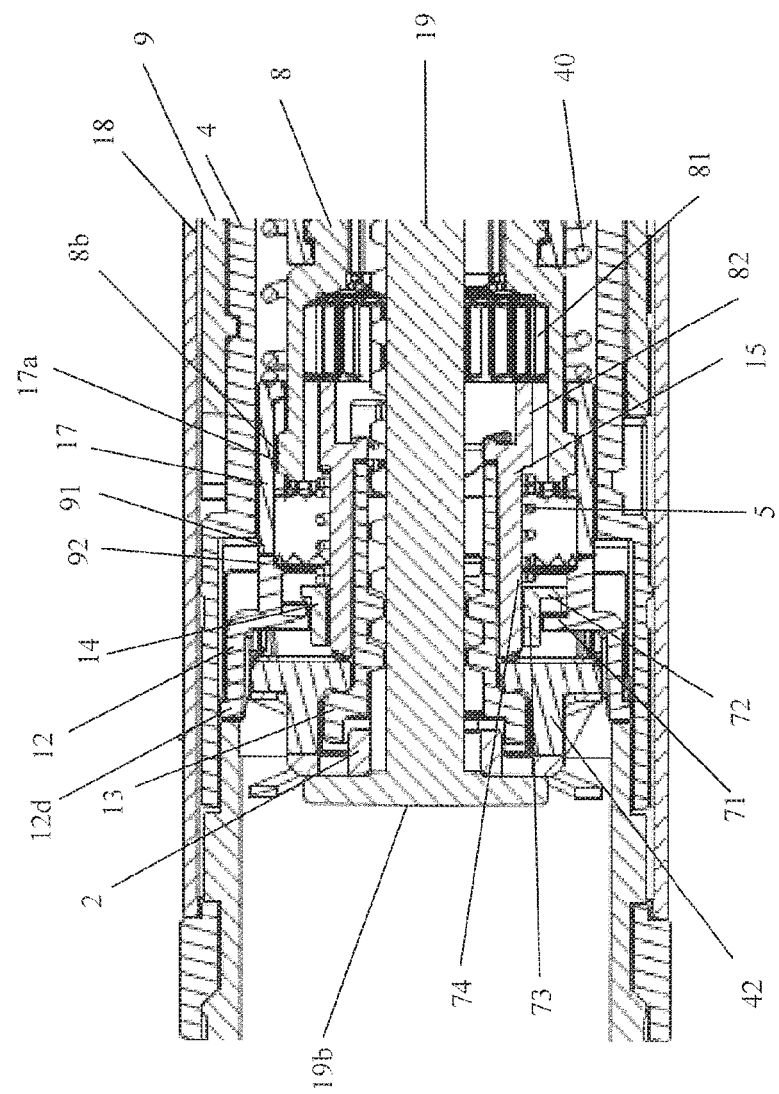
FIG. 21 shows detail of cross sectional view of a drive and dosing device according to the third embodiment in an initial state before setting of a dose.

The drive and dosing device according to the third embodiment has a mechanism which during dose dialing (e.g. dial up or dial down) produces acoustic and/or tactile signals that can be designated as clicks and which dictate discrete angular steps to the dose knob 10 during dose dialing and which correspond to the International Units (IU) set and/or corrected (see, e.g., FIGS. 19 and 21). The mechanism comprises a sleeve shaped ratchet ring 17 which is concentrically arranged around the distal end of the drive sleeve 8. Protrusions 8b on the outside of the drive sleeve 8 engage grooves 17a present on the inside of the ratchet ring 17 to form a rotationally secure connection during dose setting. The ratchet ring 17 has a first clicker surface 91 circumferentially arranged at the distal end of the ratchet ring 17 and includes a tooth structure with the teeth pointing in the distal direction. The teeth have two sloped surfaces and the sloped surface of each side of a single tooth can be inclined differently, but preferably the slopes are equal (e.g., resulting in symmetrically shaped teeth). The ratchet ring 17 is biased by the dose spring 40 which on its distal end abuts the proximal end of the ratchet ring 17 and on its proximal end touches the disc 41 that is axially fixed to the drive sleeve 8. The second clicker surface 92 is located at the switching element 12 and comprises a tooth structure circumferentially arranged on the proximal surface of the switching element 12 with the teeth pointing in the proximal direction. The second clicker surface 92 has preferably complementary teeth to the first clicker surface that can ratchet with the teeth of the first clicker surface 91. The second clicker surface 92 is rotationally and axially secure connected to the switching element 12 which itself is rotationally secured with respect to the housing (e.g., the second clicker surface 92 is rotationally secured with respect to the housing 4, 18). During dose setting, the dose knob 10 is rotated for setting a particular dose and the scale drum 9 and dose sleeve 7 are rotated out of the housing 4, 18. The drive sleeve 8 is rotated due to the key-cam engagement 7c, 8c and with the drive sleeve 8 also the ratchet ring 17 will rotate because of the engagement between protrusion 8b and grooves 17a. The first clicker surface 91 of the rotating ratchet ring 17 will ratchet against the second clicker 92 of the non-rotating switching element 12 under the resilient forces of the reset spring 40. The ratchet ring 17 will ratchet versus the switching element 12. The individual tooth of the first and second clickers surfaces 91, 92 are spaced apart such that each step corresponds to 1 IU (e.g., each click of the ratchet system during dial up or dial down of a dose corresponds to 1 IU). When the dose knob 10 is actuated and moved from the non-actuated to the actuated position, the drive sleeve 8 is also moved in the distal direction with respect to the housing over the actuation distance thereby bringing the coupling 81, 82 into engagement. Before the engagement of the coupling 81, 82 it is preferred to disengage the coupling 8b, 17a between the dose sleeve 8 and the ratchet ring 17, the reverse (e.g. first closing the coupling 81, 82 before decoupling the coupling 8b, 17a) is a more preferred option.

During decoupling the coupling 8b, 17a, the protrusion 8b is brought out of engagement with the grooves 17a. Thus the ratchet system for generating the clicks is non-active once the dose knob 10 has been actuated.

During actuation of the dose knob 10, a torque in the second direction can be generated in the drive train, more specifically the torque due to the threaded engagement between the dose sleeve 7 and the coupling sleeve 6 and/or the housing insert 4 and the scale drum 9. This torque during actuation (e.g. during movement from the non-actuated to the actuated position) could result in an undesirable rotation in the second direction of the drive sleeve 8. This torque moment can be compensated for by the bidirectional ratchet coupling 91, 92 and/or the unidirectional coupling 71, 72. The latter is intended to prevent a rotation in the first rotation direction by its asymmetric tooth structures but also has, although much lower, a resistance to rotation in the first direction which is needed for generating the clicks during dose delivery, as will be described below.

Upon further pressing the dose knob 10 after having moved over the actuation distance, the dose knob 10 moves in the distal direction and the scale drum 9, dose sleeve 7 and drive sleeve 8 co-rotate in the second rotation direction. The dispense coupling 81, 82 is closed and therefore also the rotation member 13, 15 rotates in the second rotation direction whereby the coupling ring 14 also rotates in the second rotation direction due to the internal/external tooth connection 73, 74. The coupling ring 14 is biased by the dose spring 5 which is located between the drive nut socket 15 of the rotation member 13, 15 and the proximal surface of the coupling ring 14. The distal surface of the coupling ring 14 comprises the second coupling structure 72, shaped as a saw tooth structure that engages the first coupling structure 71 present at the switching element 12. The two saw tooth structures are pushed into engagement by the dose spring 5 thereby forming the unidirectional coupling 71, 72 that prevents rotation of the rotation member 13, 15 in the first rotation direction. When the rotation member 13, 15 rotates in the second rotation direction during dose dispensing, the saw tooth of the coupling structures 71, 72 ratchet over each other thereby producing the audible and/or tactile clicks during dose delivery.

During reset of the drive and dosing mechanism, the cartridge holder 11 is removed and the switching element 12 moves in the distal direction due to the spring force of reset spring 40 and thereby the first coupling structure 71 disengages from the second coupling structure 72.

The second coupling structure 72 is located at the coupling ring 14 which itself is biased by dose spring 5. When the cartridge holder is removed, the coupling 71, 72 is decoupled due to the distal movement of the switching element 12. The distal movement of the coupling ring 14 is restricted by the bearing disc 42 and the coupling 71, 72 is decoupled due to the distal movement of the switching element 12 (see, e.g., FIG. 29). The coupling 73, 74 between the coupling ring 14 and the rotation member 13, 15 remains in the coupled state during reset of the drive and dosing mechanism.

The drive and dosing mechanism of the third embodiment uses a separate dose spring 5 dedicated to the unidirectional coupling 71, 72 and a separate reset spring 40 for the dose setting click mechanism 91, 92, the reset of the dose knob 10 to the non-actuated state and the distal movement of the switching element 12 when the cartridge holder 11 is removed, respectively. The drive and dosing mechanism of the first embodiment uses one dose spring 5 for all four functionalities (see, e.g., FIG. 1). During dose delivery, a substantial amount of the frictional losses is caused by the dispensing clicking mechanism and those frictional losses are proportional to the normal forces governed by the separate dose spring of the third embodiment and the combined dose spring of the first embodiment, respectively. The force efficiency (E) of the drive and dosing mechanism is calculated as the ratio between the forces acting on the plug of the ampoule ($F_{out}$) divided by the axial forces applied to the dose knob 10 or dose button 21, ($F_{in}$).

The sum of the moments and forces of the drive and dosing mechanism can be calculated with the following (generalized) formula:

$$F_{in} = F_{out} + \Sigma F_{Loss}i$$

The frictional losses can be calculated with:

$$F_i = \mu_i \times F_i^N$$

The force efficiency E of the device is defined as:

$$E = \frac{F_{out}}{F_{in}}$$

Whereby $\mu_i$ is the specific frictional coefficient and $F_i^N$ the normal force For the first embodiment using one dose spring (defining the normal force on several components):

$$F_{in} = F_{out} + F_{Loss}^{(scale\ drum9\text{-}housing\ insert4)} +$$
$$F_{Loss}^{(dose\ sleeve\ 7\text{-}clutch6)} + F_{Loss}^{(drive\ sleeve8\text{-}clutch6)} +$$
$$F_{Loss}^{(dose\ sleeve7\text{-}drive\ sleeve8)} +$$
$$F_{Loss}^{(drive\ nut\ 13\text{-}piston\ rod19)} +$$
$$F_{Loss}^{(dose\ click\ disc\ 14\text{-}dose\ click\ ratchet\ 12)} +$$
$$F_{Loss}^{(piston\ rod\ 19\text{-}linear\ slide2)}$$

The dose spring 5 in the first embodiment serves several purposes, such as:

1) generating the resilient force needed for the clicks during dose dispensing between the dose click disc 14 and the dose click ratchet 12;
2) generating the resilient force needed for dose setting/adjustment clicks between the dose adjustment ratchet 16 and the dose adjustment click disc 17 (dose setting) between the dose adjustment click disc 17 and the drive sleeve 8 (dose correction);
3) Reset from dose dispensing to the dose setting mode; and
4) Reset of the device during exchange of a cartridge.

The dose spring of the first embodiment is adjusted to the highest force needed of the 4 functionalities listed above and therefore produces normal forces $F_n$ between the drive sleeve 8 and the clutch 6 which, in combination with the unavoidable frictional coefficient existing between the two adjacent surfaces, lead to high frictional losses during dose dispensing and therewith reducing the efficiency of the device.

For the third embodiment, one dose spring 5 and one reset spring 40 are used (defining the normal forces):

$$F_{in} = F_{out} + F_{Loss}^{(scale\ drum9\text{-}housing\ insert4)} +$$
$$F_{Loss}^{(dose\ sleeve\ 7\text{-}clutch6)} + F_{Loss}^{(drive\ sleeve8\text{-}clutch6)} +$$
$$F_{Loss}^{(dose\ sleeve7\text{-}drive\ sleeve8)} +$$
$$F_{Loss}^{(drive\ nut\ 13\text{-}piston\ rod19)} +$$
$$F_{Loss}^{(coupling\ ring\ 14(72)\text{-}switching\ element\ 12(71))} +$$
$$F_{Loss}^{(piston\ rod\ 19\text{-}linear\ slide2)}$$

The dose spring 5 in the third embodiment is adjusted to one specific need only, generating the clicks using the unidirectional coupling elements 71 and 72 during dose dispensing. The spring forces needed for the clicker functionality are lower. As a consequence, the normal forces acting between the bearing surfaces of the click disc (coupling ring 14) are lower and therewith also the frictional losses which improves the efficiency of the driving mechanism.

The reset spring 40 is needed for:

1) generating the resilient force needed for dose setting/adjustment clicks between the ratchet ring 17 (91) and the switching element 12 (92) (dose setting and correction);
2) Reset from dose dispensing to the dose setting mode; and
3) Reset of the device during exchange of a cartridge.

Based on the above described model the device efficiencies have been calculated using the following spring forces:

First embodiment—Dose spring 5 with a force ranging from 1 N to 4 N, preferably between 1.5 and 3 N, more preferably 2 N.

Third embodiment—Dose spring 5 with a force ranging between 0 and 1 N, preferably between 0.25 and 0.75 N, more preferably 0.5 N and a reset spring with a force ranging between 1 N and 3 N, preferably 2 N.

Figure 30A:
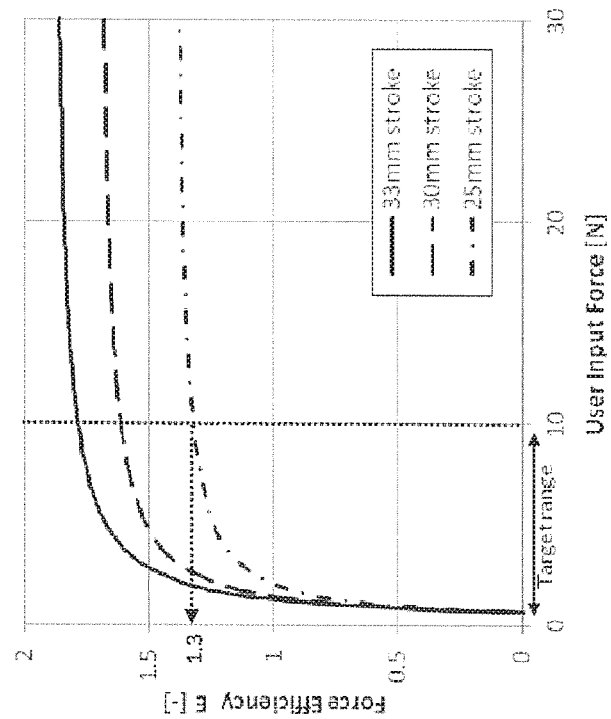
FIG. 30a shows device efficiency ($F_{out}/F_{in}$) versus the user input force ($F_{in}$) for the device according to the first embodiment having one dose spring. Data are shown for 3 different stroke lengths: 25 mm, 30 mm and 33 mm.
Figure 30B:
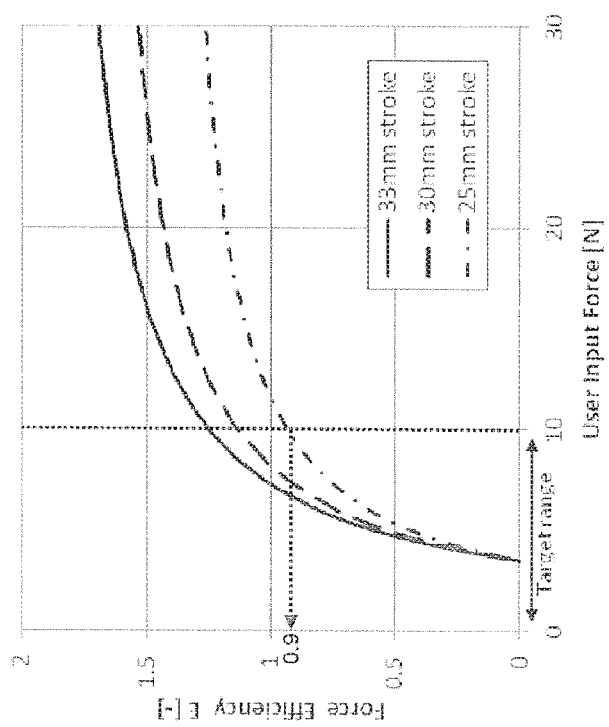
FIG. 30b shows device efficiency ($F_{out}/F_{in}$) versus the user input force ($F_{in}$) for the device according to the third embodiment having a separate dose spring and a reset spring. Data are shown for 3 different stroke lengths: 25 mm, 30 mm and 33 mm.

The device force efficiencies (device output/user input force) have been calculated for different maximum dose stroke (dose setting) setting distances for the device according to the first embodiment (see FIG. 30a) and the third embodiment (see FIG. 30b). The dose setting distance or dose stroke is defined as the maximum axial displacement that the dose knob can be rotated out of the proximal end of the housing 4, 18. A higher dose setting distances calls for a higher pitch of the thread 4a, 9c between the housing insert 4 and the scale drum 9 (and thus also an equally higher pitch of the thread 7b, 6b between the dose sleeve 7 and the clutch 6). A higher pitch of the dose setting members implies, at a constant pitch of the thread 19a of the piston rod, also a higher gearing ratio of the device. Due to the gearing ratio of the device it is possible to have a higher output force compared to the input force (device force efficiencies above 1).

The combination of the users requirements in terms of dose setting distance (stroke length for the users thumb), force applied on the dose knob/dose button and desired device efficiency, defines a window for optimum operation of the drive and dosing mechanism. The user's input force for operating the device is targeted at the range of 0 N to 10 N and the stroke length for the thumb ranging between 25 mm and 33 mm. If device efficiencies above 1 are preferred, then this is feasible for the drive and dosing mechanism according to the first embodiment with a stroke length of 30 mm whereas 25 mm is sufficient for the third embodiment (see arrows in FIGS. 30a and 30b). In other words, the reduction of the frictional losses due to an optimized clicker mechanism for dose dispensing results in higher device efficiency for a certain stroke length and/or users input force.

What is claimed is:

1. A drive and dosing device for an injection device configured for the attachment of a cartridge, the drive and dosing device comprising:
a housing;
a piston rod comprising a distal end and a thread, the piston rod moveable in a dispensing direction with respect to the housing for dispensing a product;
a rotation member engaged with the thread of the piston rod and rotationally secured to a stop limiter, wherein the rotation member is engaged with the thread of the piston rod such that the rotation member causes the piston rod to move in the dispensing direction when the rotation member is rotated in a first direction relative to the piston rod;
a dose knob rotatable in a dose setting direction relative to the housing or the piston rod to increase a dose to be dispensed from the cartridge; and
a stop element comprising a catch, the stop element threadedly engaged with the thread of the piston rod,
wherein the dose knob is coupled with the stop element such that rotating the dose knob in the dose setting direction results in rotating the stop element relative to the piston rod, whereby the stop element is moved towards the distal end of the piston rod and the catch is moved towards the stop limiter, and
wherein the stop element prevents rotation of the dose knob in the dose setting direction when the catch abuts the stop limiter.

2. The device according to claim 1, wherein the dose knob is rotatable in a direction opposite the dose setting direction for decreasing the dose to be dispensed, and
wherein rotation of the dose knob relative to the piston rod in the direction opposite the dose setting direction causes the catch to move away from the stop limiter and the stop element to rotate relative to the piston rod and be moved towards a proximal end of the piston rod.

3. The device according to claim 1, further comprising an actuation element, wherein upon actuating the actuation element, the actuation element is configured to cause the rotation member to rotate relative to the housing and the piston rod such that the piston rod moves relative to the housing in the dispensing direction and the stop element is moved towards a proximal end of the piston rod.

4. The device according to claim 3, wherein upon actuating the actuation element, a distance between the stop limiter and the catch remains constant.

5. The device according to claim 1, further comprising a unidirectional coupling between the housing and the rotation member, the unidirectional coupling enabling the rotation member to rotate in one direction such that the piston rod is moved in the dispensing direction, and wherein the unidirectional coupling prevents a rotation in the direction opposite the dispensing direction.

6. The device according to claim 5, wherein the unidirectional coupling is configured to be switched between an activated state and an inactivated state, wherein in the activated state, the unidirectional coupling permits a rotation of the rotation member in a rotation direction which moves the piston rod in the dispensing direction and prevents rotation in a direction opposite the dispensing direction, and wherein in the inactivated state, the unidirectional coupling permits a rotation of the rotation member in the direction opposite the dispensing direction.

7. The device according to claim 6, further comprising:
a cartridge holder configured to removably receive a cartridge and to couple to the distal end of the housing; and
a switching element arranged between the cartridge holder and the unidirectional coupling,
wherein the switching element is movable relative to the housing in a proximal direction upon coupling the cartridge holder to the housing thereby switching the unidirectional coupling to the activated state, and
wherein the switching element is movable in the distal direction upon removing the cartridge holder thereby switching the unidirectional coupling to the inactivated state.

8. The device of claim 6, wherein the engagement between the rotation member and the thread of the piston rod comprises interlocking threading having a pitch configured to prevent self-locking when the piston rod, with the inactivated unidirectional coupling, is reset opposite to the dispensing direction, whereby the rotation member rotates in the direction opposite the dispensing direction.

9. The device of claim 1, further comprising a scale drum rotationally coupled to the dose knob, the scale drum comprising a helically-shaped scale,
wherein the housing comprises a viewing window configured to expose a portion of the helically-shaped scale corresponding to the dose to be dispensed, and
wherein the scale drum is configured to rotate relative to the housing upon rotation of the dose knob thereby causing a portion of the dose scale corresponding to the dose to be dispensed to be exposed.

10. The device of claim 9, wherein the scale drum is rotatable between a zero dose position and a maximum dose position, and
wherein the scale drum comprises:
a stop zero dose in the zero dose position of the scale drum configured to prevent rotation of the scale drum in the direction opposite the dose setting direction and permit rotation in the dose setting direction, and
a stop maximum dose in the maximum dose position of the scale drum configured to prevent rotation of the scale drum in the dose setting direction and permit rotation in the direction opposite the dose setting direction.

11. The drive and dosing device of claim 10, wherein the catch of the stop element is configured to abut the stop limiter when an increased dose would exceed a dispensable amount of product present in the cartridge, thereby preventing rotation of the scale drum in the dose setting direction.

12. The drive and dosing device of claim 1, wherein the stop element is coupled with the dose knob such that the stop element is rotated along the piston rod during setting of the dose to be dispensed and during dispensing.

13. The drive and dosing device of claim 1, further comprising:
an actuation element configured to be actuated for dispensing the dose to be dispensed; and
a dispense coupling,
wherein the dispense coupling is closed when the actuation element is actuated and is opened when the actuation element is released, wherein the rotation member is rotationally coupled with the dose knob when the dispense coupling is closed, and wherein the rotation member is rotatable with respect to the dose knob when the dispense coupling is open.

14. The drive and dosing device of claim 1, wherein the stop element is rotationally coupled to the dose knob during dose setting and during dispensing.

15. The drive and dosing device of claim 1, further comprising a sleeve kinematically positioned between the dose knob and the stop element, wherein the stop element is engaged with the sleeve such that the stop element is rotationally secure and axially slidable relative to the sleeve, and wherein the sleeve is coupled to the dose knob such that the sleeve and the dose knob are rotationally secure relative to each other.

16. The drive and dosing device of claim 1, wherein the stop element is in a position with respect to the piston rod before a dose to be dispensed is set, and wherein the stop element is in the position after dispensing the set dose to be dispensed.

* * * * *

UNITED STATES PATENT AND TRADEMARK OFFICE
CERTIFICATE OF CORRECTION

PATENT NO. : 10,143,806 B2  
APPLICATION NO. : 14/997002  
DATED : December 4, 2018  
INVENTOR(S) : Juerg Hirschel et al.

Page 1 of 1

It is certified that error appears in the above-identified patent and that said Letters Patent is hereby corrected as shown below:

In the Specification

| Column | Line | PTO | Should Be |
|---|---|---|---|
| 43 | 37 | "$F_i = /\mu_i \times F_i^N$" | -- $F_i = \mu_i \times F_i^N$ -- |

Signed and Sealed this  
Second Day of April, 2019

Andrei Iancu  
*Director of the United States Patent and Trademark Office*